(12) United States Patent
Sinnott et al.

(10) Patent No.: US 9,629,708 B2
(45) Date of Patent: *Apr. 25, 2017

(54) SOFT TISSUE REPAIR

(71) Applicant: Smith & Nephew, Inc., Memphis, TN (US)

(72) Inventors: Mary Sinnott, Logan, UT (US); Thomas W Fallin, Hyde Park, UT (US); Kwan-Ho Chan, Singapore (SG); Patrick White, Avondale, PA (US)

(73) Assignee: Smith & Nephew, Inc., Memphis, TN (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/537,777

(22) Filed: Nov. 10, 2014

(65) Prior Publication Data

US 2015/0066059 A1 Mar. 5, 2015

Related U.S. Application Data

(60) Division of application No. 13/623,837, filed on Sep. 20, 2012, now Pat. No. 8,882,834, which is a
(Continued)

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0469* (2013.01); *A61B 17/0482* (2013.01);
(Continued)

(58) Field of Classification Search
CPC ............ A61B 17/0469; A61B 17/1682; A61B 17/1686; A61B 17/0401; A61B 17/0811; A61B 17/08; A61B 17/17; A61B 17/1739; A61F 2002/0858; A61F 2002/0882; A61F 2002/4243; A61F 2002/4246;
(Continued)

(56) References Cited

U.S. PATENT DOCUMENTS

| 4,929,247 A | 5/1990 | Rayhack |
| 5,042,983 A | 8/1991 | Rayhack |

(Continued)

FOREIGN PATENT DOCUMENTS

| GB | 2475491 A | 5/2011 |
| WO | 2008043380 A1 | 4/2008 |
| WO | 2008076559 A1 | 6/2008 |

OTHER PUBLICATIONS

Malone, Charles. Volar plate repair for posttraumatic hyperextension deformity of the proximal interphalangeal joint. The American Journal for Orthopedics. 39(4):190-194. 2010.*
(Continued)

*Primary Examiner* — Thomas J Sweet
*Assistant Examiner* — Christie Bahena
(74) *Attorney, Agent, or Firm* — Taft Stettinius & Hollister LLP

(57) ABSTRACT

Methods and instruments for repairing soft tissues of a skeletal joint such as for example of the foot or hand are presented.

3 Claims, 76 Drawing Sheets

Related U.S. Application Data continuation-in-part of application No. 13/527,424, filed on Jun. 19, 2012, now Pat. No. 9,357,997, and a continuation-in-part of application No. 13/527,765, filed on Jun. 20, 2012, now Pat. No. 8,801,727.

(60) Provisional application No. 61/568,137, filed on Dec. 7, 2011, provisional application No. 61/505,992, filed on Jul. 8, 2011, provisional application No. 61/506,000, filed on Jul. 8, 2011, provisional application No. 61/506,004, filed on Jul. 8, 2011.

(51) Int. Cl.
*A61B 17/16* (2006.01)
*A61B 17/06* (2006.01)

(52) U.S. Cl.
CPC ...... *A61B 17/0483* (2013.01); *A61B 17/1617* (2013.01); *A61B 17/1682* (2013.01); *A61B 2017/0406* (2013.01); *A61B 2017/0417* (2013.01); *A61B 2017/06042* (2013.01); *A61B 2017/06176* (2013.01); *A61F 2/0805* (2013.01)

(58) Field of Classification Search
CPC ...... A61F 2002/4248; A61F 2002/4251; A61F 2002/4253; A61F 2002/4256; A61F 2002/4258; A61F 2/4241
See application file for complete search history.

(56) References Cited

U.S. PATENT DOCUMENTS

| | | | |
|---|---|---|---|
| 5,059,201 | A | 10/1991 | Asnis |
| 5,176,685 | A | 1/1993 | Rayhack |
| 6,007,535 | A | 12/1999 | Rayhack et al. |
| 2003/0078599 | A1 | 4/2003 | O'Quinn et al. |
| 2003/0078600 | A1 | 4/2003 | O'Quinn et al. |
| 2003/0216742 | A1 | 11/2003 | Wetzler et al. |
| 2004/0015177 | A1 | 1/2004 | Chu |
| 2007/0088362 | A1 | 4/2007 | Bonutti et al. |
| 2007/0233128 | A1 | 10/2007 | Schmieding et al. |
| 2009/0254126 | A1 | 10/2009 | Orbay et al. |
| 2010/0057216 | A1 | 3/2010 | Gannoe et al. |
| 2010/0324563 | A1 | 12/2010 | Green, II et al. |
| 2011/0066165 | A1 | 3/2011 | Skinlo et al. |
| 2011/0144647 | A1 | 6/2011 | Appenzeller et al. |

OTHER PUBLICATIONS

Colton, Chris. Volar Plate Arthroplasty. AO Surgery Reference. Aug. 11, 2008.*

Eaton, Richard. Volar plate arthroplasty of the proximal interphalangeal joint: A review of ten years' experience. The Journal of Hand Surgery. pp. 260-268. 1980.*

Colton (2), Chris. Collateral Ligament Repair. AO Foundation. Aug. 11, 2008.*

Extended European Search Report; European Patent Office; European Application No. 12810809.9; Feb. 15, 2016; 21 pages.

International Search Report; International Searching Authority; International PCT Application No. PCT/US2012/045584; Jan. 31, 2013; 3 pages.

Written Opinion; International Searching Authority; International PCT Application No. PCT/US2012/045584; Jan. 31, 2013; 4 pages.

International Preliminary Report on Patentability; The International Bureau of WIPO; International PCT Application No. PCT/US2012/045584; Jan. 14, 2014; 5 pages.

Supplementary Partial European Search Report; European Patent Office; European Patent Application No. 12810809.9; Apr. 1, 2015; 6 pages.

Australian Patent Examination Report; Australian Patent Office; Australian Patent Application No. 2012282919; Apr. 14, 2016; 3 pages.

* cited by examiner

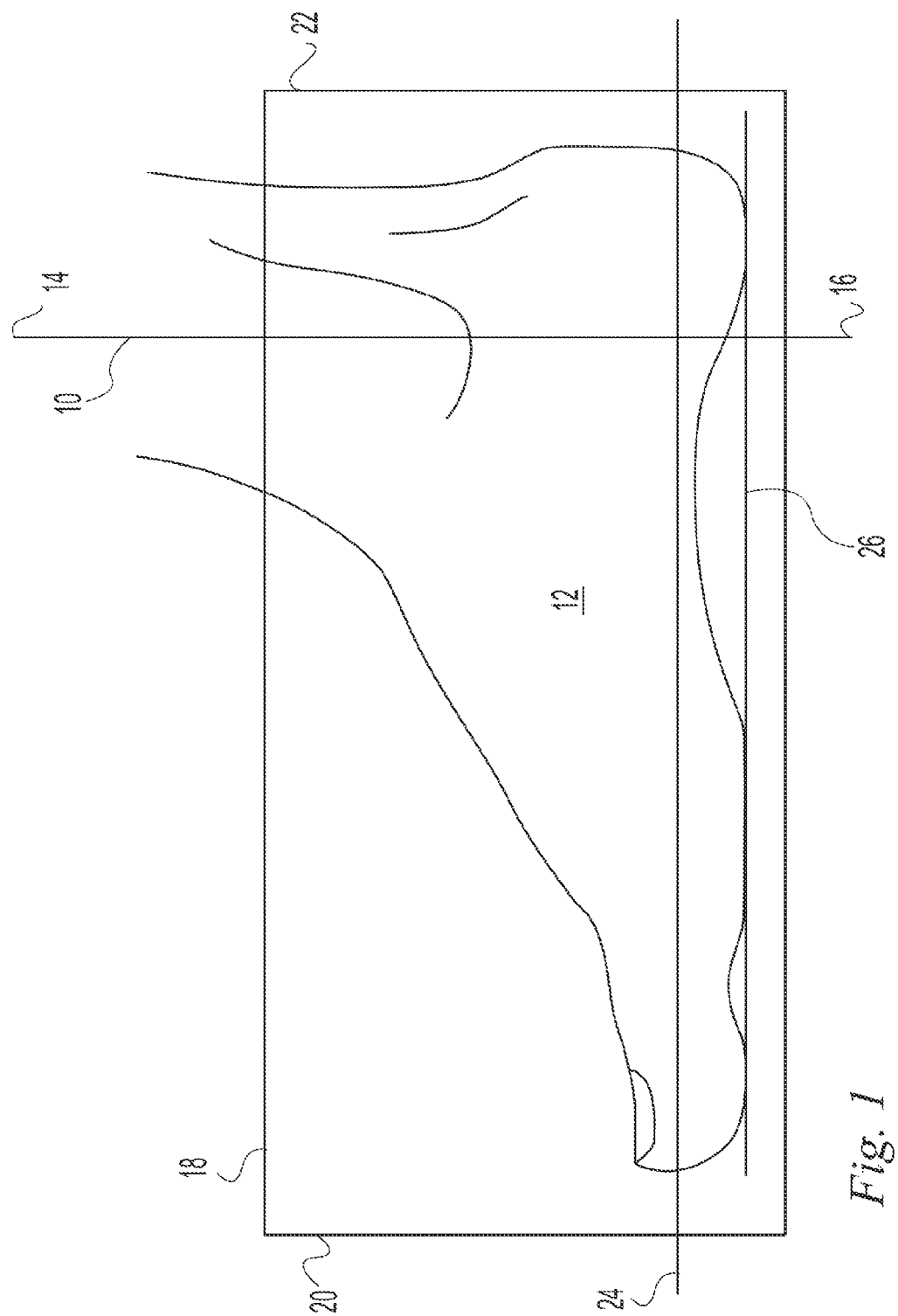

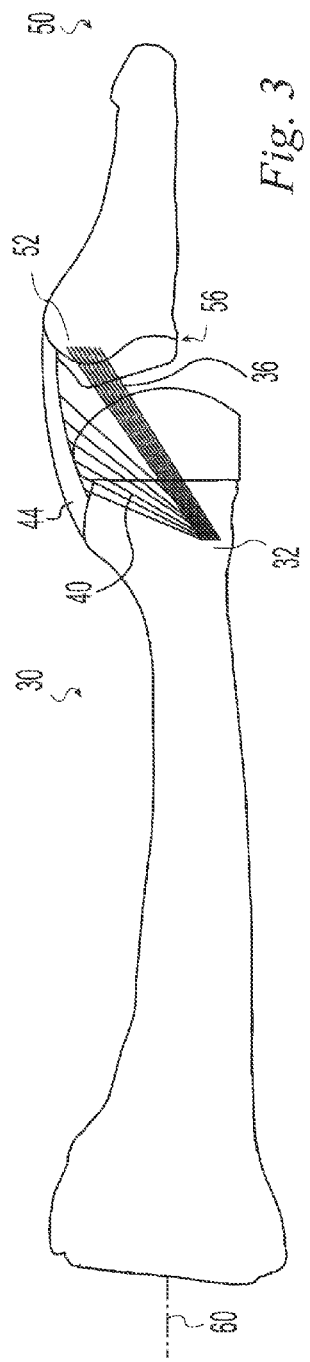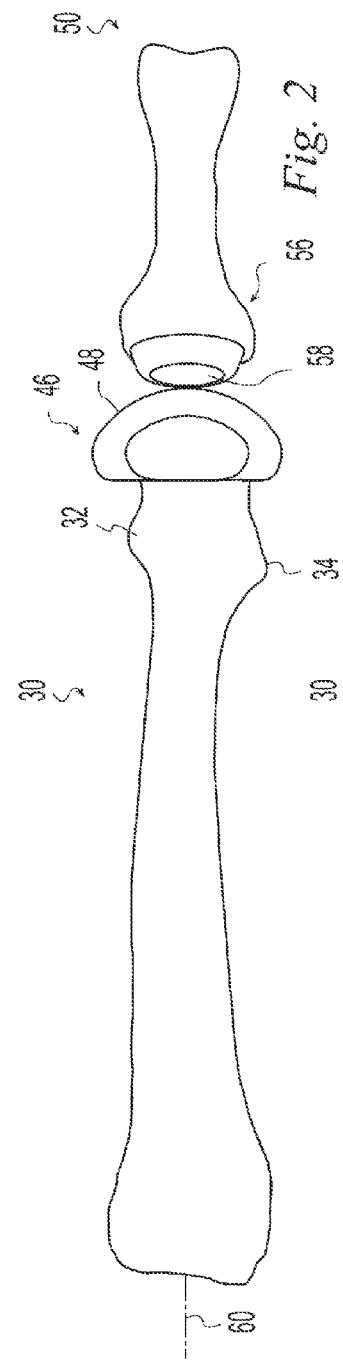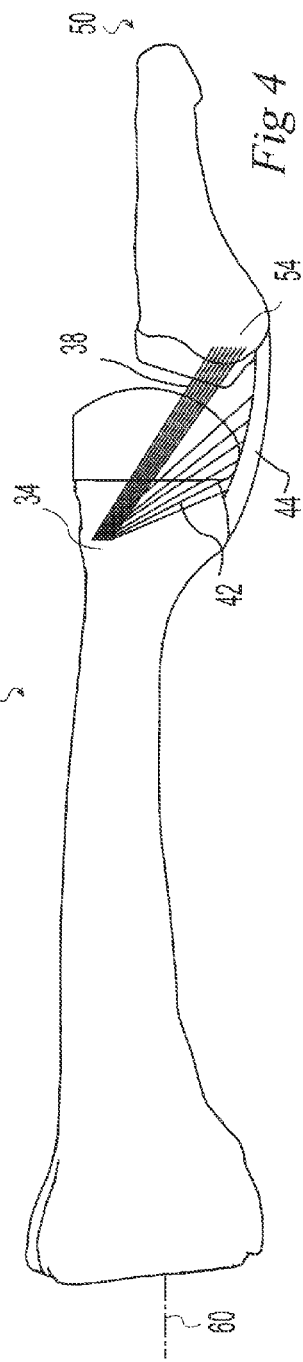

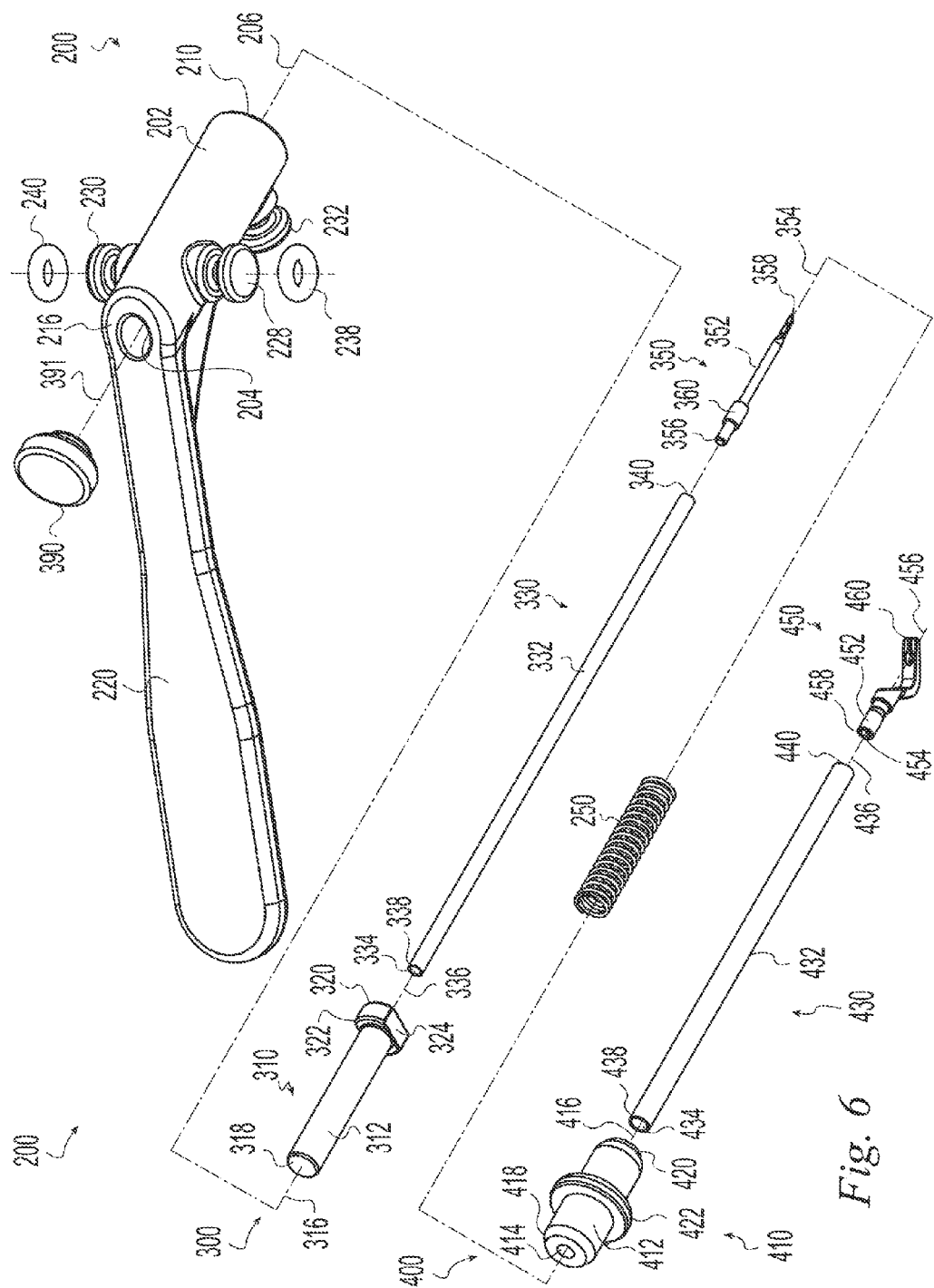

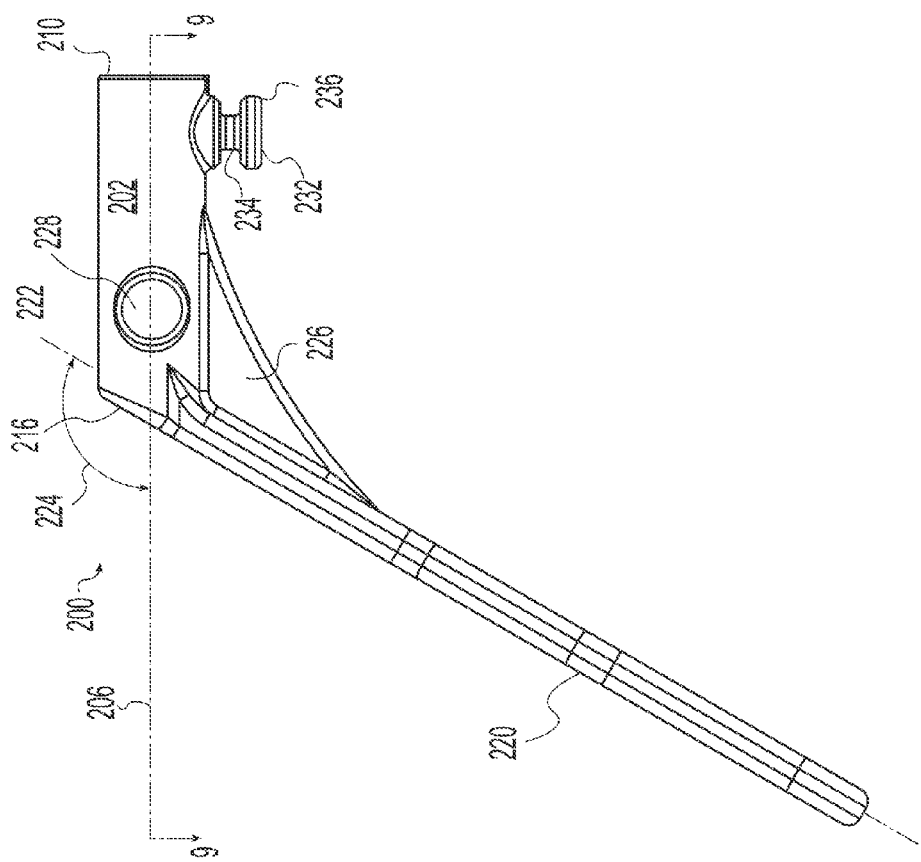
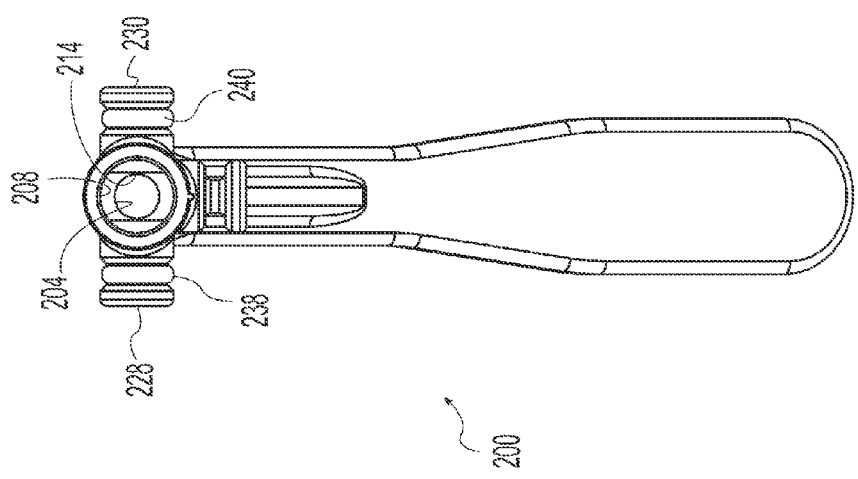
Fig. 8
Fig. 7

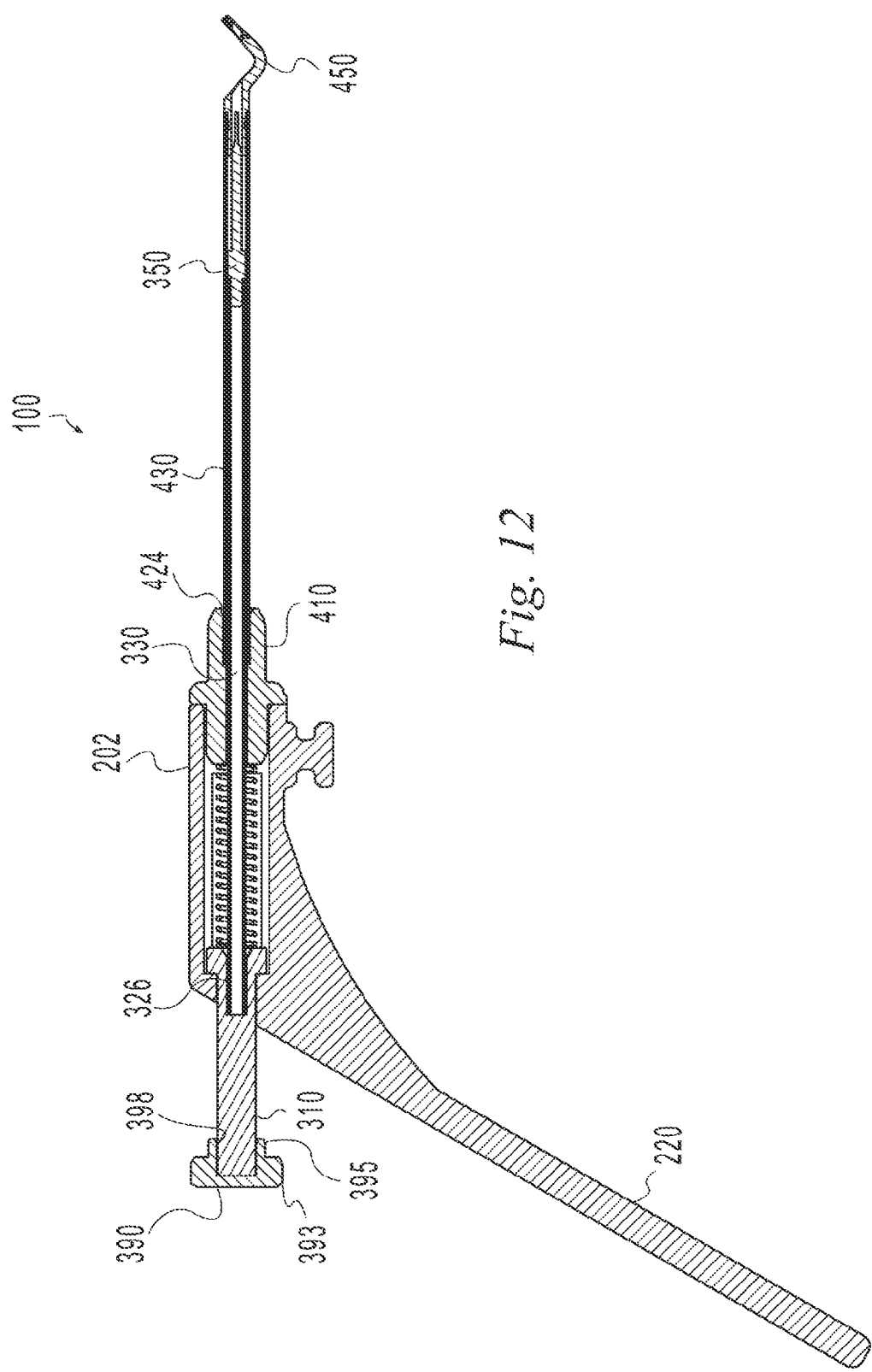

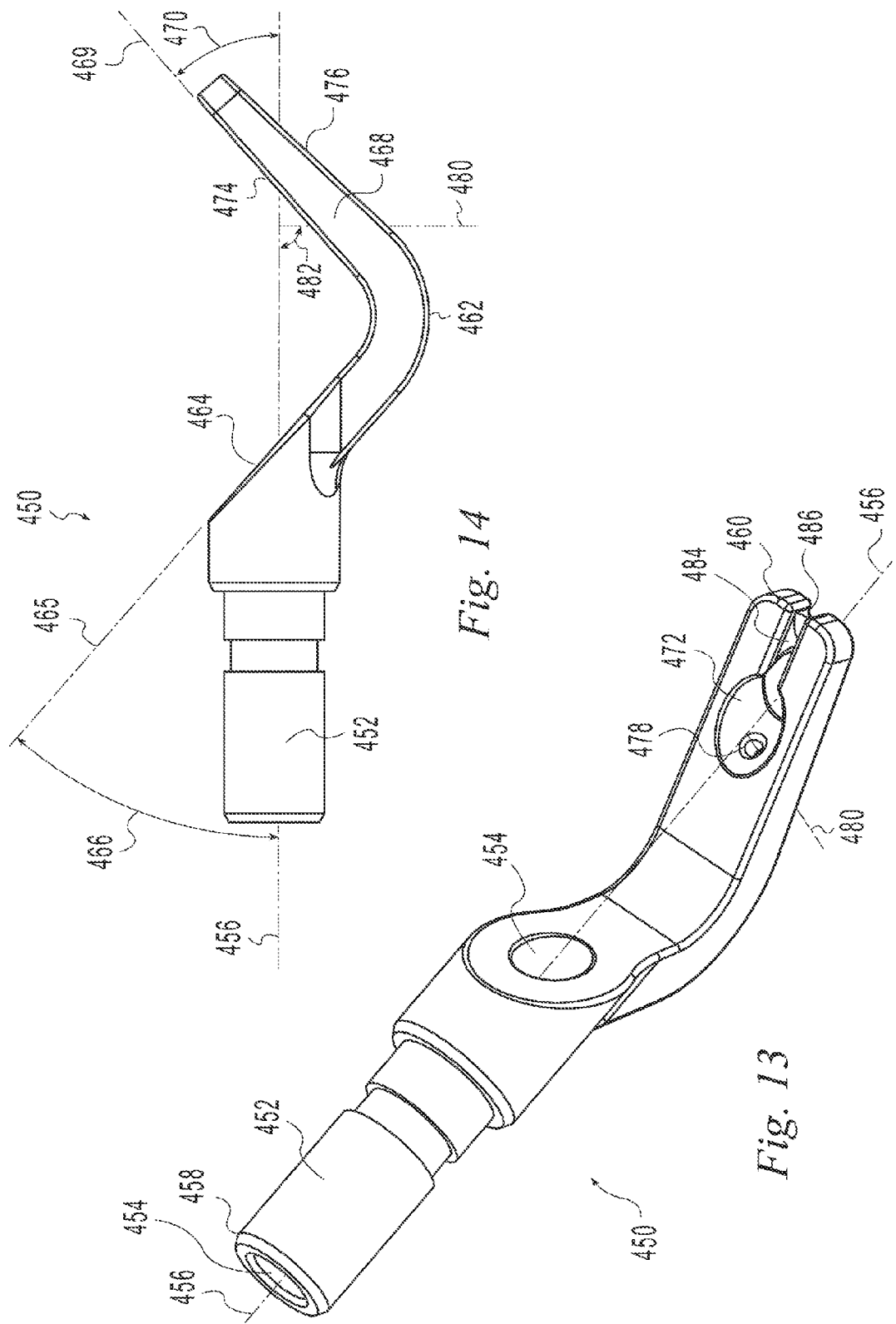

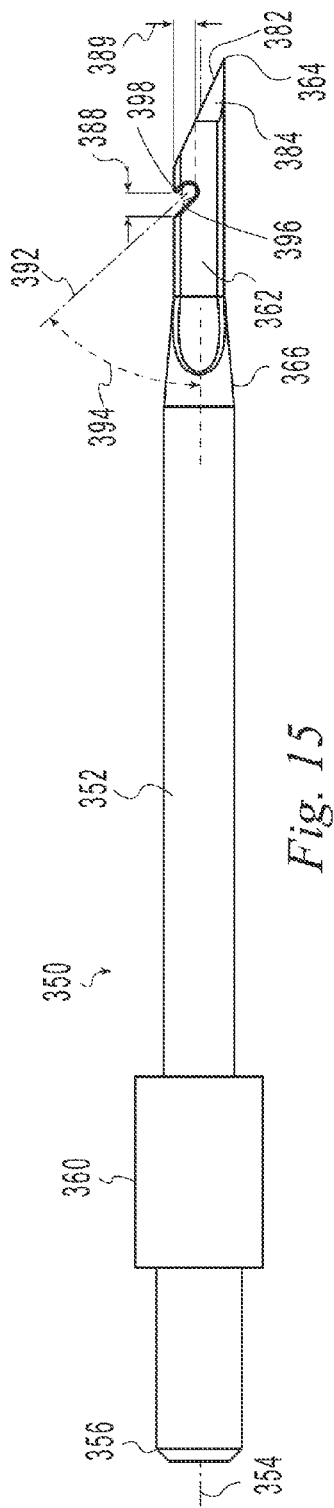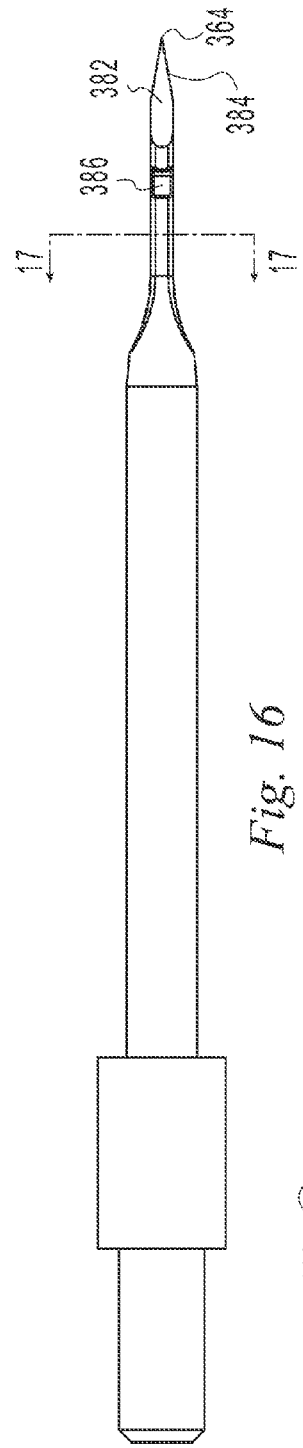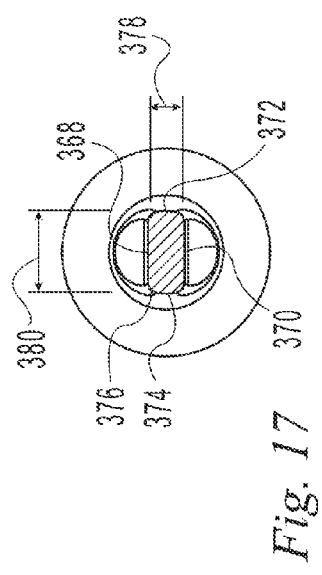

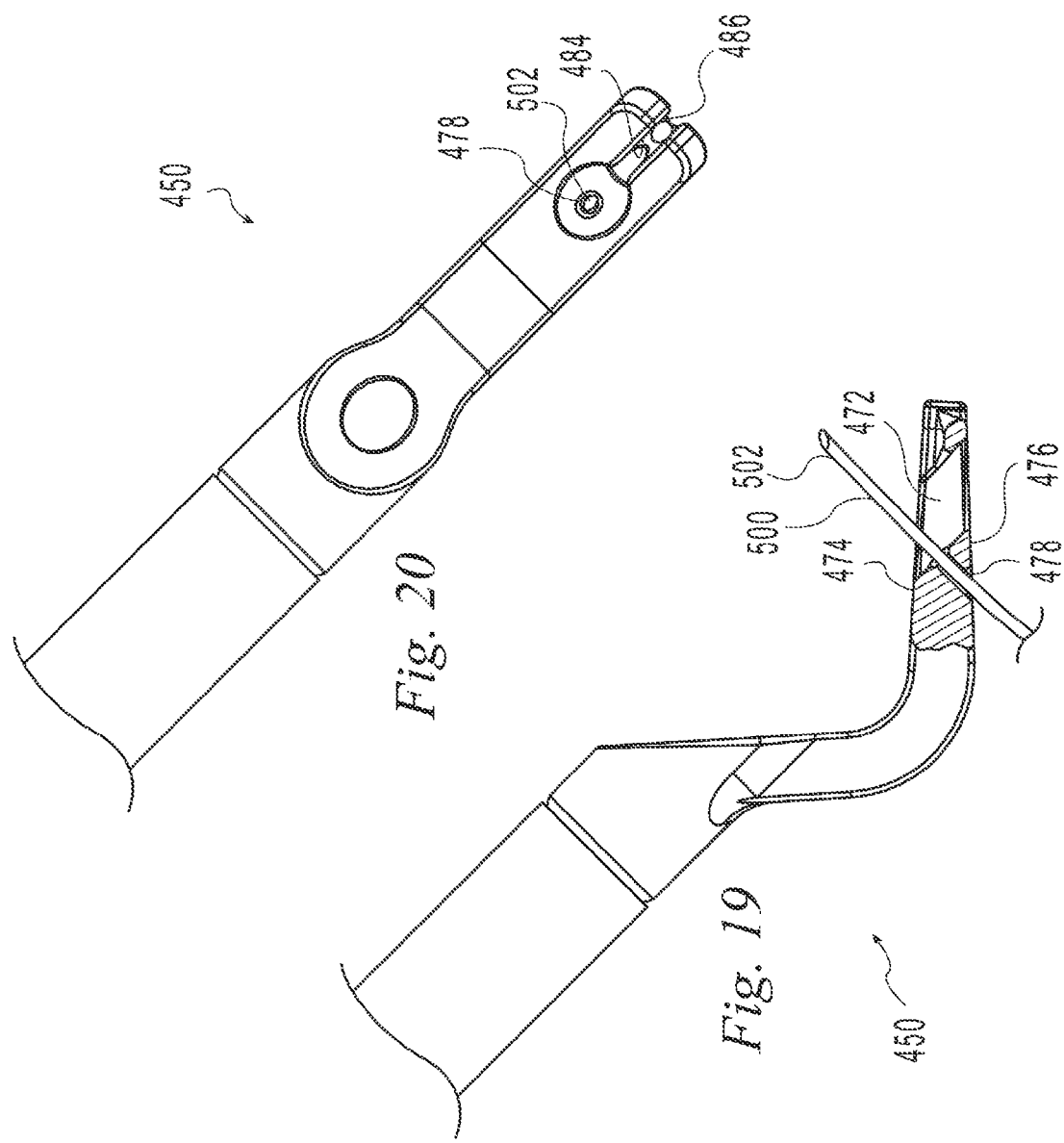

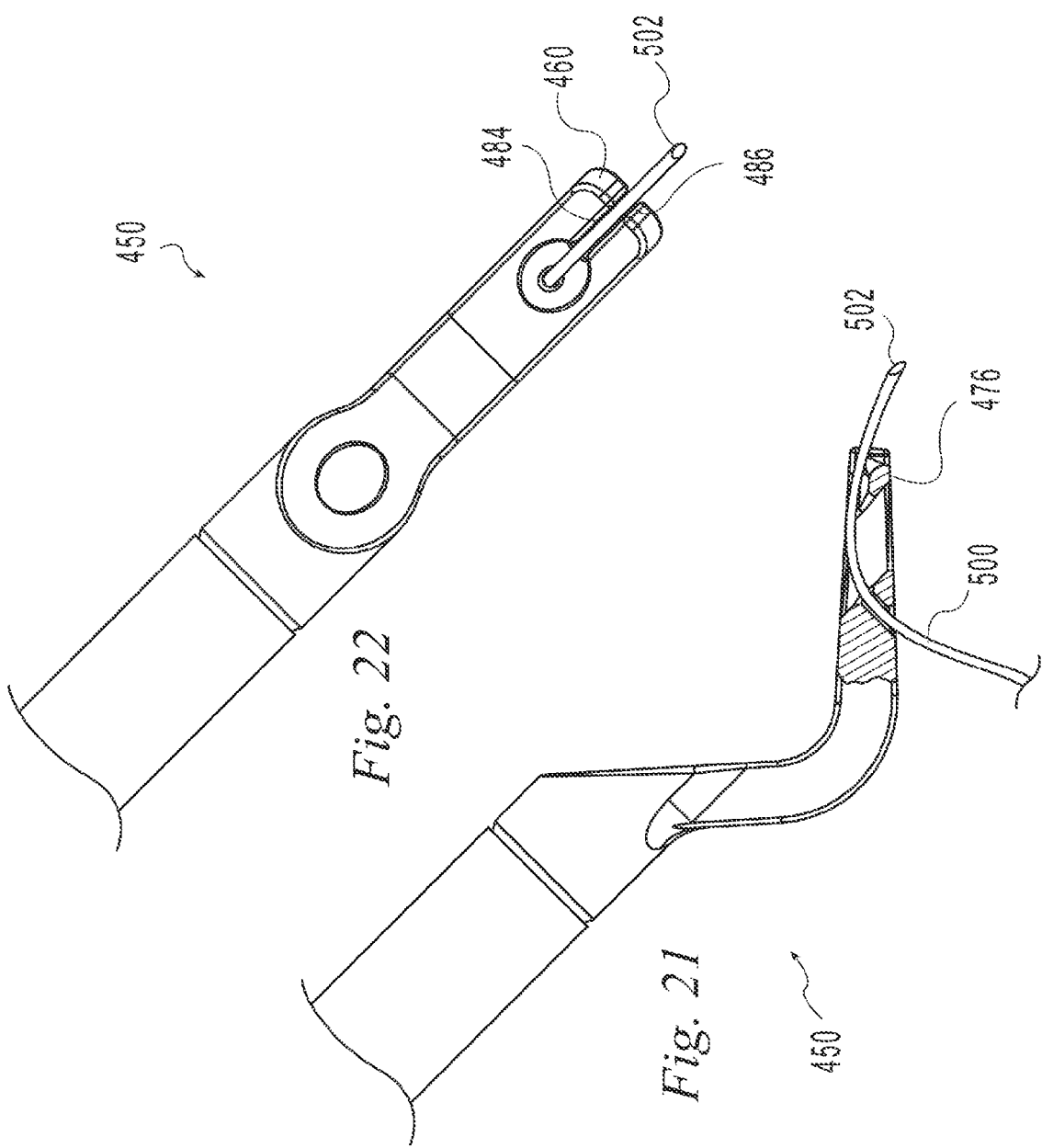

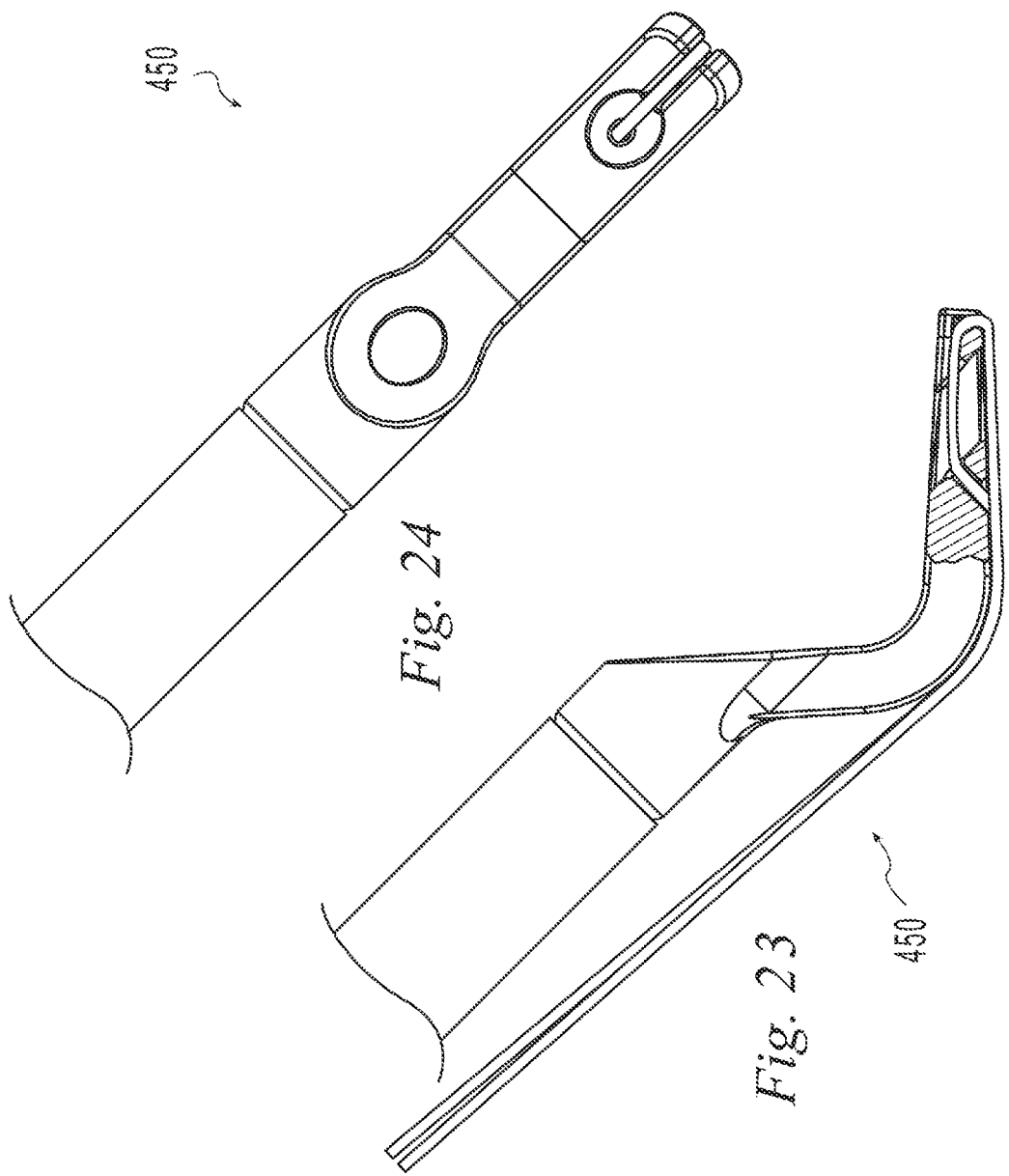

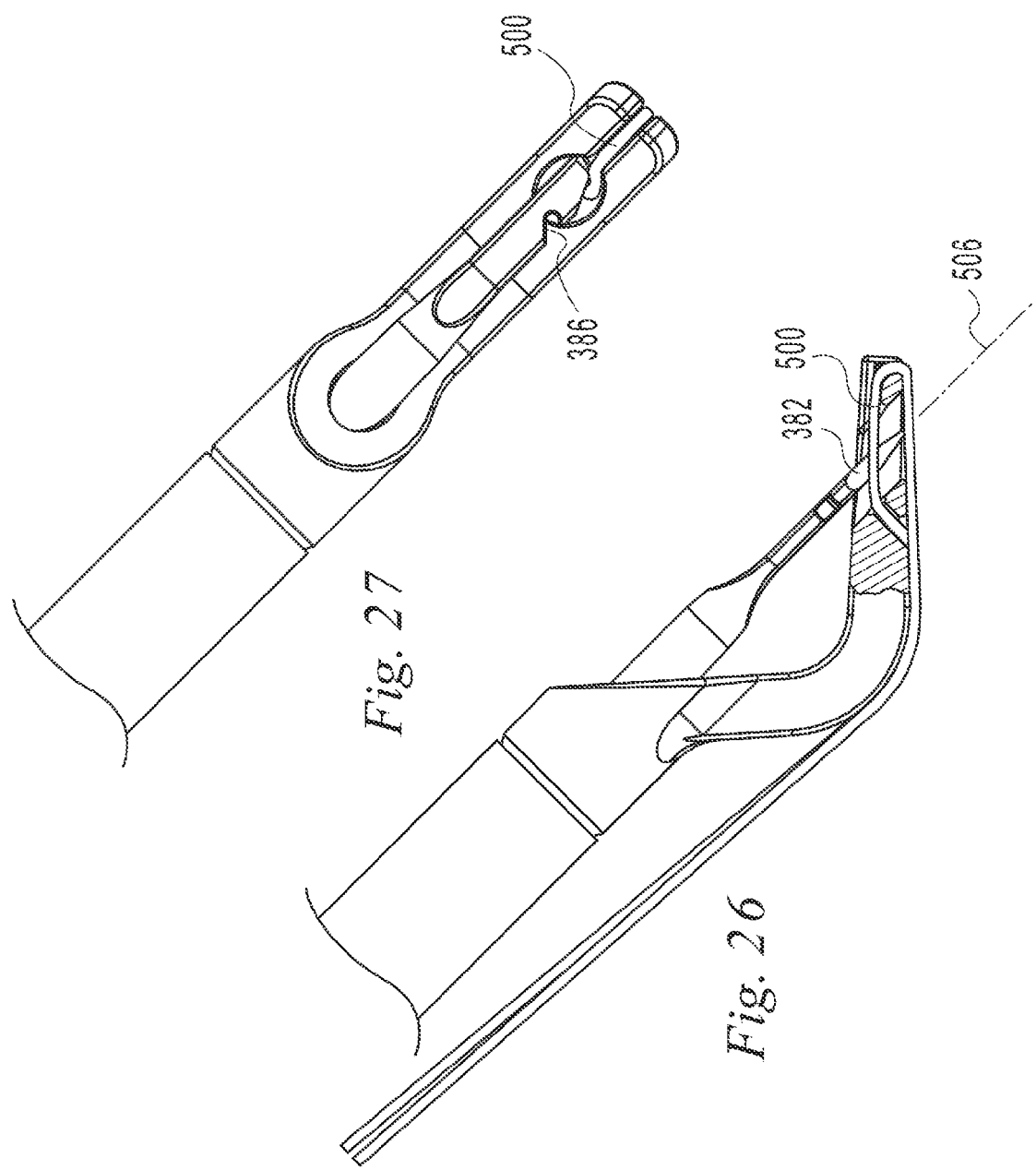

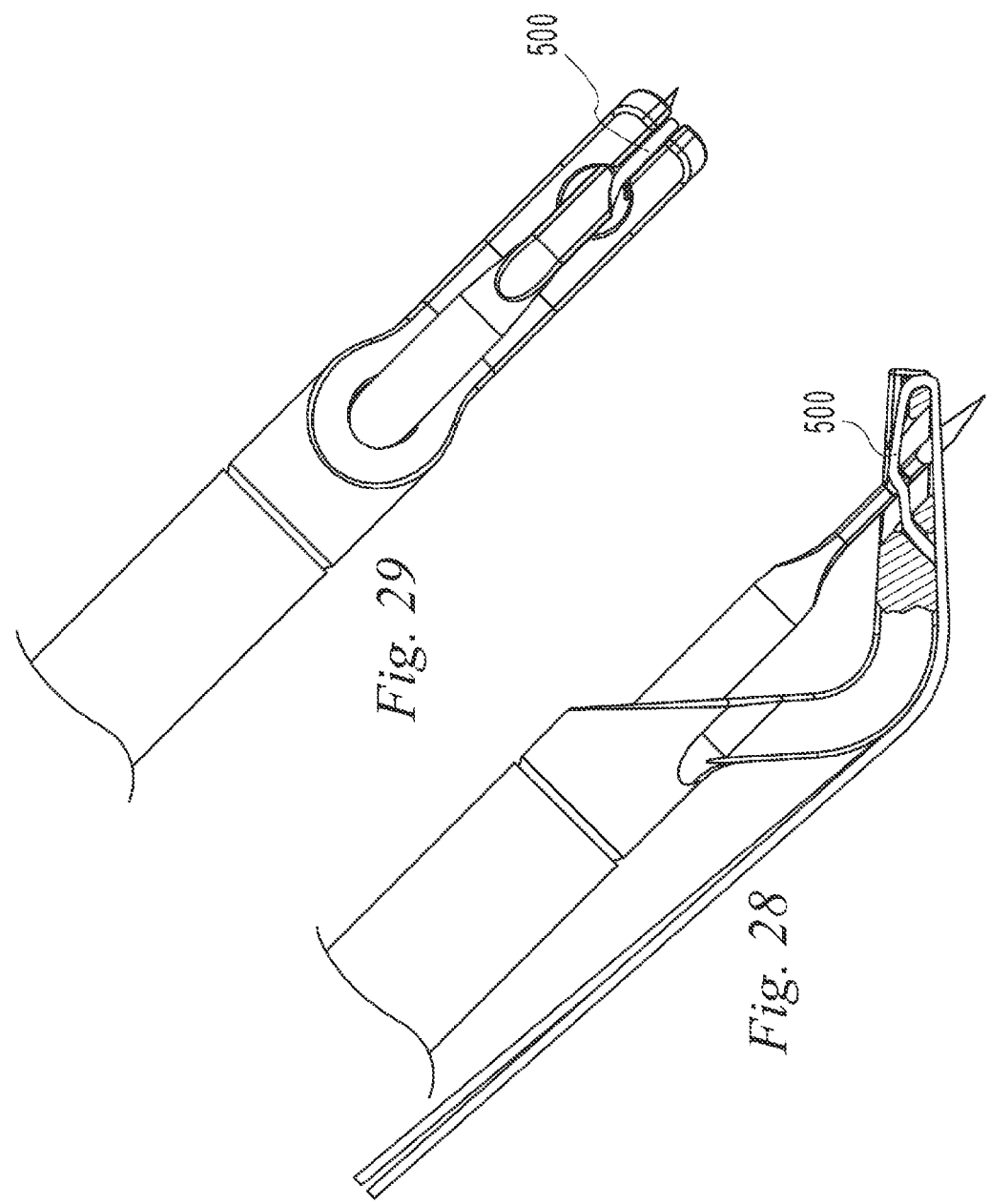

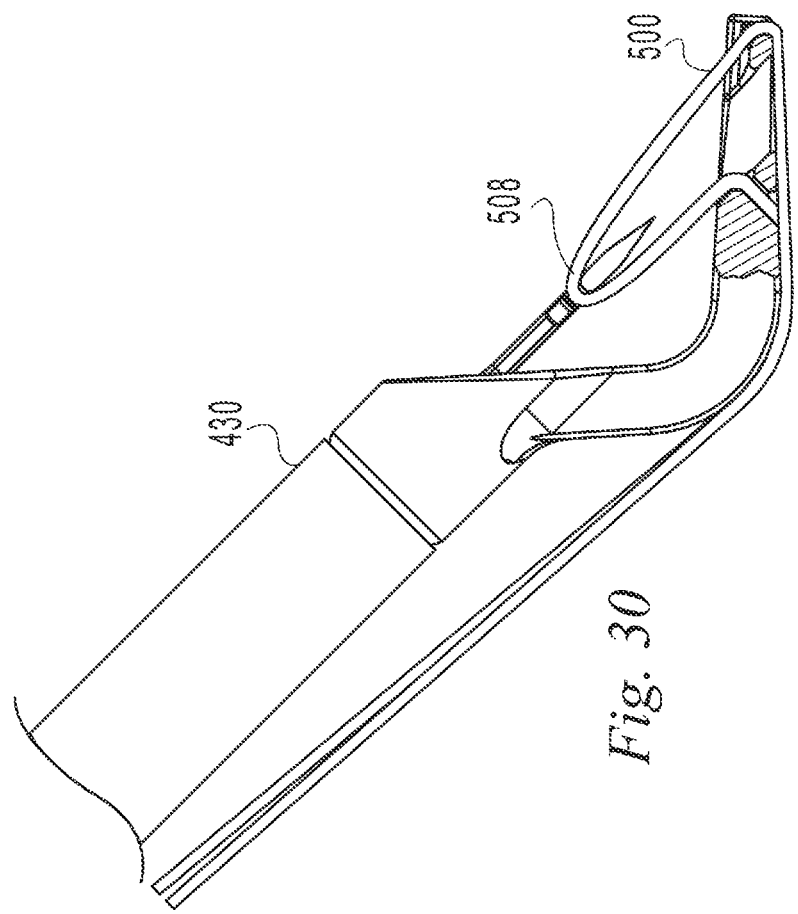

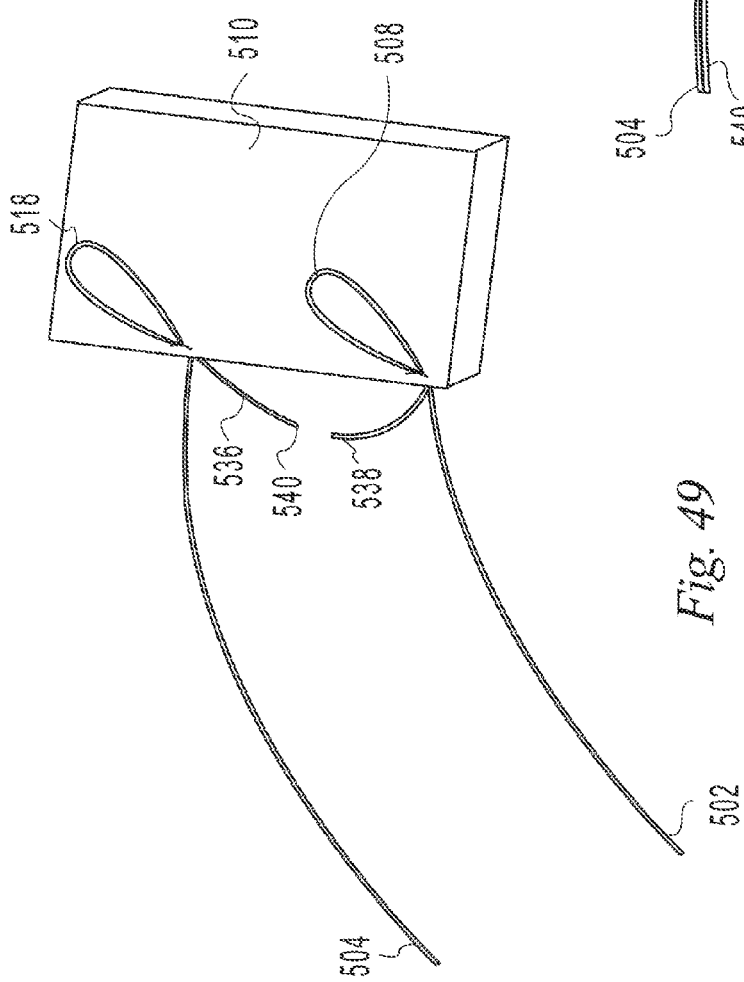
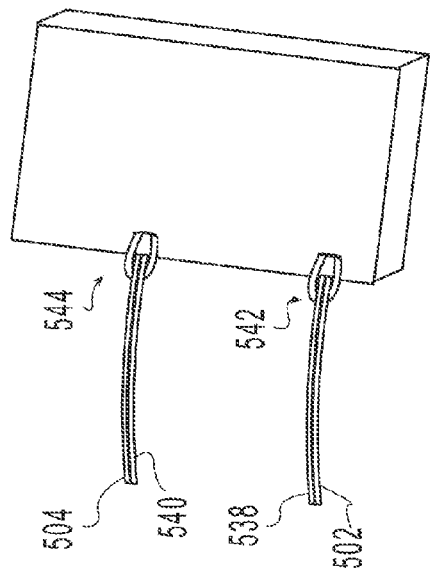
Fig. 49
Fig. 50

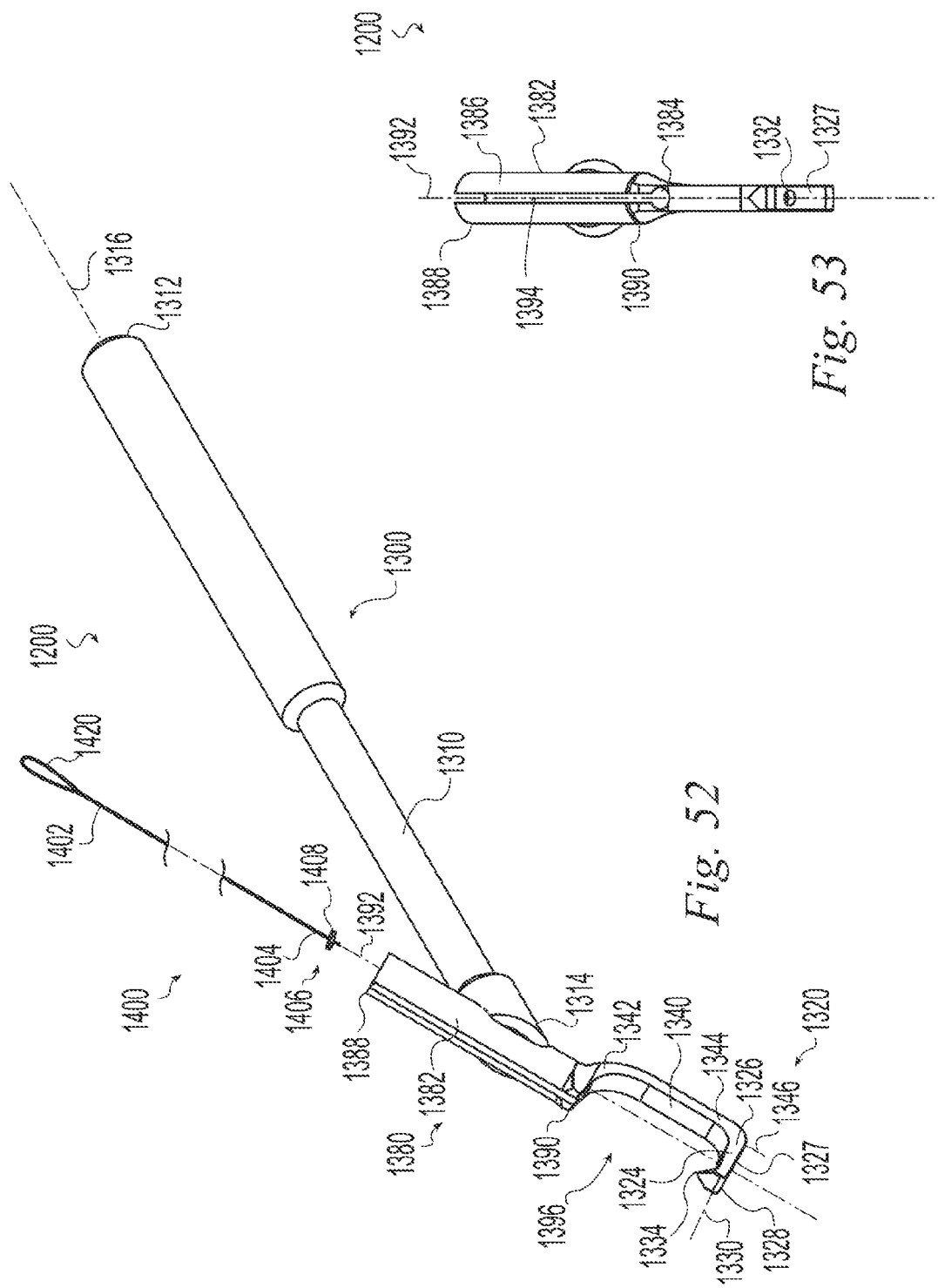

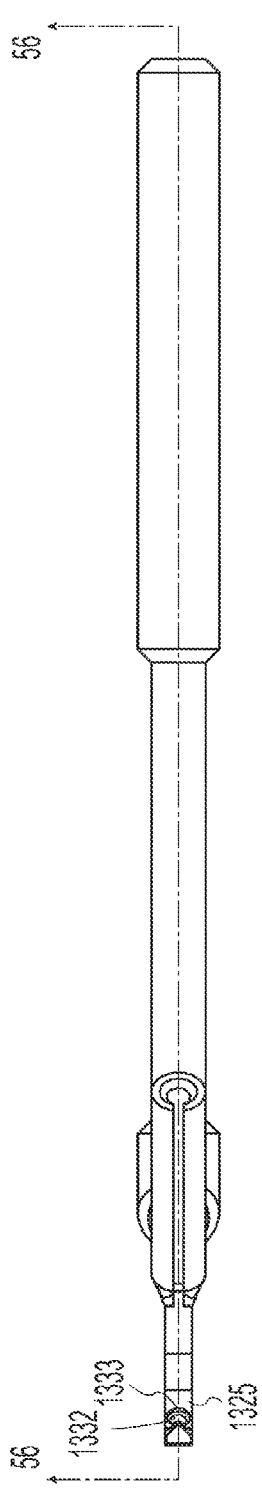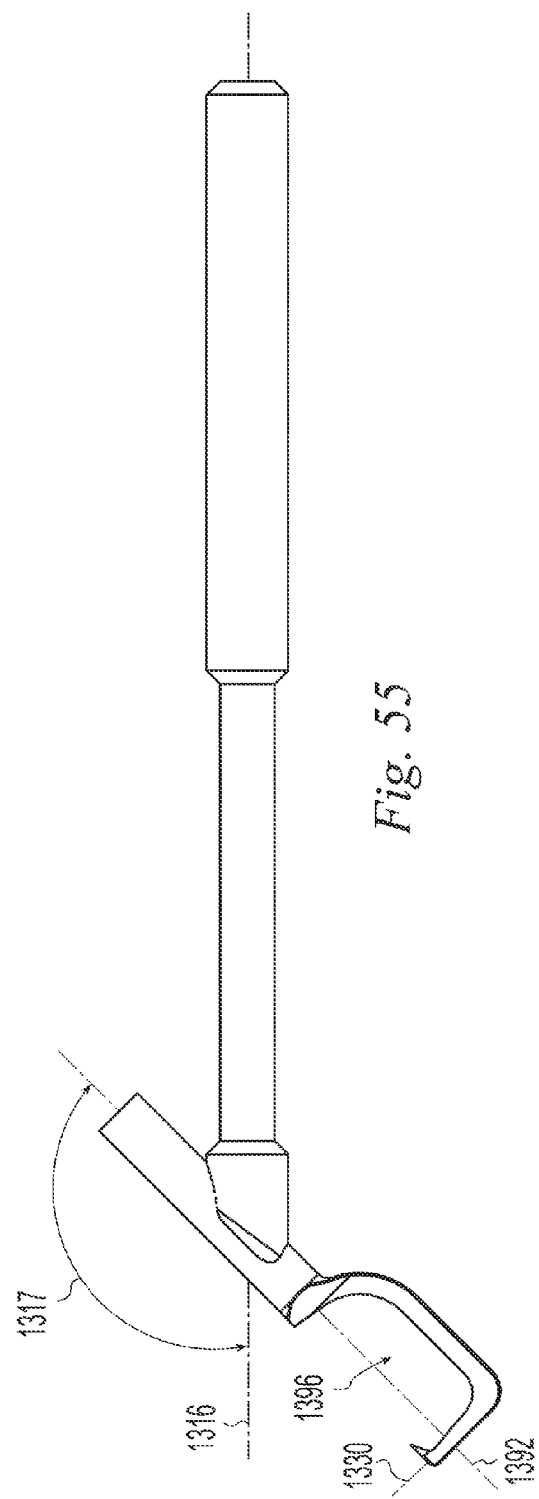
Fig. 54
Fig. 55

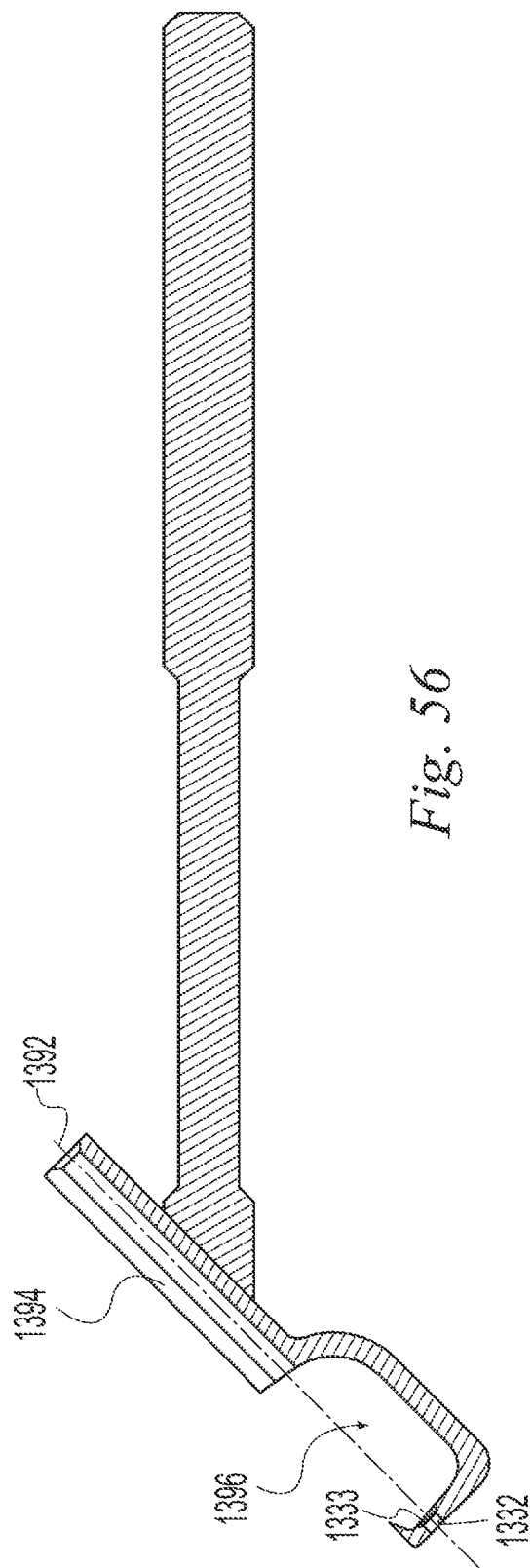

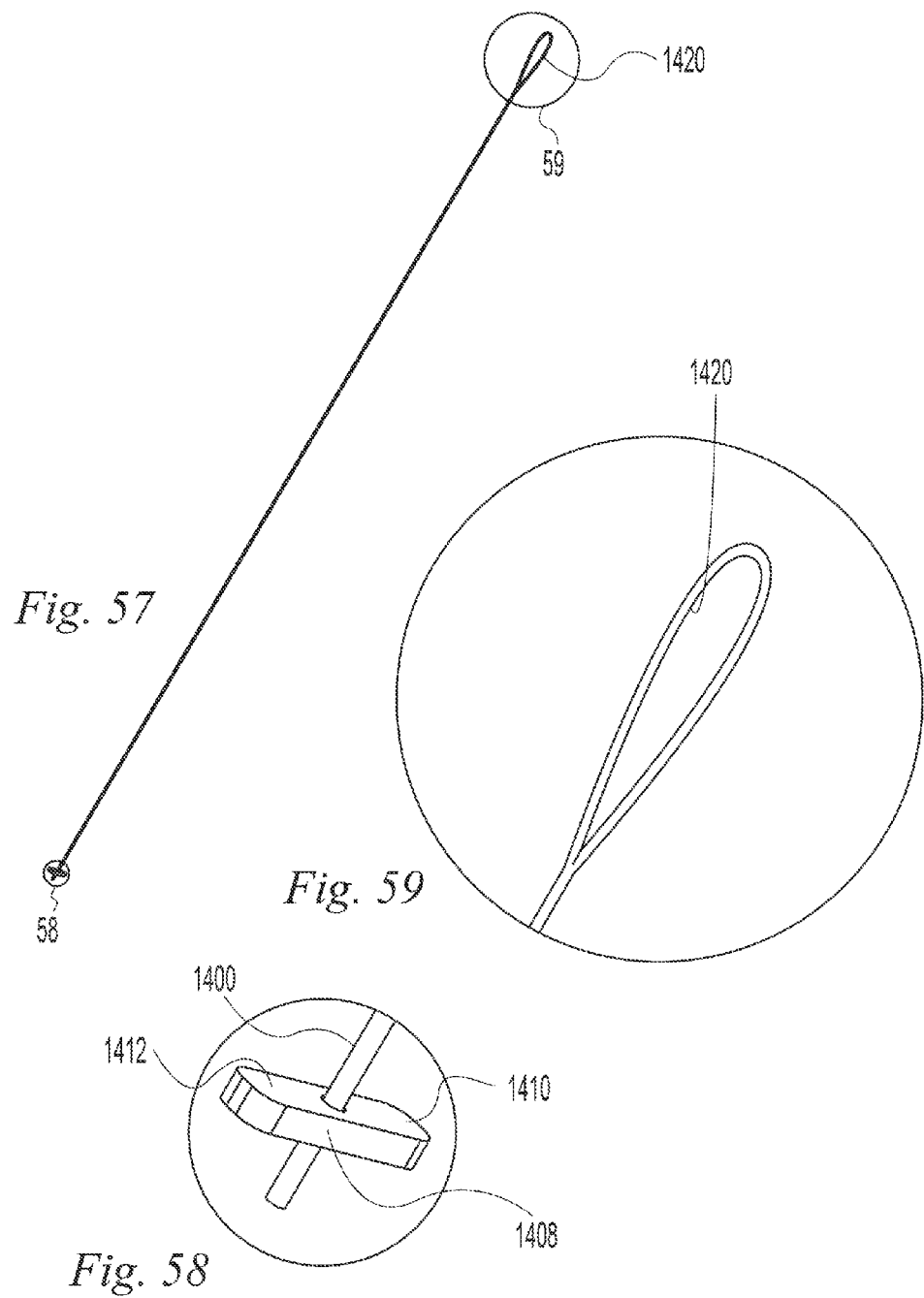

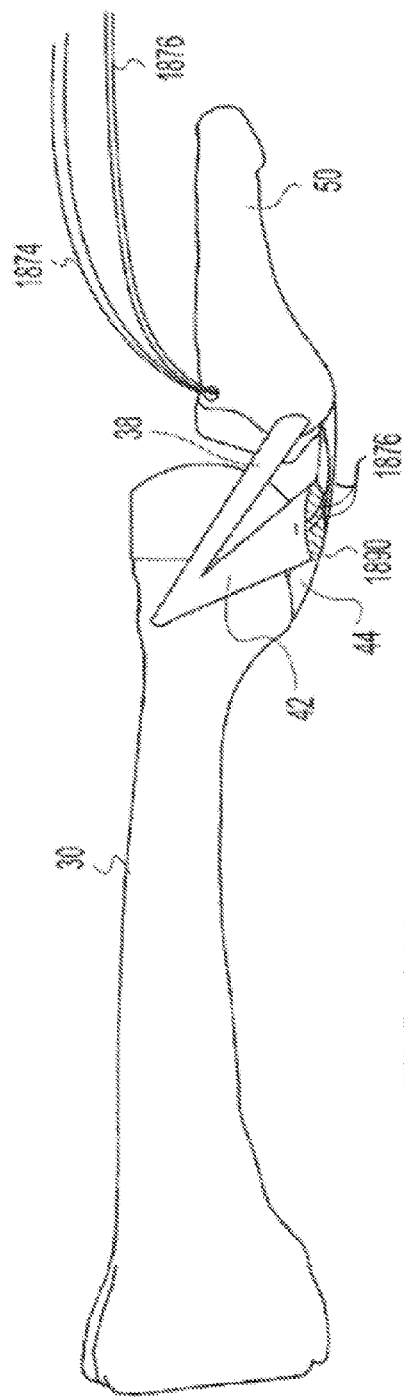
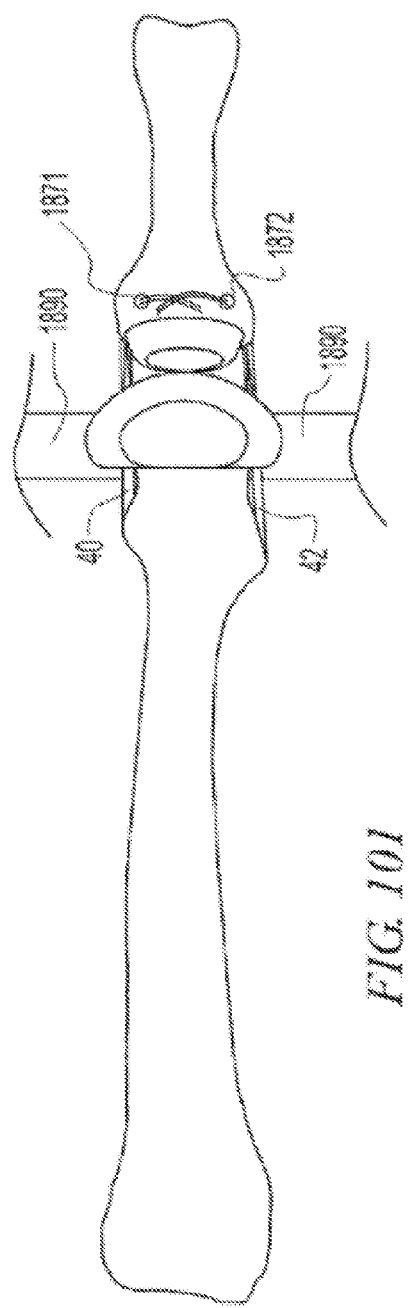

SOFT TISSUE REPAIR

CROSS-REFERENCE TO RELATED APPLICATIONS

This application is a divisional of U.S. patent application Ser. No. 13/623,837, filed Sep. 20, 2012, now issued as U.S. Pat. No. 8,882,834, which is continuation-in-part of U.S. patent application Ser. No. 13/527,424, filed Jun. 19, 2012, now issued as U.S. Pat. No. 9,357,997, and is also a continuation-in-part of U.S. patent application Ser. No. 13/527,765, filed Jun. 20, 2012, now issued as U.S. Pat. No. 8,801,727 both of which claim the benefit of U.S. Provisional Application No. 61/568,137, filed Dec. 7, 2011, U.S. Provisional Application No. 61/505,992, filed Jul. 8, 2011, U.S. Provisional Application No. 61/506,000, filed Jul. 8, 2011, and U.S. Provisional Application No. 61/506,004, filed Jul. 8, 2011. All of the cross-referenced non-provisional and provisional applications are hereby incorporated by reference.

FIELD OF THE INVENTION

The invention relates methods and instruments for repairing soft tissues of a skeletal joint such as for example of the foot or hand.

BACKGROUND

Various conditions may affect skeletal joints such as the elongation, shortening, or rupture of soft tissues associated with the joint. Repairs of the soft tissues of joints that are difficult to access have been neglected in the past.

SUMMARY

The present invention provides methods for repairing soft tissues associated with joints. In one aspect of the invention, a method of repairing soft tissue of a joint of a human extremity includes maintaining the metapodial bone intact, forming a bone tunnel through the proximal phalanx, passing a repair suture through the soft tissue to be repaired, passing the repair suture through the bone tunnel, and securing the suture.

In another aspect of the invention, the soft tissue to be repaired includes a volar ligament.

In another aspect of the invention, the soft tissue to be repaired includes a collateral ligament.

In another aspect of the invention, the soft tissue to be repaired includes a volar plate and a collateral ligament and a repair suture from each is passed through a common bone tunnel.

In another aspect of the invention, passing a suture through a bone tunnel includes positioning a receiver of a suture retriever at a first position adjacent the proximal phalanx, placing a first portion of the passing suture through the bone tunnel until the first portion of the passing suture is received by the receiver, retaining the first portion with the receiver, and moving the receiver away from the first position to advance the suture into the bone.

In another aspect of the invention, forming a bone tunnel includes providing a guide aligned with the suture receiver and guiding a cutter with the guide to form the bone tunnel prior to passing the suture through the bone tunnel.

In another aspect of the invention, passing a suture through soft tissue to be repaired includes positioning a distal portion of a suture passer volar to the soft tissue, extending a needle through the soft tissue and into an opening in the distal portion, and retracting the needle to retrieve a portion of the repair suture through the soft tissue.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is side elevation view of the human foot illustrating anatomic reference planes;

FIG. 2 is a dorsal view of the metatarsus and phalanx of the right second metatarsophalangeal joint of the human foot;

FIG. 3 is a medial view of the bones of FIG. 2;

FIG. 4 is a lateral view of the bones of FIG. 2;

FIG. 6 is an exploded perspective view of the suture passer of FIG. 5;

FIG. 7 is a front elevation view of a component of the suture passer of FIG. 5;

FIG. 8 is a is a side elevation view of the component of FIG. 7;

FIG. 12 is a sectional view taken along line 12-12 of FIG. 11;

FIG. 13 is a perspective view of a component of the suture passer of FIG. 5;

FIG. 14 is a side elevation view of the component of FIG. 13;

FIG. 15 is a bottom plan view of a component of the suture passer of FIG. 5;

FIG. 16 is a side elevation view of the component of FIG. 15;

FIG. 17 is a sectional view taken along line 17-17 of FIG. 16;

FIG. 19 is a partially sectioned side elevation view of the distal end of the suture passer of FIG. 5 illustrating a suture being loaded on the suture passer;

FIG. 20 is a top plan view of the distal end of the suture passer of FIG. 5 illustrating a suture being loaded on the suture passer;

FIG. 21 is a partially sectioned side elevation view of the distal end of the suture passer of FIG. 5 illustrating a suture being loaded on the suture passer;

FIG. 22 is a top plan view of the distal end of the suture passer of FIG. 5 illustrating a suture being loaded on the suture passer;

FIG. 23 is a partially sectioned side elevation view of the distal end of the suture passer of FIG. 5 illustrating a suture being loaded on the suture passer;

FIG. 24 is a top plan view of the distal end of the suture passer of FIG. 5 illustrating a suture being loaded on the suture passer;

FIG. 26 is a partially sectioned side elevation view of the distal end of the suture passer of FIG. 5 illustrating the operation of the suture passer;

FIG. 27 is a top plan view of the distal end of the suture passer of FIG. 5 illustrating the operation of the suture passer;

FIG. 28 is a partially sectioned side elevation view of the distal end of the suture passer of FIG. 5 illustrating the operation of the suture passer;

FIG. 29 is a top plan view of the distal end of the suture passer of FIG. 5 illustrating the operation of the suture passer;

FIG. 30 is a partially sectioned side elevation view of the distal end of the suture passer of FIG. 5 illustrating the operation of the suture passer;

FIGS. 32-50 are perspective views illustrating the suture passer of FIG. 5 in use to pass sutures through a material to create a variety of stitches.

FIG. 52 is an exploded perspective view of an illustrative example of a suture passer according to the present invention;

FIG. 53 is a front elevation view of a component of the suture passer of FIG. 52;

FIG. 54 is a top plan view of the component of FIG. 53;

FIG. 55 is a side elevation view of the component of FIG. 53;

FIG. 56 is a sectional view taken along line 56-56 of FIG. 54;

FIG. 57 is a perspective view of a component of the suture passer of FIG. 52;

FIG. 58 is an enlarged perspective view of the distal end of the component of FIG. 58;

FIG. 59 is an enlarged perspective view of the proximal end of the component of FIG. 58;

FIGS. 79-101 illustrate the suture passers of FIGS. 5 and 52 in use to repair soft tissues.

DESCRIPTION OF THE ILLUSTRATIVE EXAMPLES

Figure 5:
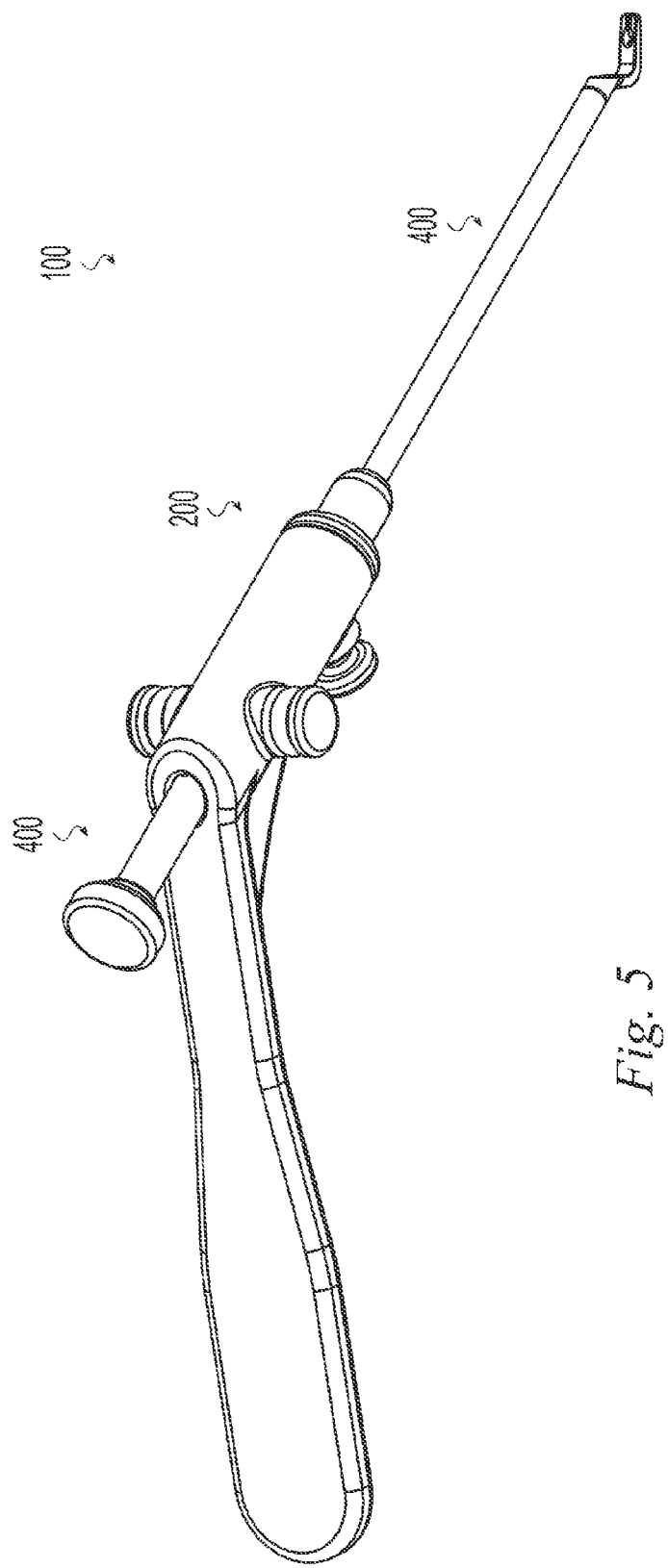
FIG. 5 is a perspective view of an illustrative example of a suture passer according to the present invention.
Figure 9:
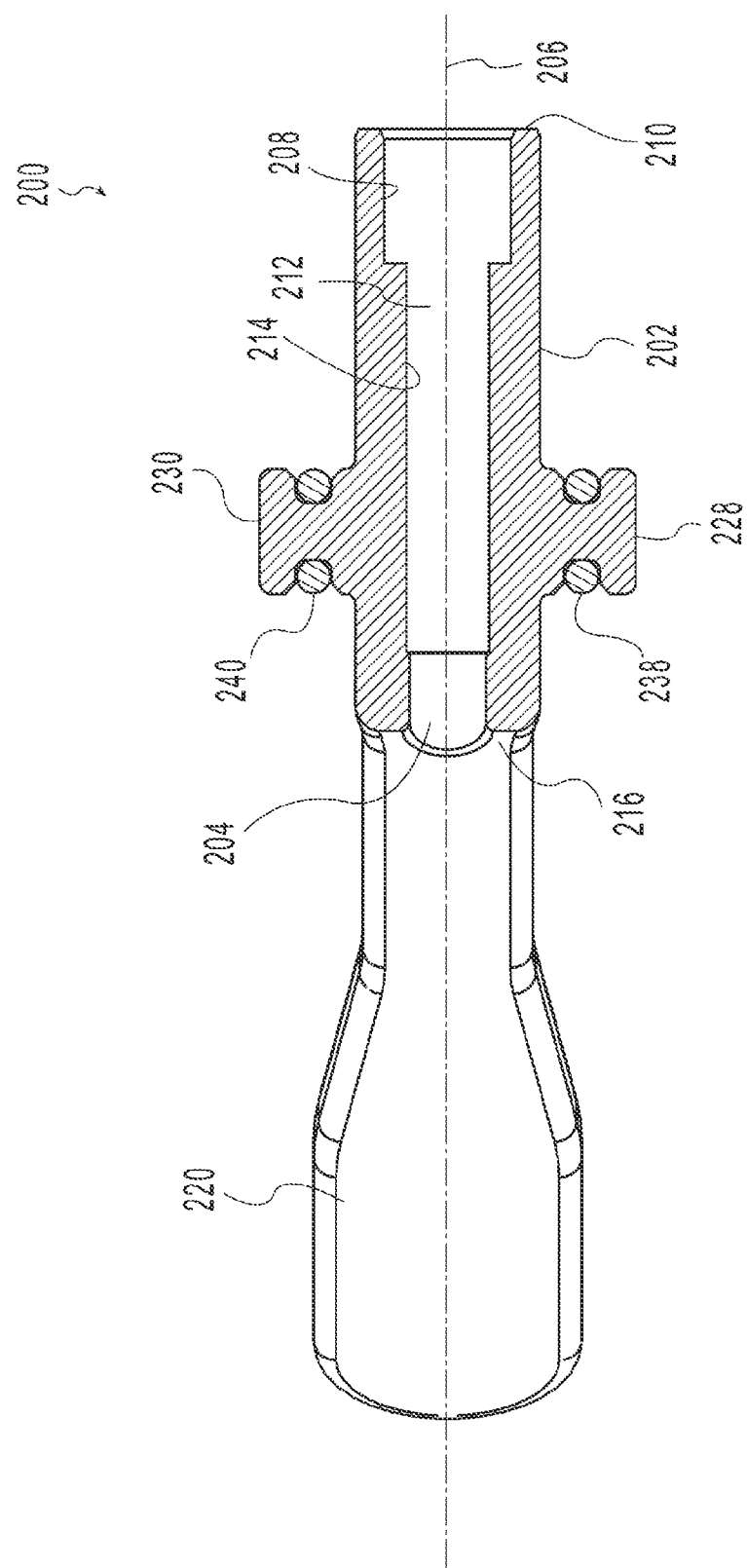
FIG. 9 is a sectional view taken along line 9-9 of FIG. 8.
Figure 10:
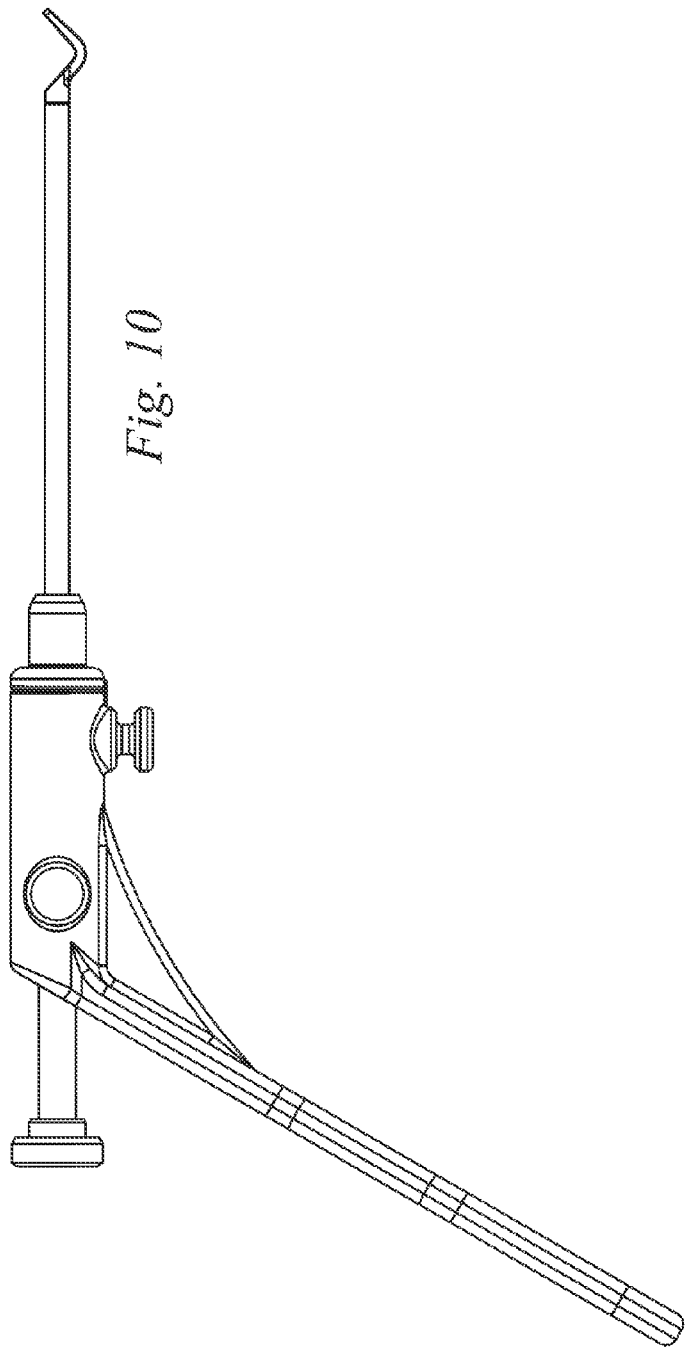
FIG. 10 is a side elevation view of the suture passer of FIG. 5.
Figure 11:
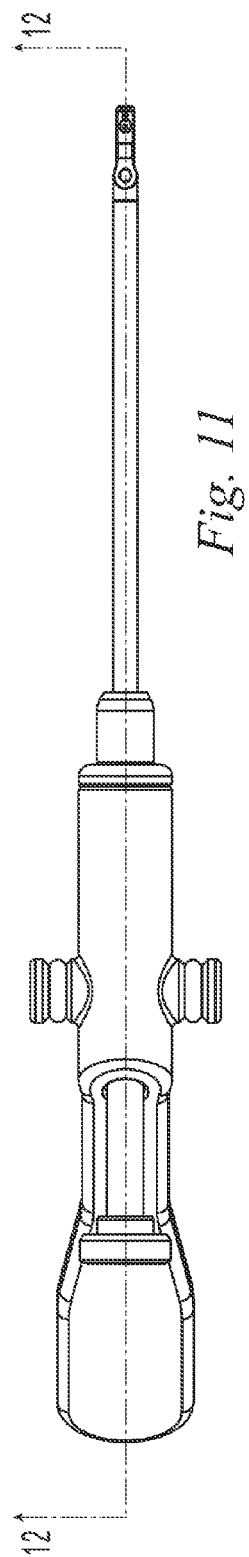
FIG. 11 is a top plan view of the suture passer of FIG. 5.
Figure 18A:
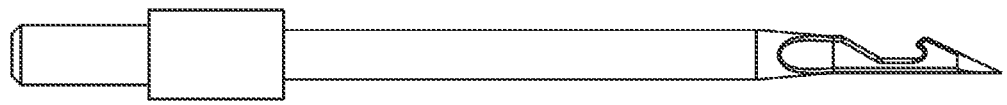
FIGS. 18A-G are bottom plan views of variations of the component of FIG. 15.
Figure 18B:
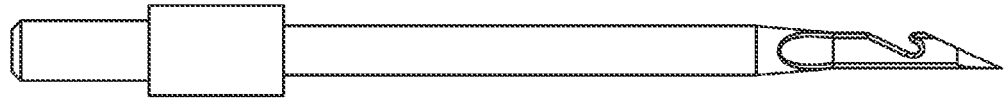
Figure 18C:
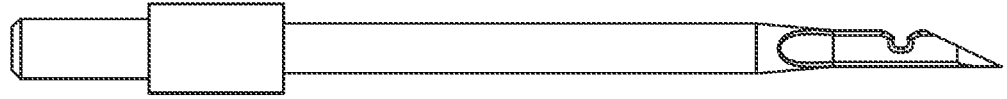
Figure 18D:
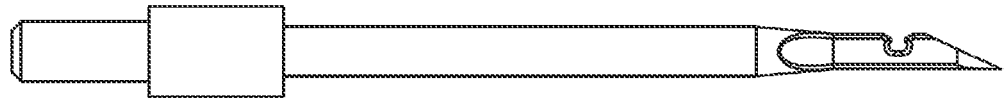
Figure 18E:
Figure 18F:
Figure 18G:
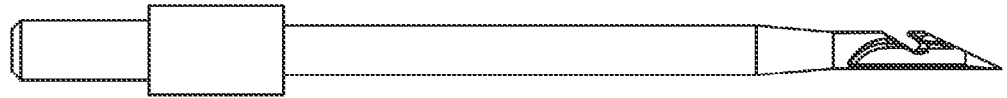

The following illustrative examples illustrate instruments and techniques for treating skeletal joints. Instruments and techniques according to the present invention may be used in conjunction with any skeletal joint but the illustrative examples are shown in a size and form most suitable for the joints of the hand and foot. The hand and foot have a similar structure. Each has a volar aspect. In the hand the volar, or palmar, aspect includes the palm of the hand and is the gripping side of the hand. In the foot the volar, or plantar, aspect is the sole of the foot and is the ground contacting surface during normal walking. Both the hand and foot have a dorsal aspect opposite the dorsal aspect. Both the hand and foot include long bones referred to as metapodial bones. In the hand, the metapodial bones may also be referred to as metacarpal bones. In the foot, the metapodial bones may also be referred to as metatarsal bones. Both the hand and foot include a plurality of phalanges that are the bones of the digits, the fingers and toes. In both the hand and foot, each of the most proximal phalanges forms a joint with a corresponding metapodial bone. This joint includes a volar plate or band of connective tissue on the volar side of the joint. The joint also includes collateral ligaments on the medial and lateral sides of the joint. A transverse ligament connects the heads of the metapodial bones. In the hand the joint is typically referred to as the metacarpophalangeal joint having a palmar plate on the palmar side, collateral ligaments medially and laterally, and a transverse ligament connecting the metacarpals. In the foot the joint is typically referred to as the metatarsophalangeal joint having a plantar plate on the plantar side, collateral ligaments medially and laterally including proper collateral ligaments and accessory collateral ligaments, and a transverse ligament also known as the transverse metatarsal ligament.

For convenience, the illustrative examples depict the use of instruments and techniques according to the present invention on metatarsophalangeal (MTP) joints of the human foot. The illustrative instruments and techniques are also suitable for use on metacarpophalangeal (MCP) joints of the human hand. To better orient the reader, the MTP joint and basic anatomic references are explained in more detail below.

FIG. 1 illustrates the anatomic planes of the foot that are used for reference in this application. The coronal plane 10 extends from the medial aspect 12 to the lateral aspect of the foot and from dorsal 14 to plantar 16 and divides the foot between the toes and heel. The sagittal plane 18 extends anterior 20 to posterior 22 and dorsal 14 to plantar 16 and divides the foot into medial and lateral halves. The transverse plane 24 extends anterior 20 to posterior 22 and medial to lateral parallel to the floor 26.

FIGS. 2-4 illustrate the metatarsus 30 and proximal phalanx 50 of the second MTP joint of the right foot. The medial and lateral epicondyles 32, 34, located on the medial-dorsal and lateral-dorsal aspects of the metatarsus 30 respectively, are the origins of the medial and lateral proper collateral ligaments (PCLs) 36, 38 and the medial and lateral accessory collateral ligaments (ACLs) 40, 42 of the MTP joint. The medial PCL inserts at the medial-plantar aspect 52 and the lateral PCL inserts at the lateral-plantar aspect 54 of the proximal phalanx 50. The ACLs fan out and insert into the plantar plate 44. The metatarsus includes a metatarsal head 46 having an articular surface 48 and the proximal phalanx includes a phalangeal head 56 having an articular surface 58. The metatarsus 30 further includes a longitudinal axis 60 extending lengthwise down the center of the bone.

The terms "suture" and "suture strand" are used herein to mean any strand or flexible member, natural or synthetic, able to be passed through material and useful in a surgical procedure. The term "material" is used herein to mean implants, grafts, fabric, tendon, ligament, fascia, skin, muscle, bone, and any other material it is desirable to cut or through which it is desirable to pass a suture. The term "transverse" is used herein to mean crossing as in non-parallel. The term "bight" is used herein to mean a bend or loop formed in the intermediate portion of a suture.

The illustrative examples of FIGS. 5-50 depict instruments and techniques to pass a suture through a material. The instruments and techniques may be used to pass a suture through any material, at surgical sites anywhere in a patient's body, and for any purpose. The instruments and techniques are particularly useful where access to confined spaces and the ability to pass a suture through difficult to penetrate materials are needed. For example, surgery on the hands and feet often involve working in confined spaces around small joints and tough connective tissues through which it may be desirable to pass a suture.

FIGS. 5-17 depict an illustrative example of a suture passer 100. The suture passer 100 includes a housing 200, a needle assembly 300, and a barrel assembly 400 mounted together and operable to translate the needle assembly 400 between a first, retracted position and a second, extended position to manipulate a suture strand.

The housing 200 includes a hollow receiver portion 202 having a hollow bore 204 with a longitudinal bore axis 206. An enlarged counter bore 208 (FIG. 9) is formed coaxial with the through bore 204 at a distal end 210 of the receiver 202. An intermediate portion 212 of the through bore 204 has flat side walls 214. A handle 220 extends downwardly and proximally from the receiver 202 and has a longitudinal handle axis 222. The handle axis 222 forms an angle 224 with the bore axis 206. The angle 224 is in the range of 90 to 180 degrees; preferably 100 to 140 degrees; more preferably 110 to 130 degrees. In the illustrative example of FIGS. 5-17, the angle 224 is 120 degrees. A gusset 226 extends between the handle 220 and the receiver 202 for strength. One or more knobs extend from the housing to provide suture strand anchor or routing points. In the illustrative example of FIGS. 5-17, first and second opposed side knobs 228, 230 and a downwardly projecting bottom knob 232 are mounted to the receiver 202. Each knob has a narrow waist 234 and an enlarged head 236 as shown with reference to the bottom knob 232. A suture strand may be wrapped or tied around the waist 234 to secure or route the suture. O-rings 238, 240 are provided on the side knobs 228, 230 to grip a wrapped suture to facilitate securing and removing a suture strand. As a suture is wrapped around the side knobs 228, 230, it wedges between the resilient O-ring 238, 240 and knob compressing the O-ring. The pressure of the O-ring pressing the suture strand against the knob as well as the deformation of the O-ring around the suture strand temporarily secures the suture.

The needle assembly 300 includes a piston 310, a stem 330, a needle 350, and a button 390. The piston 310 has a generally cylindrical body 312 with a longitudinal axis 316 extending from a proximal end 318 to a distal end 320. A flange 322 extends radially outwardly from the body 312 near the distal end 320. The flange has opposed flattened sides 324. A bore 326 (FIG. 12) is formed coaxially in the piston 310 at the distal end of the body 312. The stem 330 includes an elongated hollow cylinder 332 having an outer diameter and an inner bore 334 defining a longitudinal axis 336 extending from a proximal end 338 to a distal end 340. The needle 350 is a generally cylindrical member having a shank 352 with an outer diameter defining a longitudinal axis 354 extending from a proximal end 356 to a distal tip 358. A flange 360 extends radially outwardly from the shank 352 at a position intermediate the proximal and distal ends.

The needle 350 will be described in greater detail below. The button 390 has a generally cylindrical body with a longitudinal axis 391 extending from a proximal end 393 to a distal end 395. A bore 398 (FIG. 12) is formed coaxially in the button 390 at the distal end 395 of the body. The proximal portion of the needle shank 352 fits within the inner bore 334 of the stem at its distal end 340. The stem outer diameter, near its proximal end 338, fits within the bore 326 of the piston 310. The outer diameter of the piston 310 fits within the bore 204 of the receiver 202 in linear sliding relationship. The flat sides 324 of the piston engage the flat side walls 214 of the bore 204 to prevent the needle assembly from rotating relative to the receiver 202. The piston flange 322 abuts the proximal end of the intermediate portion 212 of the bore 204 of the receiver 202 to provide a stop to needle assembly proximal translation relative to the receiver 202. The outer diameter of the piston 310, near its proximal end, fits within the bore 398 of the button 390 and the button 390 abuts a proximal end 216 of the receiver to provide a stop to needle assembly distal translation relative to the receiver 202. The joints between the button 390 and piston 310, the piston 310 and the stem 330, and stem 330 and needle 350 are secured by pressing, gluing, pinning, welding, or other suitable securing means. Alternatively, two or more of these components or various combinations of them may be made as a single piece.

The barrel assembly 400 includes a barrel bushing 410, a barrel 430, and a foot 450. The bushing 410 has a generally cylindrical body 412 having a through bore 414 with a longitudinal axis 416 extending from a proximal end 418 to a distal end 420. A flange 422 extends radially outwardly from the body 412 at a position intermediate the proximal and distal ends. An enlarged counter bore 424 (FIG. 12) is formed coaxial with the through bore 414 at the distal end 420 of the body 412. The barrel 430 includes an elongated hollow cylinder 432 having an outer diameter and an inner bore 434 defining a longitudinal axis 436 extending from a proximal end 438 to a distal end 440. The foot 450 is a generally hook-shaped member having a hollow post 452 having an outer diameter and an inner bore 454 defining a longitudinal axis 456 extending from a proximal end 458 of the cylinder to a distal end 460 of the foot 450. The foot will be described in greater detail below. The foot post 452 outer diameter fits within the inner bore 434 of the barrel at its distal end 440. The barrel 430 outer diameter, near its proximal end 438, fits within the counter bore 424 of the bushing. A coiled compression spring 250 fits coaxially over the needle assembly 300 within the bore 204 of the receiver 202 and rests against the distal end of the piston flange 322. The barrel assembly 400 fits coaxially over the needle assembly 300 and the outer diameter of the bushing 410, near its proximal end 418, fits within the counter bore 208 of the receiver 202 and is pressed proximally until the flange 422 abuts the receiver distal end 210. The proximal end of the bushing retains the spring 250 within the bore 204. The joints between the foot 450 and barrel 430, the barrel 430 and bushing 410, and the bushing 410 and receiver 202 are secured by pressing, gluing, pinning, welding, or other suitable securing means. Alternatively, the bushing, barrel, foot, or any combination of them may be made as a single piece. Pressing the button 390 distally translates the needle assembly from a first, proximal, retracted position distally along the needle axis 354 compressing the spring 250 and extending the needle 350 through the foot 450 to a second, distal, extended position. Releasing the button 390 allows the spring 250 to expand and bias the needle assembly 300 back toward the first position. The needle assembly 300 of the illustrative example of FIGS. 5-17 is a linear arrangement mounted for linear, coaxial translation in the housing 200 and barrel assembly 400 with the needle projecting straight through the foot to increase rigidity and power facilitating driving the needle 350 through difficult to penetrate materials and access confined spaces. The barrel 430 may have a circular, polygonal, or any other cross sectional shape.

FIGS. 13 and 14 illustrate the foot 450 of the illustrative example of FIGS. 5-17 in greater detail. The hooked portion of the foot 450 includes an elbow 462 having a first, proximal portion 464 extending distally from the post 452 along a proximal portion axis 465 diverging from the bore axis 456 at a first angle 466 relative to the bore axis 456. A second, distal portion 468 extends distally from the first portion 464 along a distal portion axis 469 converging toward the bore axis 456 at a second angle 470 relative to the bore axis 456. The first and second angles 466, 470 are chosen to allow the foot to extend into a confined space, for example behind material such as a portion of soft tissue such as a tendon or ligament, and position the receiver 202 so as not to obstruct the users view of the foot and needle. The first angle 466 is in the range of 0 to 180 degrees; preferably 0 to 90 degrees; more preferably 25 to 55 degrees; more preferably 35 to 45 degrees. In the illustrative example of FIG. 14, the first angle 466 is approximately 42 degrees. The second angle 470 is in the range of 0 to 90 degrees; preferably 25 to 55 degrees; more preferably 35 to 45 degrees. In the illustrative example of FIGS. 13 and 14, the second angle 470 is also approximately 42 degrees. An eye 472 is formed through the second portion 468, from a proximal facing surface 474 to a distal facing surface 476, coaxial with the bore axis 456 for receiving the distal end of the needle 350 when the needle is in the second position. A hole 478 defining a hole axis 480 extends through the second portion 468 from the distal surface 476 and intersecting the eye 472. The hole 478 permits passing a suture strand from the distal surface 476 of the second portion 468 to the eye 472. The hole axis 480 forms an angle 482 relative to the bore axis 456. The angle 482 is between parallel to the proximal facing surface 474 of the second portion 468 and parallel to the distal facing surface of the first portion 464; preferably in the range of 45 to 135 degrees; more preferably 45 to 90 degrees. In the illustrative example of FIGS. 13 and 14, the hole angle 482 is approximately 90 degrees relative to the bore axis 456. A groove 484 is formed in the proximal surface 474 of the second portion 468 communicating from the eye 472 to the distal end 460. A notch 486 is formed through the distal end 460 from the proximal surface 474 to the distal surface 476 and communicating with the groove 484. The groove 484 and notch 486 are sized to receive a suture strand and retain the strand on the distal end of the foot 450. The proximal surface 474 of the second portion 468 of the foot 450 provides a supporting platform for material through which the needle 350 is passed. The eye 472 allows the needle 350 to penetrate all the way through the material and intercept a suture strand extending from the hole 478 to the groove 484.

FIGS. 15-17 illustrate the needle 350 of the illustrative example of FIGS. 5-17 in greater detail. A narrowed shaft 362 extends between the shank 352 and a sharp tip 364 at the distal end of the needle. A shoulder 366 defines the transition from the shank 352 to the shaft 362. The shaft 362 is generally rectangular in cross section with a top 368, a bottom 370, and opposing sides 372, 374. The corners 376 are rounded. The shaft 362 has a height 378 between the top 368 and bottom 370 and a width 380 between the sides 372, 374. Both the height 378 and width 380 of the shaft are narrower than the shank 352. The width 380 of the shaft 362 is greater than its height 378. The ratio of the width 380 to the height 378 is in the range of 1 to 3; preferably 2 to 3. In the illustrative example of FIGS. 15-17 the ratio is approximately 2.3. The distal end of the shaft is tapered in the width dimension from the full width to the tip 364. In the illustrative example of FIGS. 15-17, the shaft is tapered on a single side in the width dimension to form a single-sided bevel 382. The distal end of the shaft is tapered in the height dimension from the full height to the tip 364. In the illustrative example of FIGS. 15-17, the shaft is tapered on opposite sides in the height dimension to form a chisel portion 384. A notch 386 is formed in the side of the shaft 362 through the shaft 362 from the top 368 to the bottom 370. The notch 386 has an opening width 388 measured parallel to the needle axis 354, a depth 389 measured perpendicular to the needle axis 354, and a notch axis 392 forming an angle 394 to the needle axis 354. In the illustrative example of FIGS. 15-17, the notch has parallel side walls 396, 398 that are parallel to the axis 392. The notch width 388, depth 389, and angle 394 are selected to optimize the ability of the needle 350 to capture and retain a suture strand while avoiding snagging other material through which the needle 350 passes. FIGS. 18A-18G illustrate a variety of needle designs having varying notch width, depth, and angle. The present inventors have determined that the balance between capturing and retaining a suture strand and avoiding snagging is optimized, in the case of a suture strand with a diameter D, when the width of the notch is in the range of 0.9D to 2D. A notch width of 0.9D creates a press fit depending on the resilient nature of the suture strand. Preferably, the notch width is in the range of 1D to 1.5D. Similarly, the notch depth is optimized when the depth is in the range of 0.75D to 3D. A notch depth of 0.75D captures the suture but leaves a portion of the suture projecting from the notch. Preferably, the depth is in the range of 1D to 2D. The notch angle is in the range of 30 to 90 degrees; preferably 35 to 55 degrees. In the illustrative example of FIGS. 15-17, the notch was optimized for a USP#2-0 suture having a diameter in the range of 0.300-0.339 mm and has a width of 0.30 mm and a depth of 0.46 mm and an angle of 45 degrees. The notch opens toward the side of the needle 350 and suture passer 100. The bevel 382 leads from the tip 364 of the needle along the narrow side of the needle shaft 362 toward the opening of the notch 386. The needle may be sized to capture and pass one or more suture strands.

Figure 25:
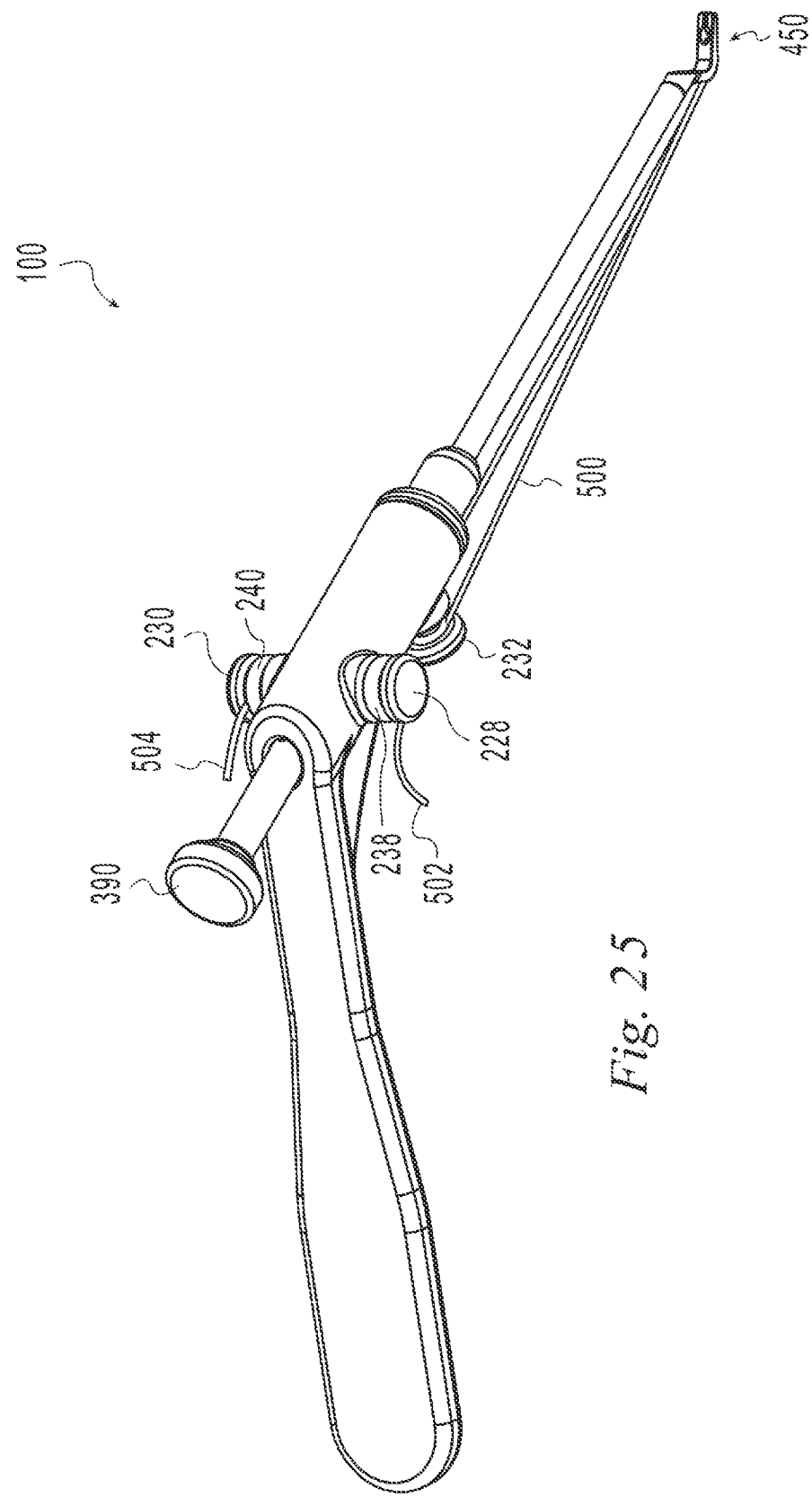
FIG. 25 is a perspective view of the suture passer of FIG. 5 illustrating a suture being loaded on the suture passer.
Figure 31:
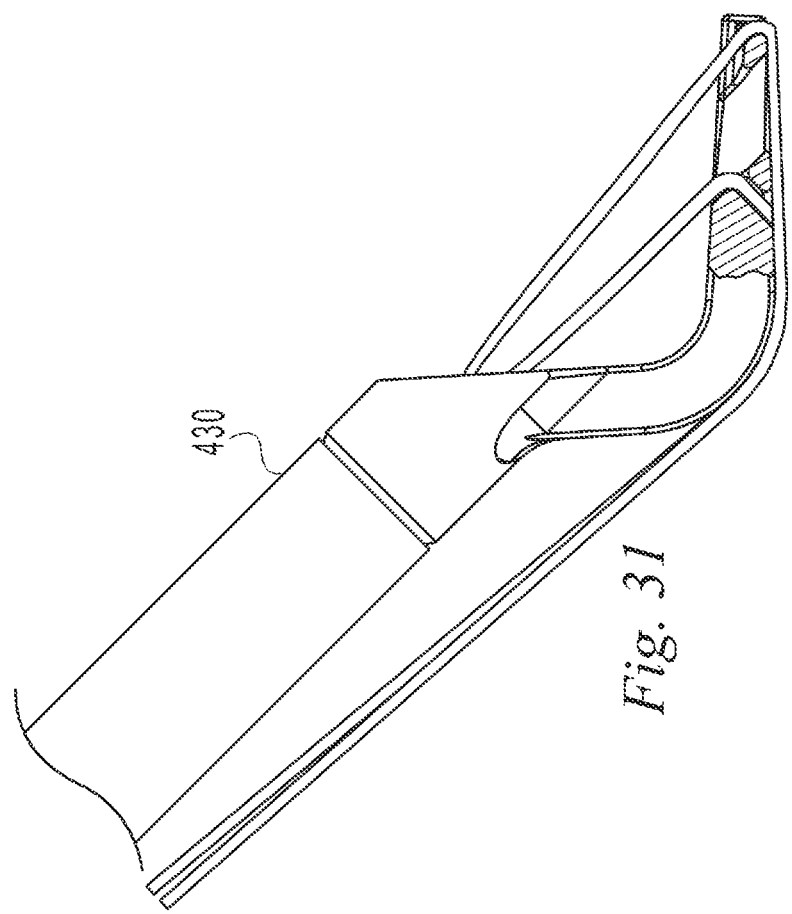
FIG. 31 is a partially sectioned side elevation view of the distal end of the suture passer of FIG. 5 illustrating the operation of the suture passer.

FIGS. 19-25 illustrate loading a suture strand 500, having a first end 502 and a second end 504 into the suture passer 100 of FIGS. 5-17. A first end 502 of the suture strand 500 is inserted through the hole 478 in the foot 450 from the distal surface 476 toward the eye 472 and extended past the proximal surface 474 as shown in FIGS. 19 and 20. The first end 502 of the suture strand is pulled distally to place the suture strand 500 in the groove 484 as shown in FIGS. 21 and 22. The suture strand 500 is wrapped over the distal end 460 in the notch 486 and pulled proximally over the distal surface 476 of the second portion of the foot 450 as shown in FIGS. 23 and 24. The ends 502, 504 of the suture strand are wrapped around the side knobs 228 and 230 and retained by the O-rings 238, 240. In the example of FIG. 25, the suture strand ends are routed proximally to the bottom knob 232 wrapped part-way around the proximal side of the knob 232 and secured on the side knob opposite the side on which the end was routed such that the suture strand is maintained near the center of the suture passer 100 and better retained on the foot 450.

FIGS. 26-31 illustrate the operation of the suture passer 100. When the button 390 is pressed distally, the needle assembly 300 moves distally relative to the housing and barrel assembly along the straight-line motion axis 506 of the suture passer which is coaxial with the needle axis 354 and foot bore axis 456. As the needle 350 approaches the suture strand 500, the bevel 382 contacts the suture strand 500 and wedges it sideways increasing the tension in the suture as shown in FIGS. 26 and 27. Further advancement of the needle 350 moves the notch 386 toward alignment with the suture strand 500 until the tension in the suture causes the suture 500 to move into the notch 386 as shown in FIGS. 28 and 29. Releasing pressure on button 390 allows the spring 250 to bias the needle assembly proximally. Depending on the resilience of the suture 500 and how tightly it is secured to the knobs 228, 230, the needle may or may not be able to retract. By releasing one or both ends 502, 504 of the suture 500, the suture ends can move toward the foot 450 and allow the needle to retract and pull a bight 508 of suture 500 proximally toward the barrel 430 as shown in FIG. 30. Further retraction of the needle 350 pulls the bight 508 into the barrel 430 (FIG. 31) trapping the bight 508 between the needle 350 and barrel bore 434. To release the bight 508, the button 390 is pressed to advance the needle 350 out of the barrel 430.

Figure 32:
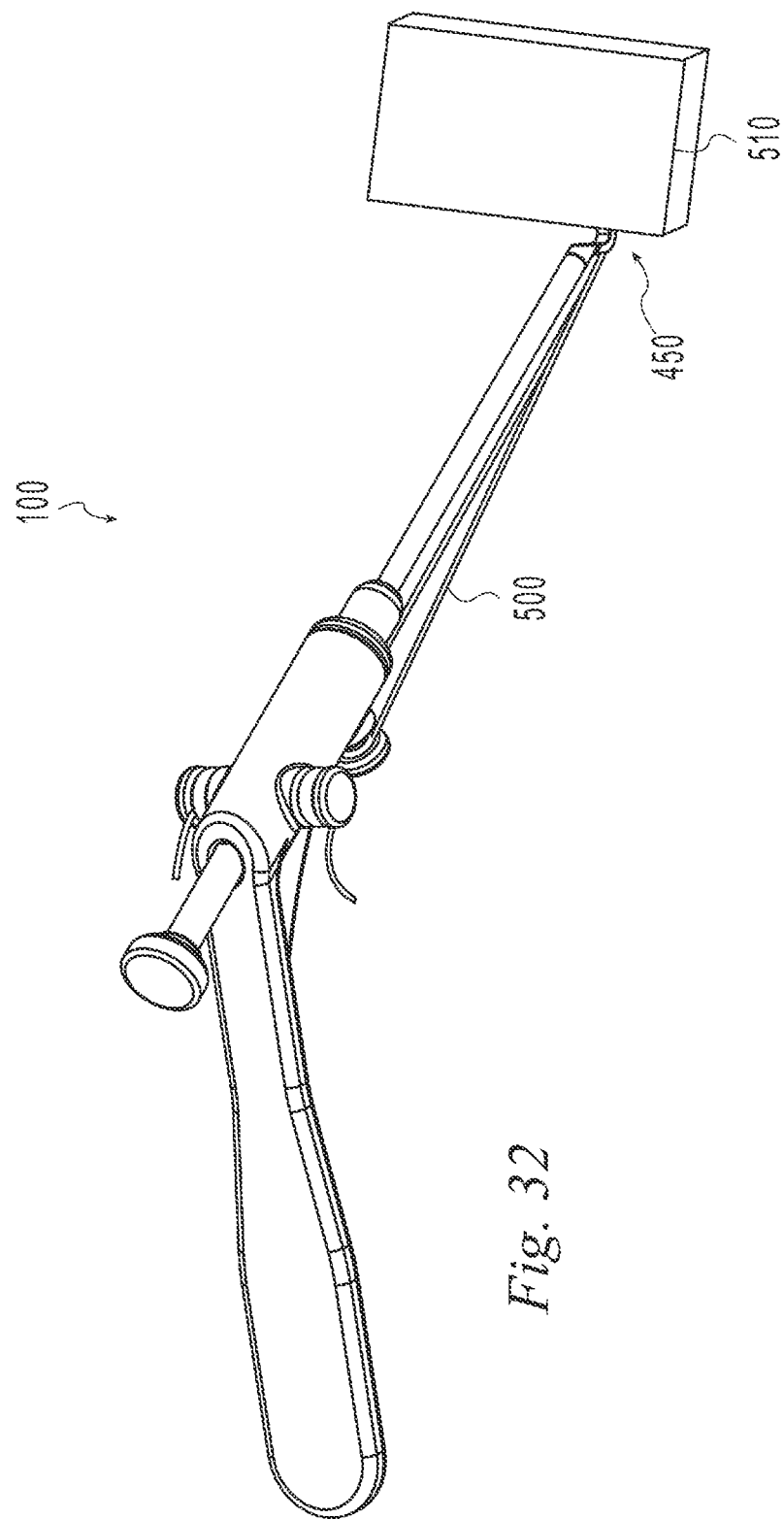
Figure 33:
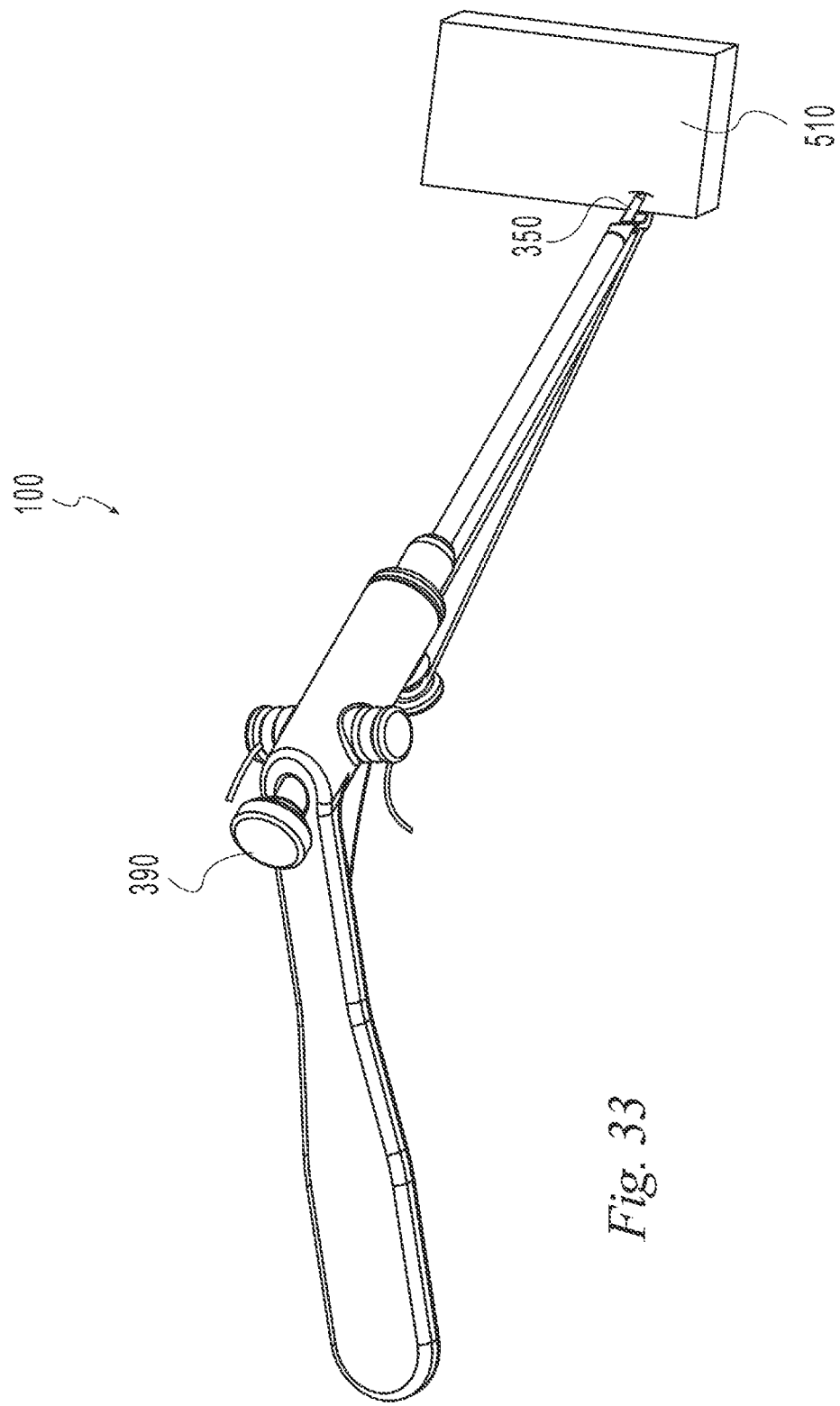
Figure 34:
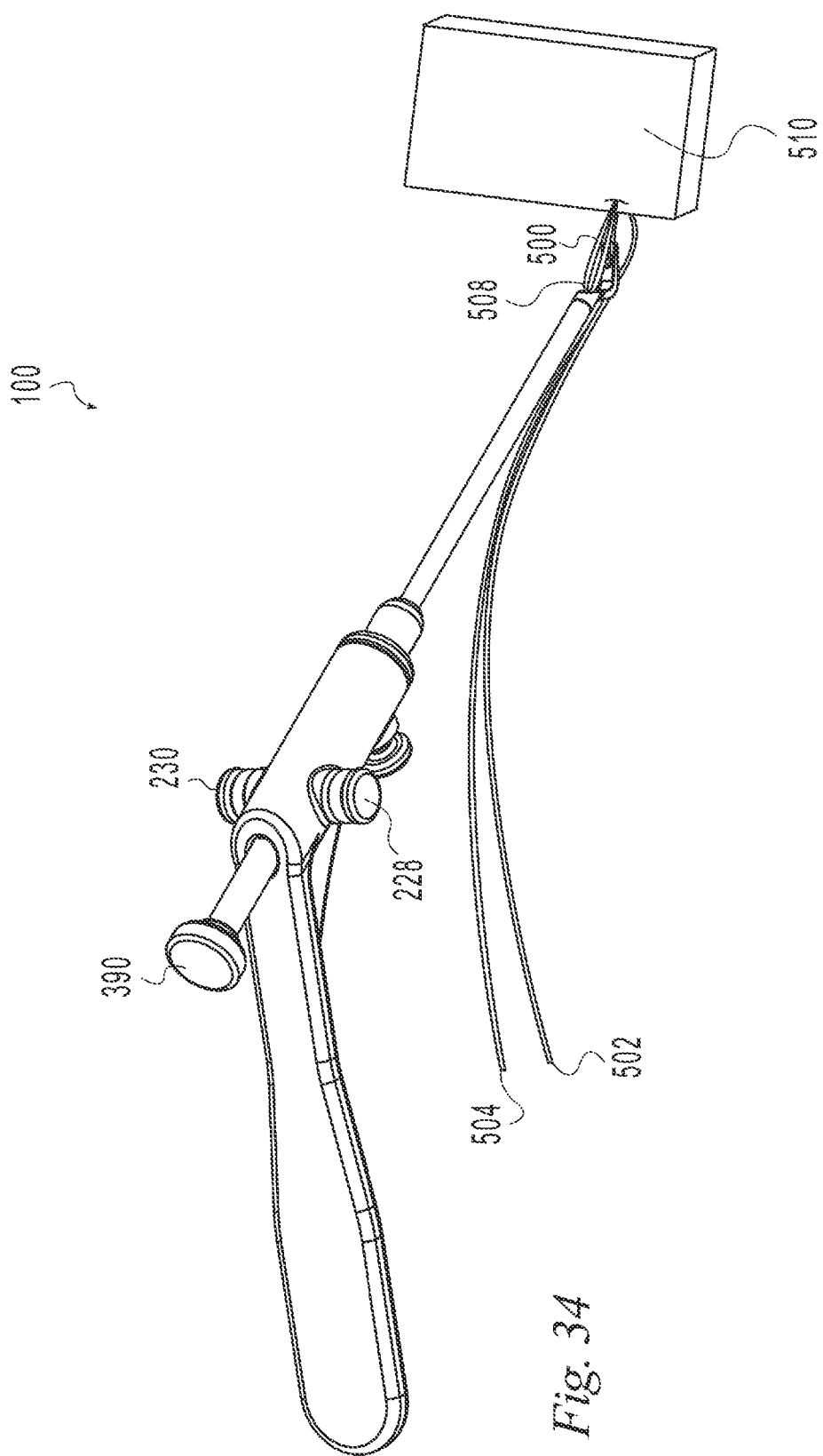
Figure 35:
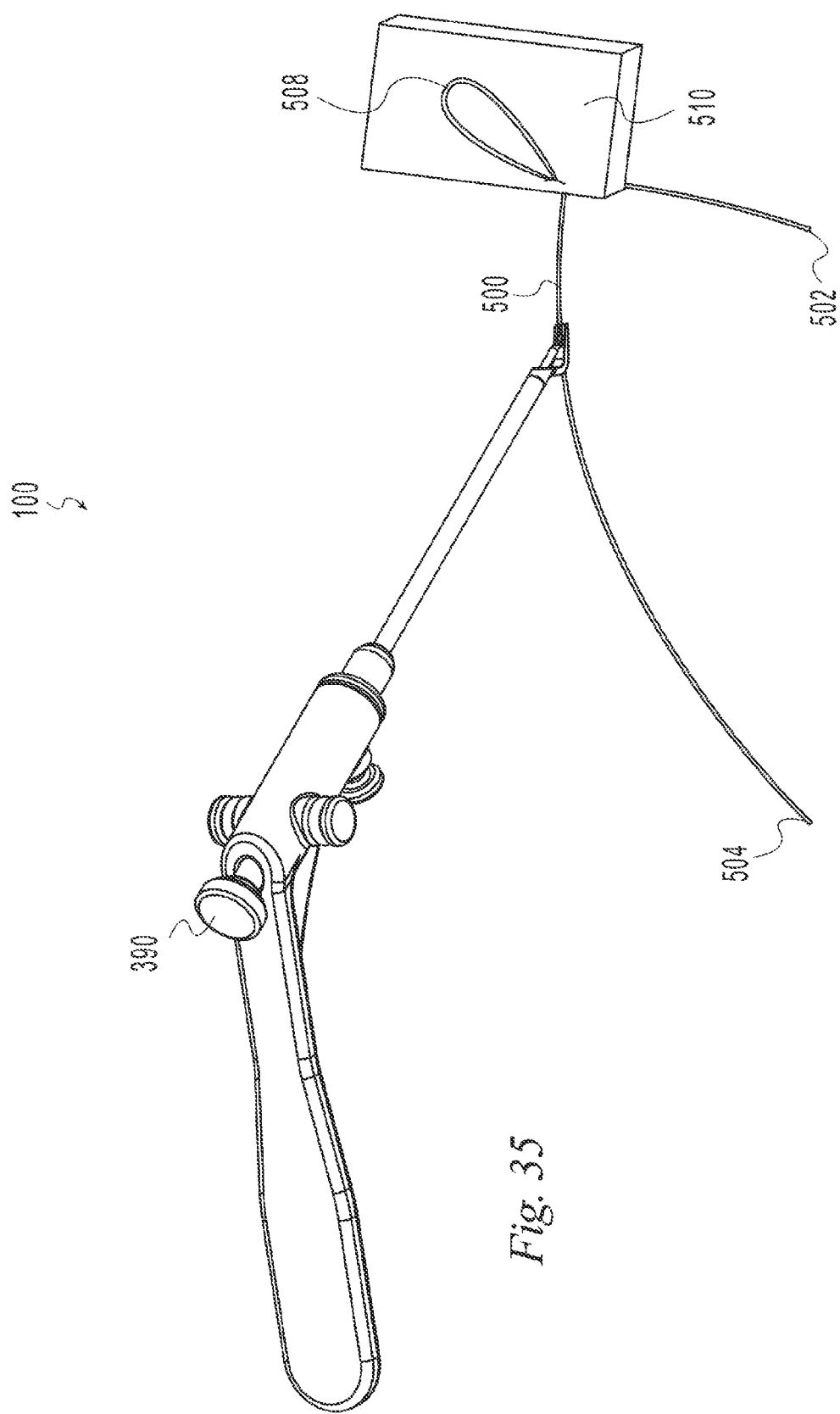
Figure 36:
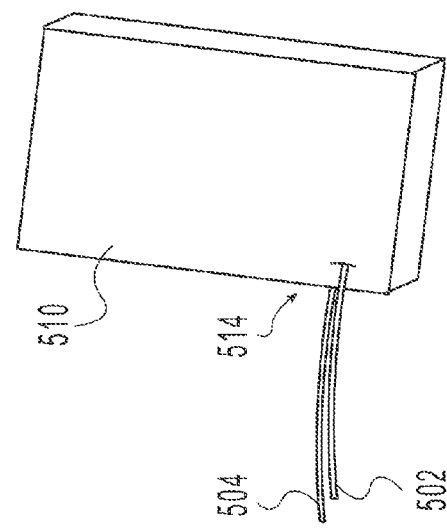
Figure 37:
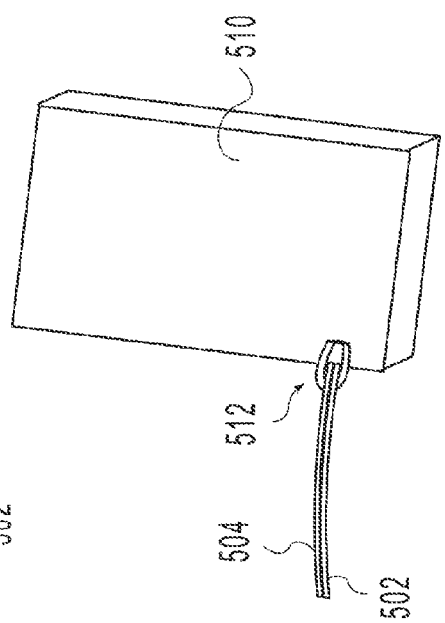

FIGS. 32-50 depict examples of the illustrative suture passer 100 in use to pass sutures through a material to create a variety of stitches. Referring to FIG. 32, the suture passer has been loaded as described relative to FIGS. 19-25. The foot 450 is positioned adjacent material 510 through which it is desired to pass the suture 500. The second portion 468 of the foot is positioned behind the material 510 with the proximal surface 474 supporting the material 510. Referring to FIG. 33, the button 390 is pressed to advance the needle 350 through the material 510 and capture the suture 500 in the eye 472 of the foot 450. Referring to FIG. 34, the button 390 has been released and the suture ends 502 and 504 have been freed from the knobs 228, 230 and allowed to move distally so that the needle 350 has retracted and pulled a bight 508 of suture 500 through the material 510. Referring to FIG. 35, the button 390 has been pressed to release the bight 508 and the first end 502 has been allowed to drop free from the passer 100. Referring to FIGS. 36 and 37, the second end 504 has been removed from the foot 450 by pulling the passer 100 proximally away from the bight or by pulling the suture 500 distally away from the foot 450. The suture ends 502, 504 have been passed through the bight 508 and pulled to form a stitch in the form of a hitch 512.

Figure 38:
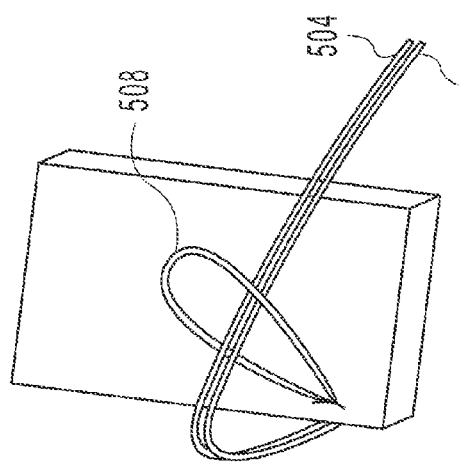

Referring to FIG. 38, instead of pulling the ends 502, 504 through the bight 508, the first end 502 has been pulled through the material 510 by pulling on one side of the bight 508 to form a simple stitch 514.

Figure 39:
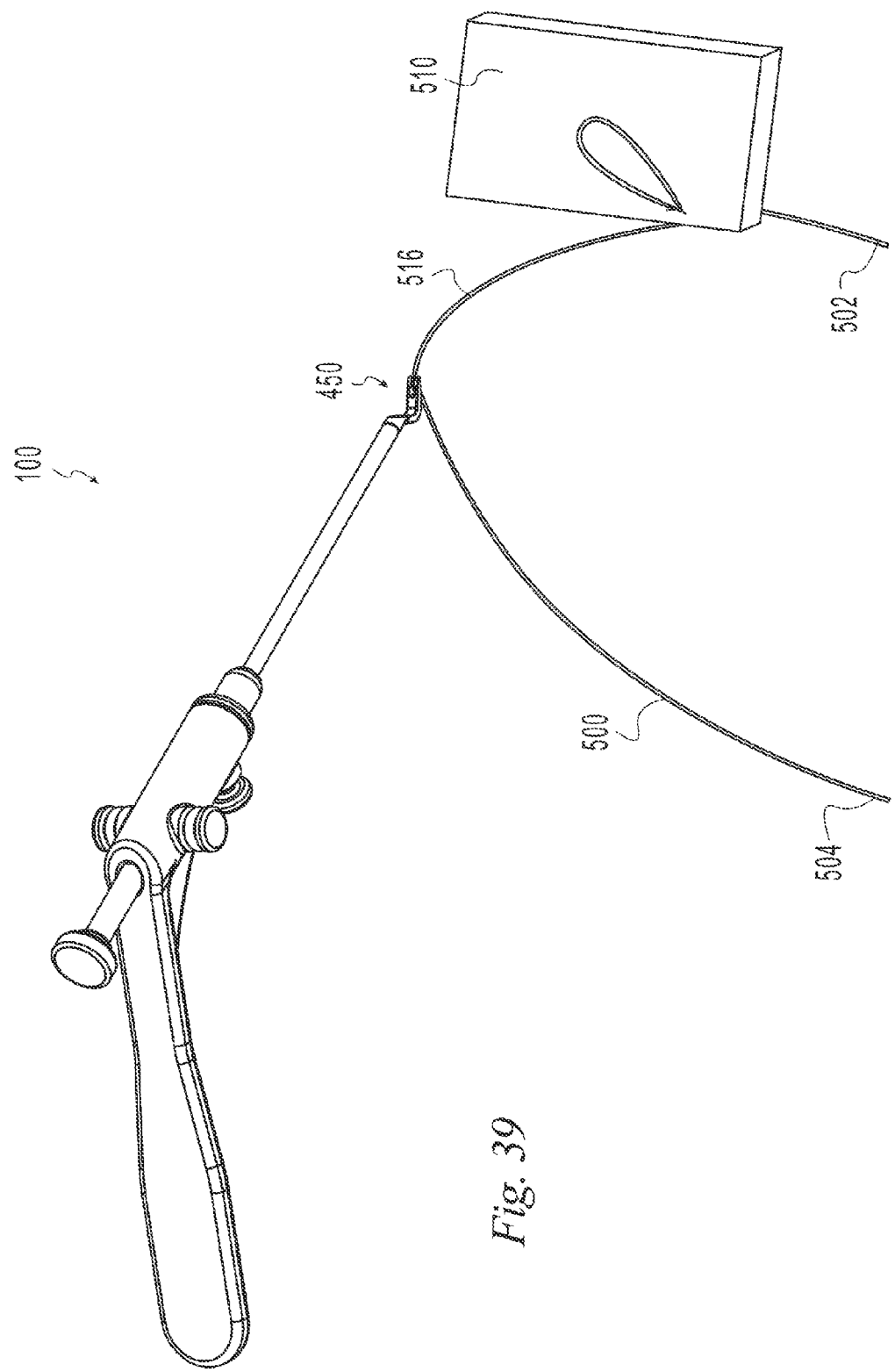
Figure 40:
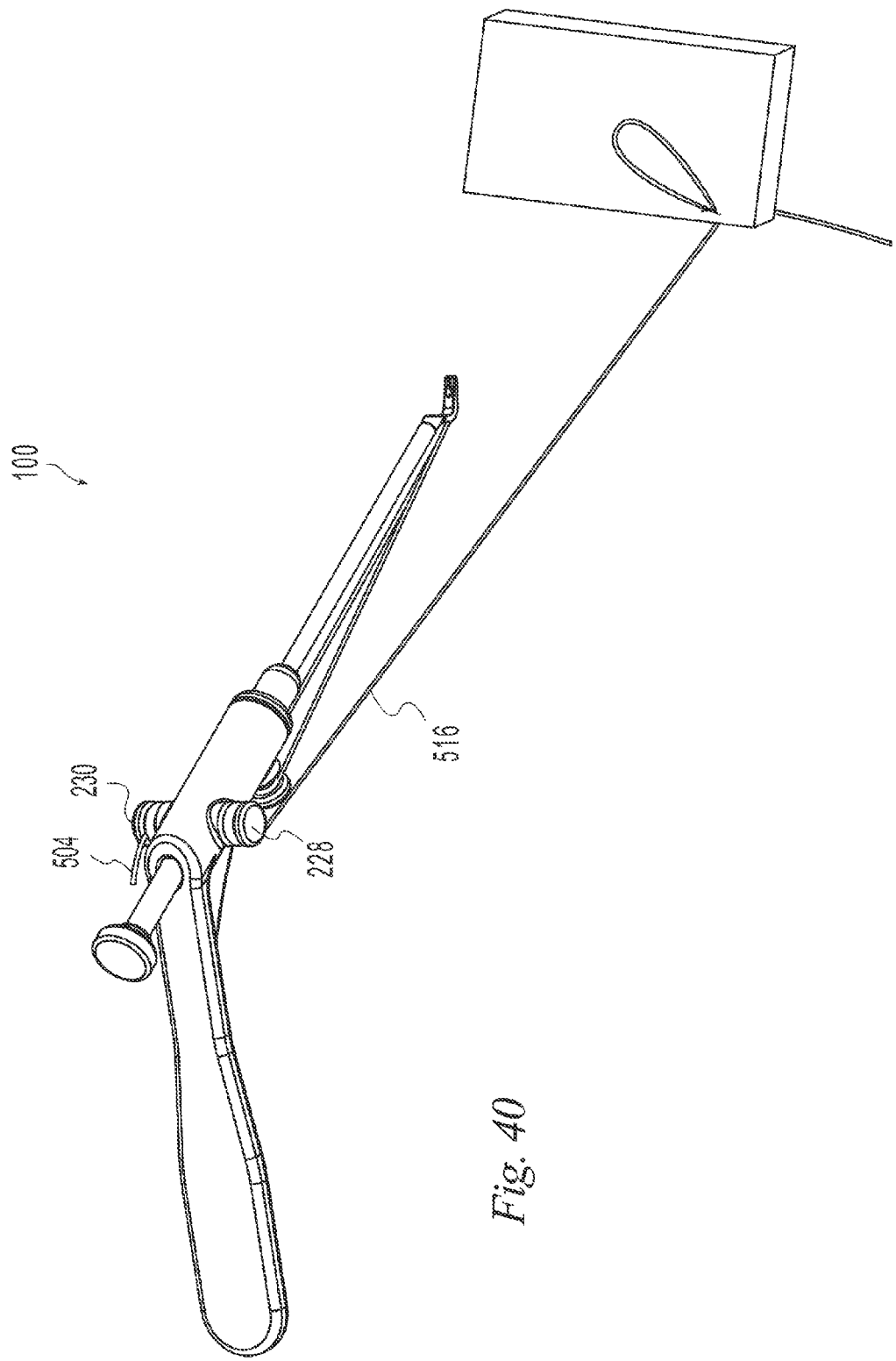
Figure 41:
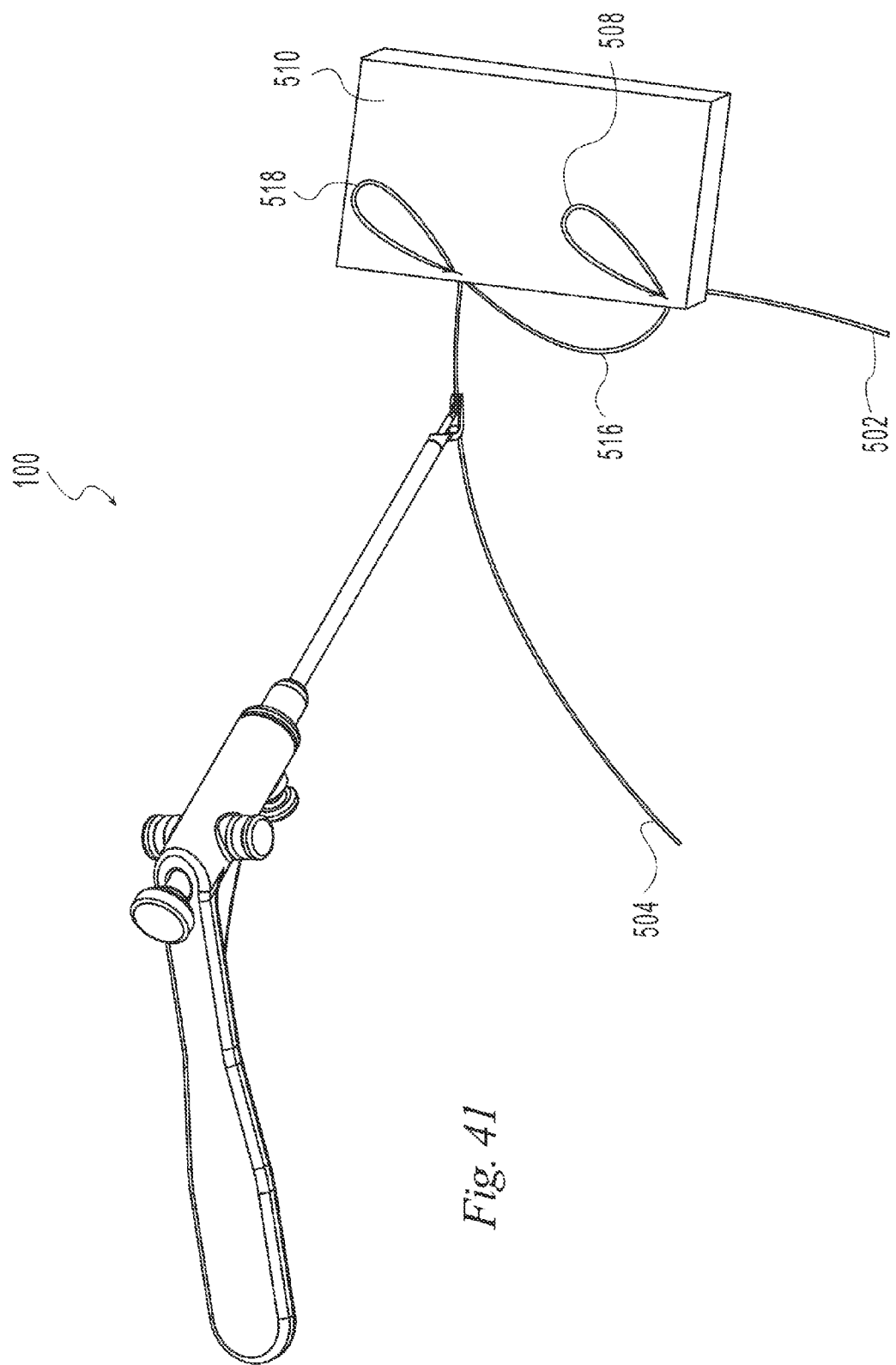

Referring to FIG. 39, the passer 100 is prepared for making a running stitch by pulling suture 500 distally through the foot to create slack 516 between the foot 450 and material 510. Referring to FIG. 40, the slack 516 and the second end 504 have been pulled proximally and secured to the knobs 228, 230. Referring to FIG. 41 a second bight 518 has been passed through the material 510 in the same manner as the first bight 508 and the slack 516 and second end 504 have been released from the passer 100.

Figure 42:
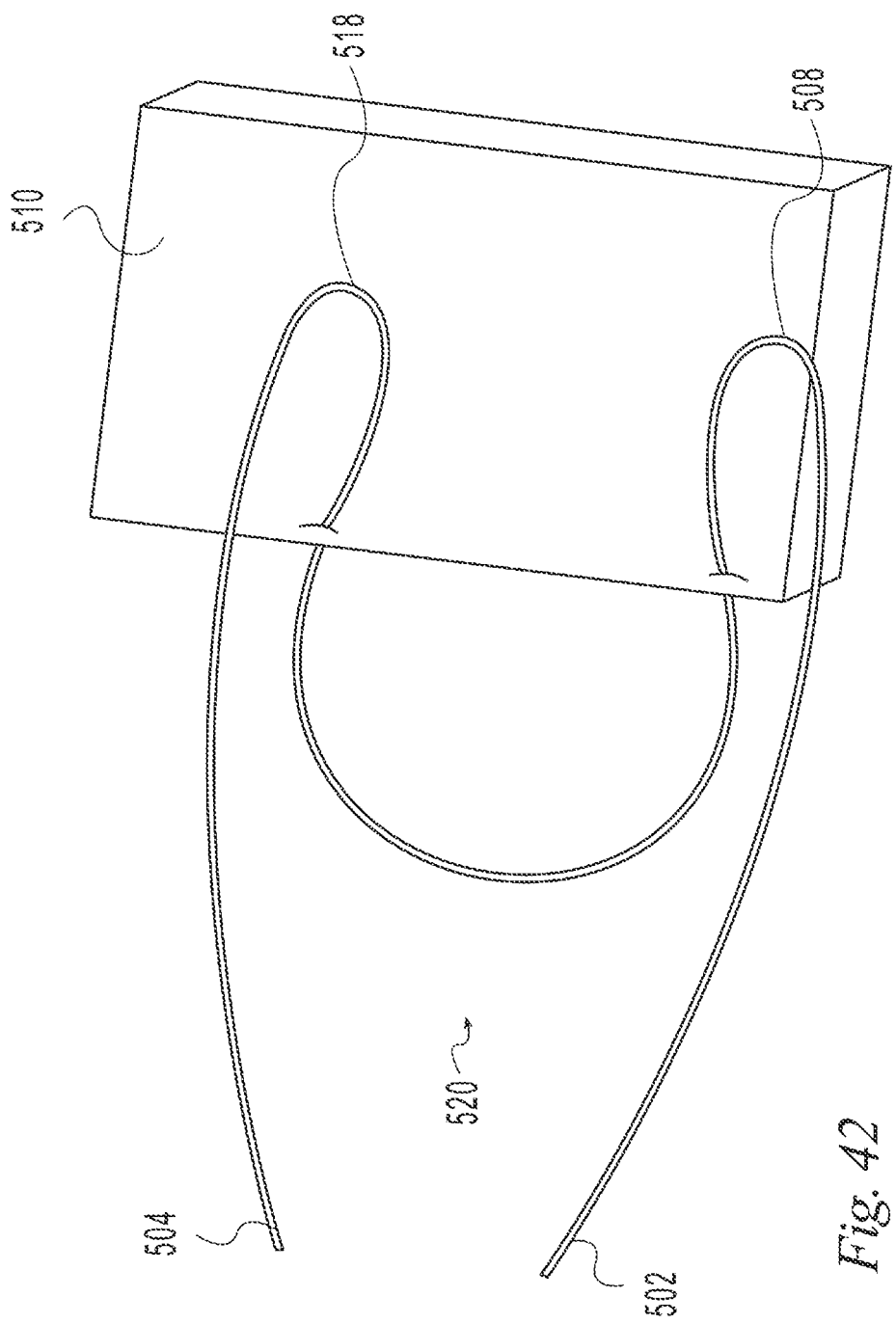

Referring to FIG. 42, the first and second ends 502, 504 have been pulled through to the front side of the material 510 by pulling on one side of each of the bights 508, 518 to form a mattress stitch 520 in the material 510.

Figure 43:
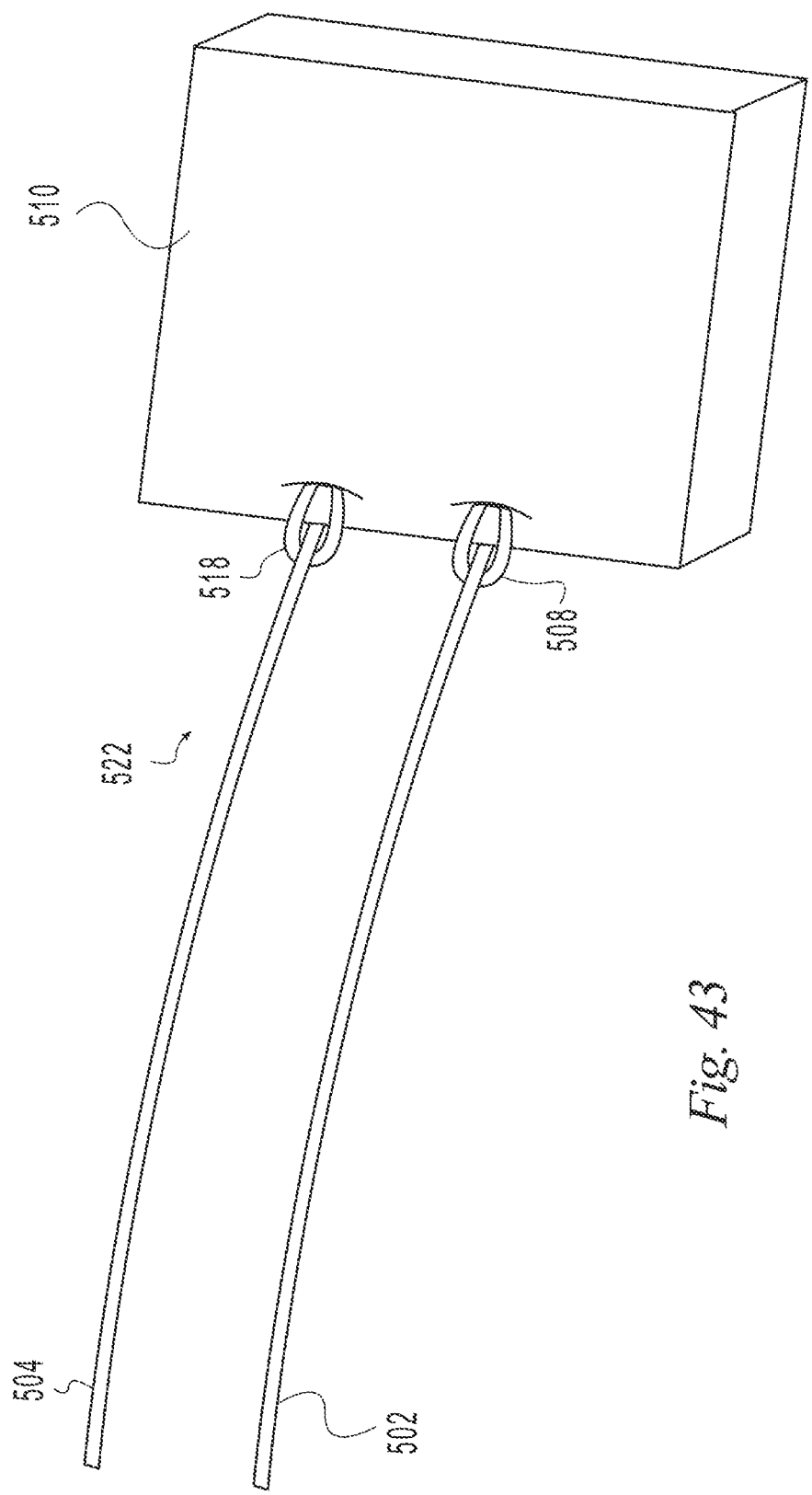

Referring to FIG. 43, instead of the ends 502, 504 being pulled through the material the first end 502 has been placed through the first bight 508 and the second end 504 has been placed through the second bight 518 to form a modified mattress stitch 522 with each end 502, 504 secured by a hitch.

Figure 44:
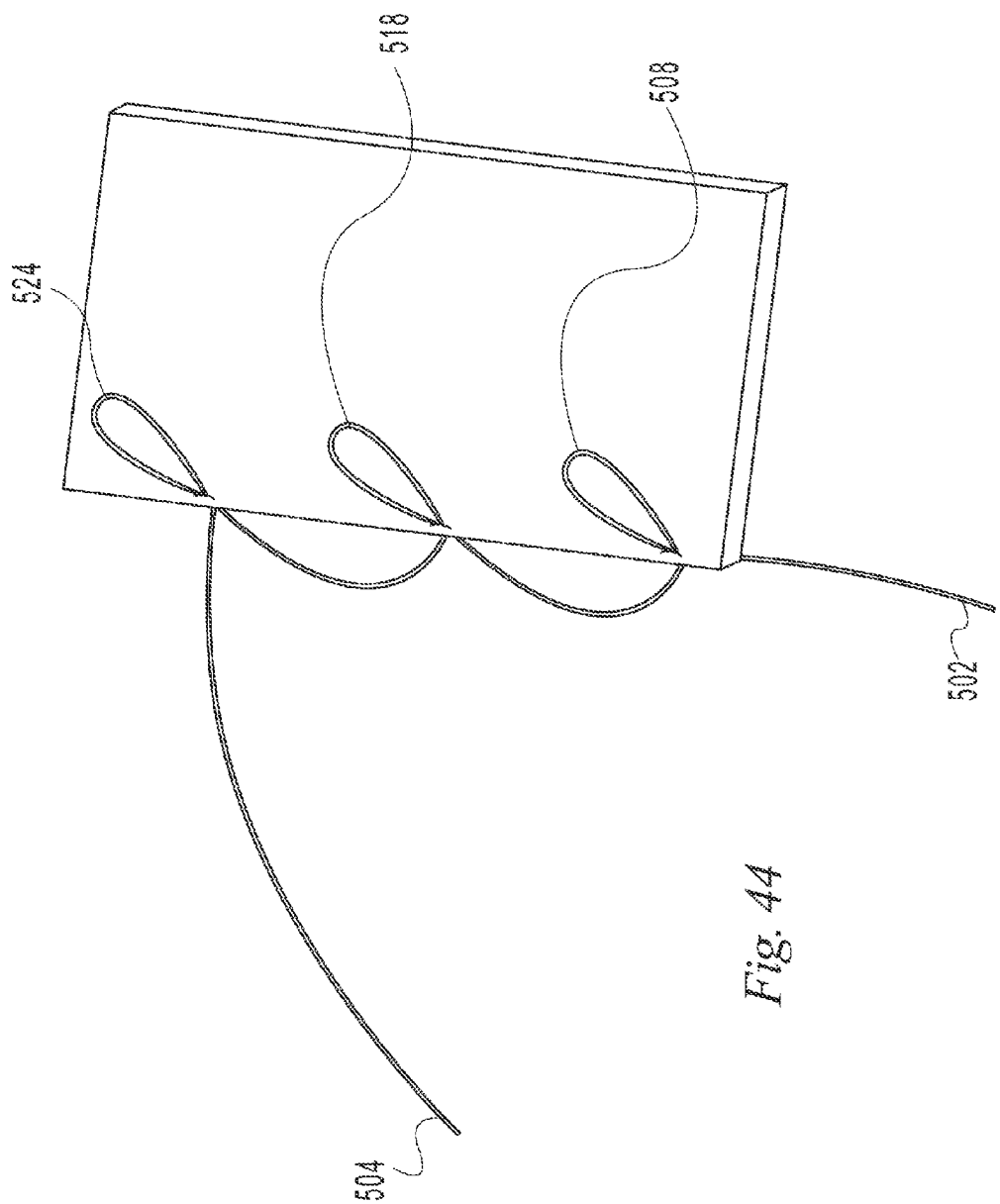
Figure 45:
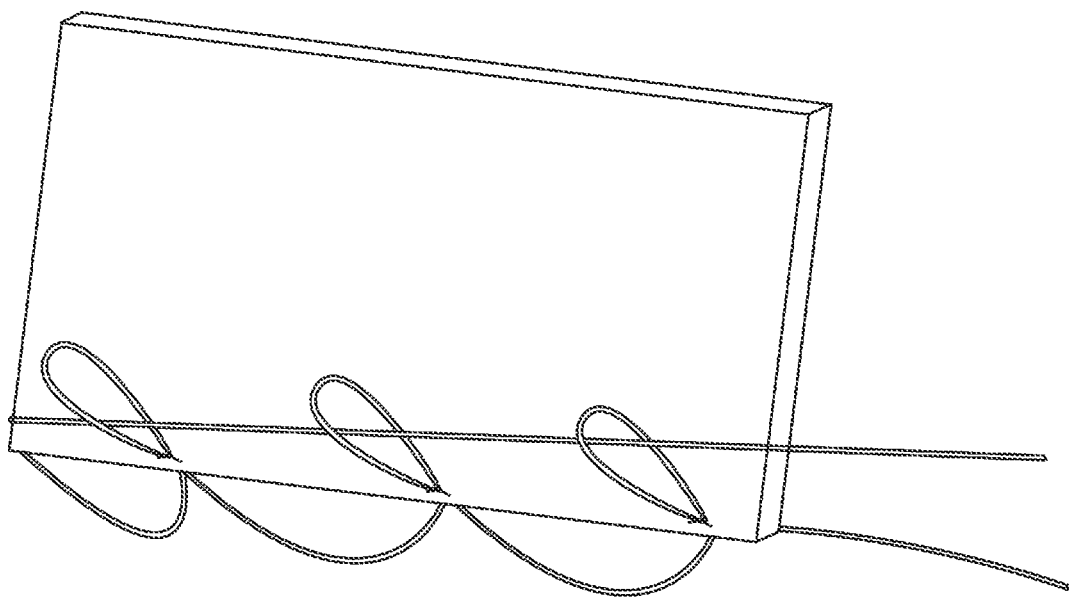

Referring to FIG. 44, a third bight 524 has been pulled through the material in the same manner as the first two bights 508, 518. A stitch may be formed by placing one or both ends 502, 504 through the bights 508, 518, 524 to lock the bights as shown in FIG. 45.

Figure 46:
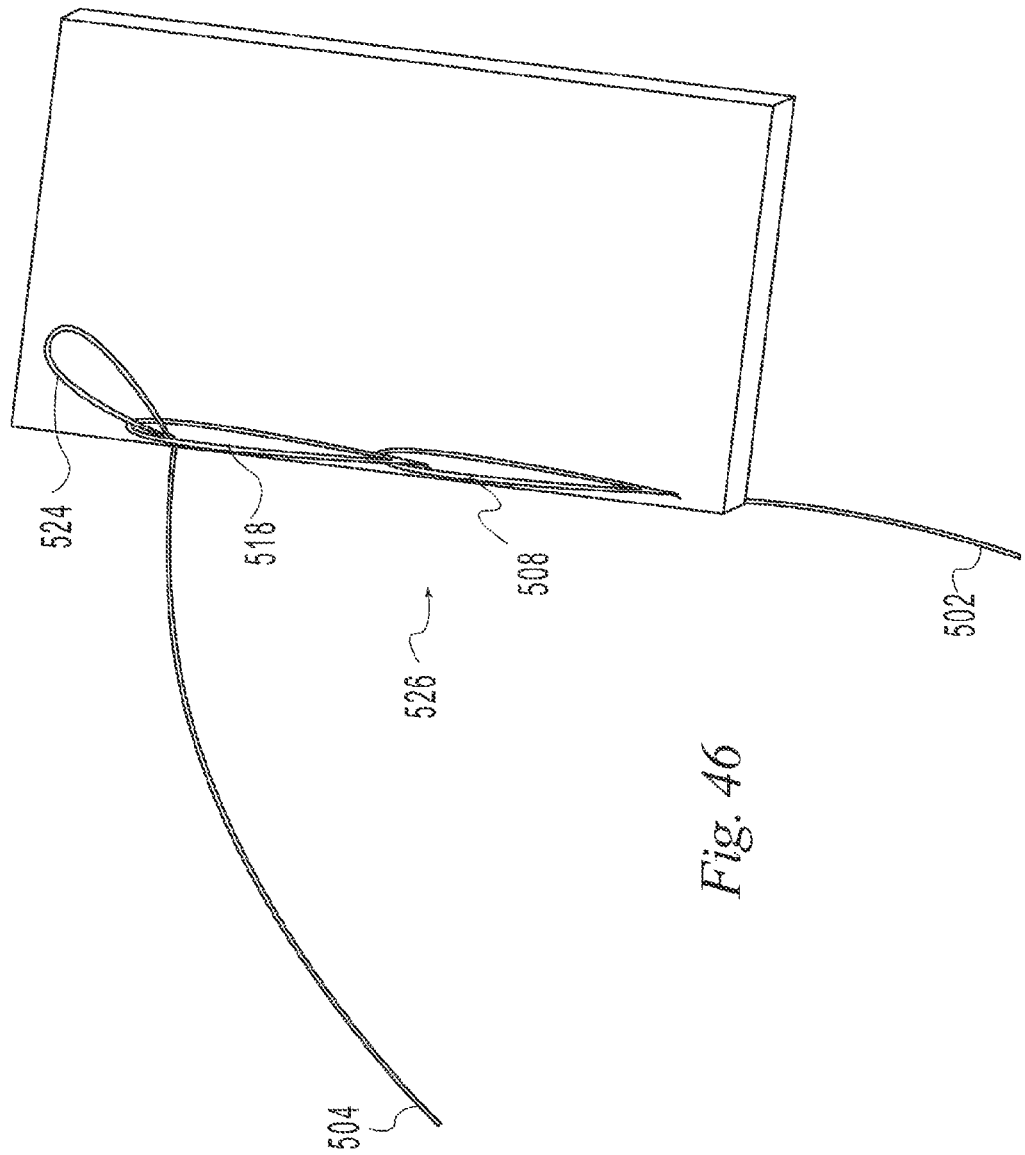

Referring to FIG. 46, instead of placing the ends through the bights, the second bight 518 has been looped through the first bight 508, and the third bight 524 has been looped through the second bight 518 to form a chain stitch 526.

Figure 47:
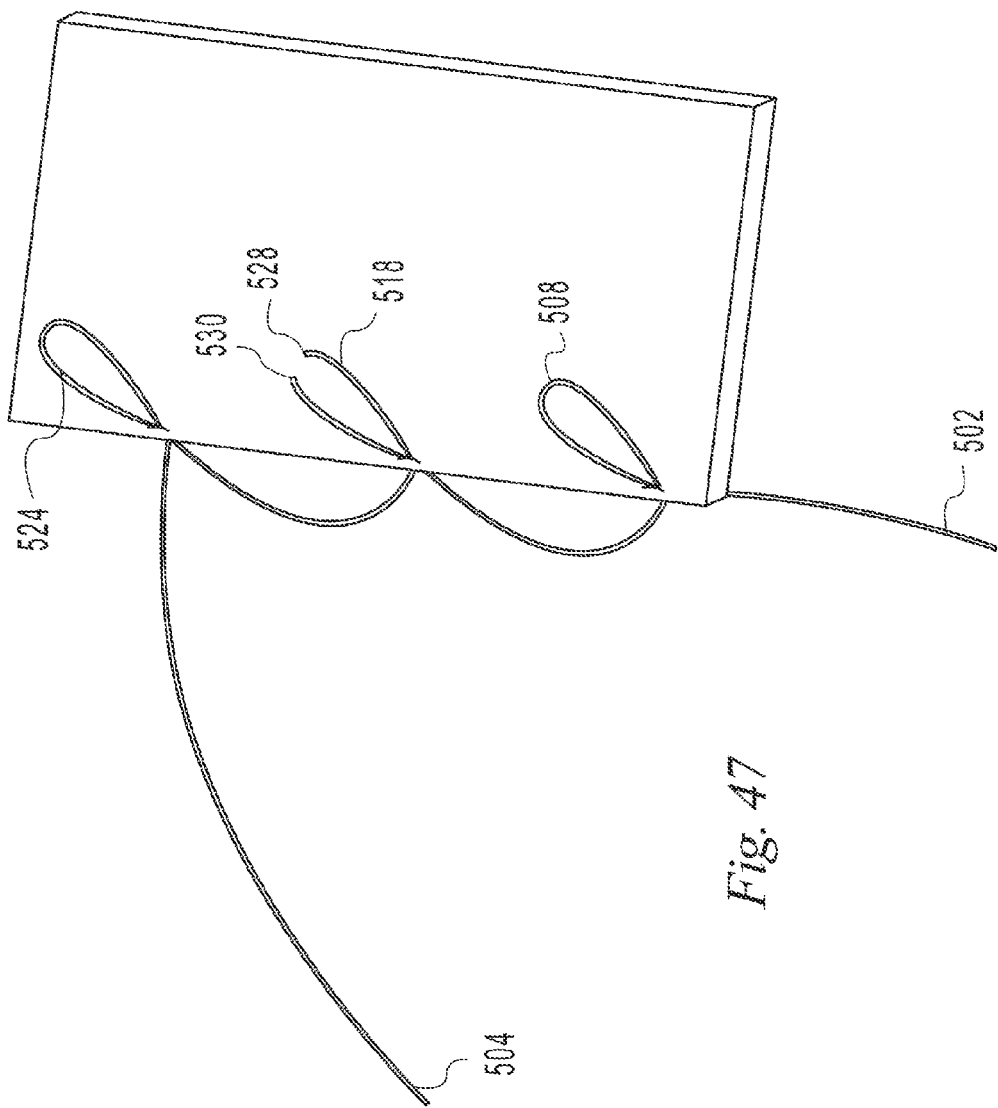
Figure 48:
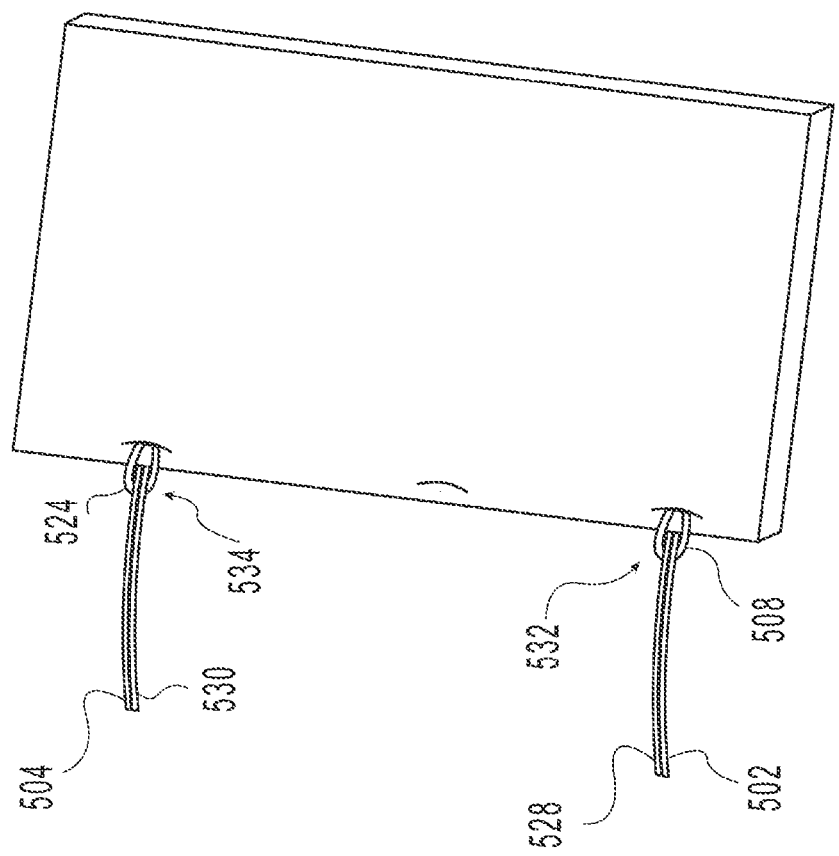

Referring to FIGS. 47 and 48, another alternative to forming stitches with three bights is shown. Here, the second bight 518 has been cut to form third and fourth ends 528, 530. The third and fourth ends 528, 530 are pulled back through the material 510 and then the first and third ends 502, 528 are placed through the first bight 508 to form a first hitch 532 and the second and fourth ends 504, 530 are placed through the third bight 524 to form a second hitch 534.

Alternatively, as shown in FIGS. 49 and 50, the same construct could be produced by forming two bights 508, 518, and cutting through the slack 536 on the back side of the material 510 to produce third and fourth ends 538, 540 which with the first and second ends 502, 504 are used to form hitches 542, 544.

The illustrative examples of FIGS. 5-50 have been shown in use to pass suture through material to form illustrative stitches. The invention is not limited to the specific instruments and methods depicted. Furthermore, it is to be understood that instruments and methods according to the invention may be used to pass any number of bights of suture through one or more materials and form any desirable construct.

The illustrative examples of FIGS. 51-78 depict instruments and techniques to pass a suture through a material. Instruments and techniques according to the illustrative examples of FIGS. 51-78 may be used to pass a suture through any material, at surgical sites anywhere in a patient's body, and for any purpose. Instruments and techniques according to the illustrative examples of FIGS. 51-78 are particularly useful to pass a suture through a bone tunnel in an orthopedic procedure. For example, it is often desirable to pass a suture through a bone tunnel which in turn is used to pass a graft into the tunnel or attach a graft in the tunnel. While suture passers in accordance with the illustrative examples of FIGS. 51-78 may be used with any material at any location, and in particular with any bone adjacent any joint within a patient's body, the illustrative examples are shown in use with a small bone joint such as in a hand or foot to form a tunnel in and pass a graft into a metacarpal or metatarsal bone. In particular, the illustrative examples are shown in use with a phalanx bone of the foot.

Figure 51:
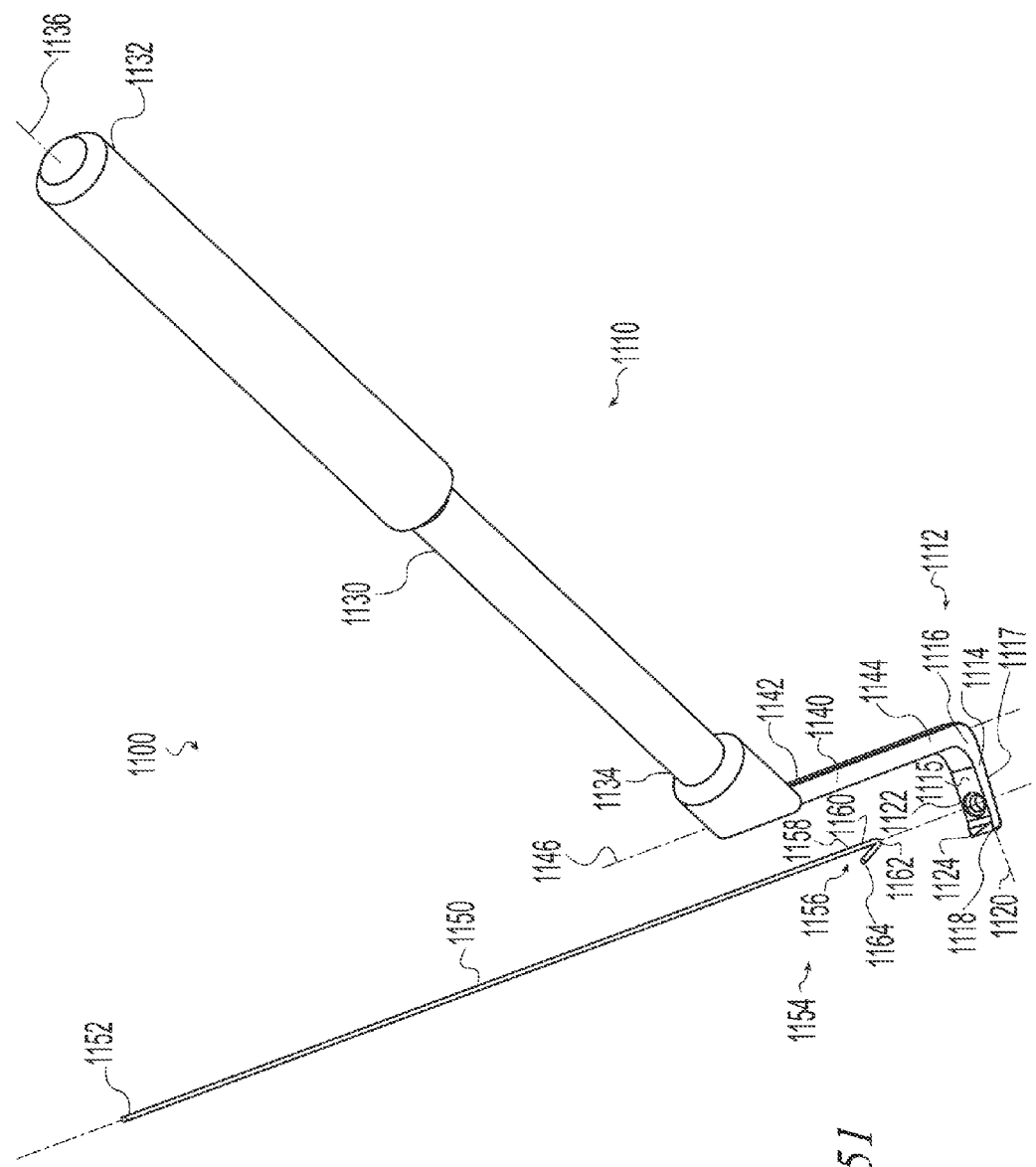
FIG. 51 is an exploded perspective view of an illustrative example of a suture passer according to the present invention.

FIG. 51 depicts an illustrative example of a suture passer 1100. The suture passer 1100 includes a suture retriever 1110 and a suture 1150. The retriever 1110 includes a receiver 1112 able to receive and retain a portion of the suture 1150. In the illustrative example of FIG. 51, the receiver 1112 includes a foot 1114 positionable on one side of a material through which the suture is to be passed. The foot 1114 has a proximal end 1116, a distal end 1118, a front surface 1115, a back surface 1117 and a longitudinal axis 1120 extending between the proximal and distal ends. The foot has an opening 1122 defining a passage through a portion of the receiver for receiving the suture 1150 and a sharp tip 1124 able to engage the material and aid in maintaining the foot 1114 in a desired location. In the illustrative example of FIG. 51, the retriever 1110 further includes a handle 1130 having a proximal end 1132, a distal end 1134, and a longitudinal axis 1136 extending between the proximal and distal ends. The receiver 1112 may be mounted directly to the distal end 1134 of the handle. In the illustrative example of FIG. 51, the receiver 1112 is offset from the handle. An extension 1140 having a proximal end 1142, a distal end 1144, and a longitudinal extension axis 1146 extends away from the distal end 1134 of the handle transverse to the handle axis 1136. The foot 1114 is mounted to the distal end 1144 of the extension 1140 and extends away from the extension 1140 transverse to the extension axis 1146.

The suture 1150 includes a proximal end 1152 and a distal end 1154. The distal end includes a stopper 1156. In the illustrative example of FIG. 51 the stopper 1156 includes a hook 1158 formed on the distal end 1154. For example, the distal end may be bent, molded, heat set, or otherwise formed into a hook shape. The hook 1158 includes a shank 1160, a bend 1162, and a barb 1164. The hook 1158 is receivable in the opening 1122. As the hook 1158 is advanced through the opening 1122, the barb 1164 and shank 1160 engage the sides of the opening 1122 and the barb 1164 moves toward the shank 1160. This movement changes the orientation of the hook to a receivable orientation in which the barb-shank maximum dimension is smaller than the opening 1122 maximum dimension and the hook passes through the opening. Once the hook 1158 is through the opening 1122, the barb 1164 springs away from the shank 1160 and the hook orientation changes to a retention orientation. Pulling the hook 1158 back toward the opening causes the barb 1164 to engage the back surface 1117 of the foot and resist withdrawal. The bend of the hook 1158 is such that relatively small movement of the barb 1164 is necessary for insertion of the hook through the opening 1122 but relatively large movement of the barb 1164, in the opposite direction, is necessary for removal. The hook 1158 may be withdrawn by forcing the barb to straighten or by clipping the hook 1158 off of the suture 1150.

The proximal end of the suture may be unmodified or it may include a loop, knot, hook, barb, or other feature for engaging another material.

In use, the receiver 1112 is positioned behind material through which the suture 1150 is to be passed. The distal end 1154 of the suture is advanced through the material and the stopper 1156 is engaged with the receiver 1112. The receiver 1112 is then withdrawn from behind the material to advance the suture further and retrieve it partially or fully through the material. The suture 1150 may be used to connect the material to another material. For example the suture 1150 may be used to attach soft tissue to bone. The suture 1150 may be used to retrieve something through the material. For example, the suture 1150 may be used to retrieve a graft through a bone tunnel. In the illustrative example of FIG. 51, the foot 1114 may be positioned adjacent a bone with the opening 1122 aligned with a tunnel formed in the bone and the tip 1124 engaged with the bone. The distal end 1154 of the suture 1150 may be advanced through the bone tunnel and opening 1122 until the hook 1158 engages the foot 1114. The proximal end 1152 of the suture may be secured to a graft such as by tying, stitching, looping, knotting, hooking, or other securing mechanism. The foot may then be withdrawn away from the bone tunnel to retrieve the distal 1154 end of the suture and pull the graft with it. Further pulling of the suture advances the graft into the bone tunnel.

FIGS. 52-59 depict an illustrative example of a suture passer 1200 similar to that of FIG. 51 and including a suture retriever 1300 and a suture 1400. In the illustrative example of FIGS. 52-59, the suture retriever 1300 includes a handle 1310, a receiver 1320, and a guide 1380. The handle 1310 includes a proximal end 1312, a distal end 1314, and a longitudinal axis 1316 extending between the proximal and distal ends. The receiver 1320 includes a foot 1324 positionable on one side of a material through which the suture is to be passed. The foot 1324 has a proximal end 1326, a distal end 1328, a front surface 1325, a back surface 1327 and a longitudinal axis 1330 extending between the proximal and distal ends. The foot 1324 has an opening 1332 having an opening axis and able to receiving the suture 1400. The opening 1332 includes an enlarged counterbore 1333. The foot further includes a sharp tip 1334 able to engage the material and aid in maintaining the foot 1324 in a desired location. The receiver 1320 is offset from the handle 1310. An extension 1340 having a proximal end 1342, a distal end 1344, and a longitudinal extension axis 1346 extends away from the distal end 1314 of the handle transverse to the handle axis 1316. The foot 1324 is mounted to the distal end 1344 of the extension 1340 and extends away from the extension 1340 transverse to the extension axis 1346.

The guide 1380 includes a tube 1382 having an inner surface 1384, an outer surface 1386, a proximal end 1388, and a distal end 1390. The inner surface 1384 defines an inner diameter and a longitudinal axis 1392. The tube 1382 is mounted to the distal end 1314 of the handle 1310 with the tube axis 1392 transverse to the handle axis 1316 and coaxial with the opening 1332 in the foot 1324. The handle 1310 axis 1316 forms an angle 1317 with the tube axis 1392. The angle 1317 facilitates manipulating the retriever 1300 while maintaining a line of sight for the user and to prevent interference with tissues surrounding the surgical site. The angle 1317 may have any suitable value. Preferably the angle 1317 is in the range of 90 to 270 degrees. The handle 1310 may also be mounted at any location around the circumference of the tube 1382. In the illustrative embodiment of FIGS. 52-59, the handle is coplanar with the foot 1324. The tube 1382 includes a slot 1394 through the sidewall of the tube from the inner surface 1384 to the outer surface 1386 and extending from the proximal end 1388 to the distal end 1390. The guide 1380 and foot 1324 define a space 1396 between them for receiving a bone.

The suture 1400 includes a proximal end 1402 and a distal end 1404. The distal end includes a stopper 1406. In the illustrative example of FIGS. 52-59 the stopper 1406 includes a pledget 1408. The pledget 1408 is mounted to the suture 1400 such as by adhering, welding, crimping, molding or other suitable mounting method. The pledget 1408 may also be formed as a unitary part of the suture. The pledget is resilient to allow it to bend or compress to fit through the opening 1332. It may also be toggled to one side such as for example by bending the suture adjacent the pledget 1408 to fit through the opening 1332. In the illustrative example of FIGS. 52-59, the pledget 1408 includes radially extending tabs 1410, 1412 that bend from substantially perpendicular to the suture 1400 to substantially parallel to the suture 1400 to reduce the radial dimension of the pledget 1408 and allow it to pass through the opening in a receivable orientation. Once the pledget 1408 is through the opening 1332, the tabs 1410, 1412 spring back to their initial position and resume a retention orientation. The proximal end of the suture 1400 includes a loop 1420. The loop may be formed by tying a knot in a bight of a single or multiple strand suture 1400, tying the ends of multiple strands together, splitting a monofilament strand, molding, or other suitable loop formation method. In the illustrative example of FIGS. 52-59, the loop is formed by molding a loop on a monofilament strand. A loop may be formed near the distal end in addition to or as an alternative to loop 1420. For example, a distal loop may be formed in the suture proximal to the pledget.

Figure 60:
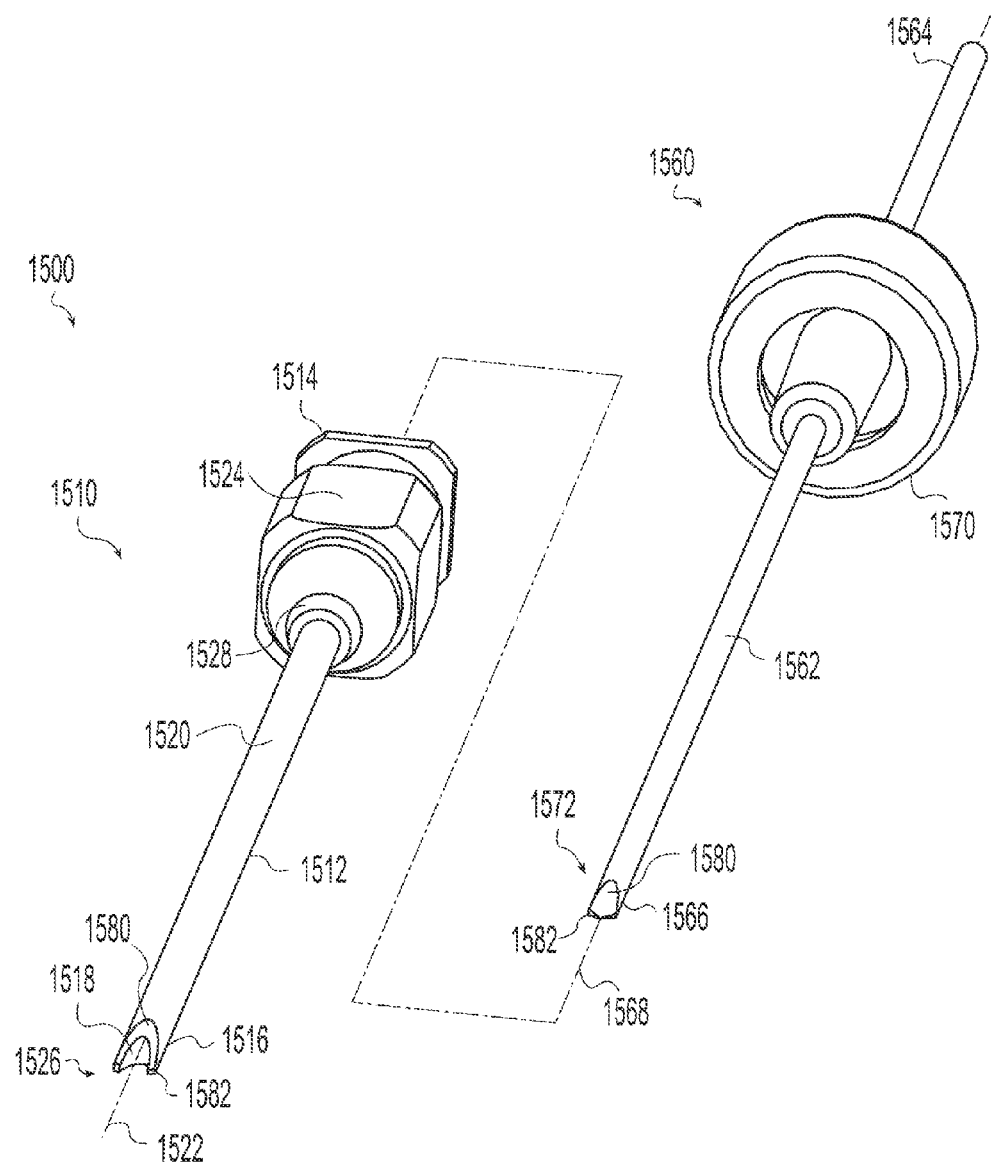
FIG. 60 is a perspective view of a drill assembly useable with the suture passer of FIG. 52.

FIG. 60 illustrates a drill assembly 1500 useable with the suture passer 200. The drill assembly 1500 includes a drill tube 1510 and an obturator 1560. The drill tube 1510 includes a tubular body 1512 having a proximal end 1514, a distal end 1516, an inner surface 1518, and an outer surface 1520. The inner surface 1518 defines an inner diameter and a longitudinal axis 1522 extending between the proximal and distal ends. In the illustrative embodiment of FIG. 60, a connector 1524 is mounted to the drill tube 1510 near the proximal end 1514. In the illustrative example of FIG. 60, the connector 1524 is a female Luer-type fitting. A stop 1528 extends radially outwardly from the body 1512.

The obturator 1560 includes an elongated body 1562 having a proximal end 1564, a distal end 1566, and a longitudinal axis 1568 extending between the proximal and distal ends. In the illustrative embodiment of FIG. 60, a connector 1570 is mounted to the obturator 1560 intermediate the proximal and distal ends. In the illustrative example of FIG. 60, the connector 1570 is a male Luer-type fitting. The obturator 1560 is receivable in the drill tube 1510 by inserting the distal end 1566 of the obturator 1560 into the proximal end 1514 of the drill tube 1510 and advancing the obturator until the connectors engage. The obturator 1560 and drill tube 1510 are locked together by rotating the connectors relative to one another. The drill tube 1510 and obturator 1560 have drilling tips 1526, 1572 that align when the obturator is inserted into the drill tube and locked. For example, the drilling tips 1526, 1572 may be formed by assembling the obturator 1560 and drill tube 1510, locking them together, and then grinding the cutting tips on the drill tube 1510 and obturator 1560 simultaneously. In the illustrative example of FIG. 60, when the drill tube 1510 and obturator 1560 are assembled, the drilling tips 1526, 1572 form a diamond drill tip having primary bevels 1580 formed on opposed first and second sides and secondary bevels 1582 to provide relief and improve cutting. The outer diameter of the drill tube 1510 and the counterbore 1333 of the opening 1332 are sized so that the drill tube 1510 may be received in the counterbore 1333.

Figure 61:
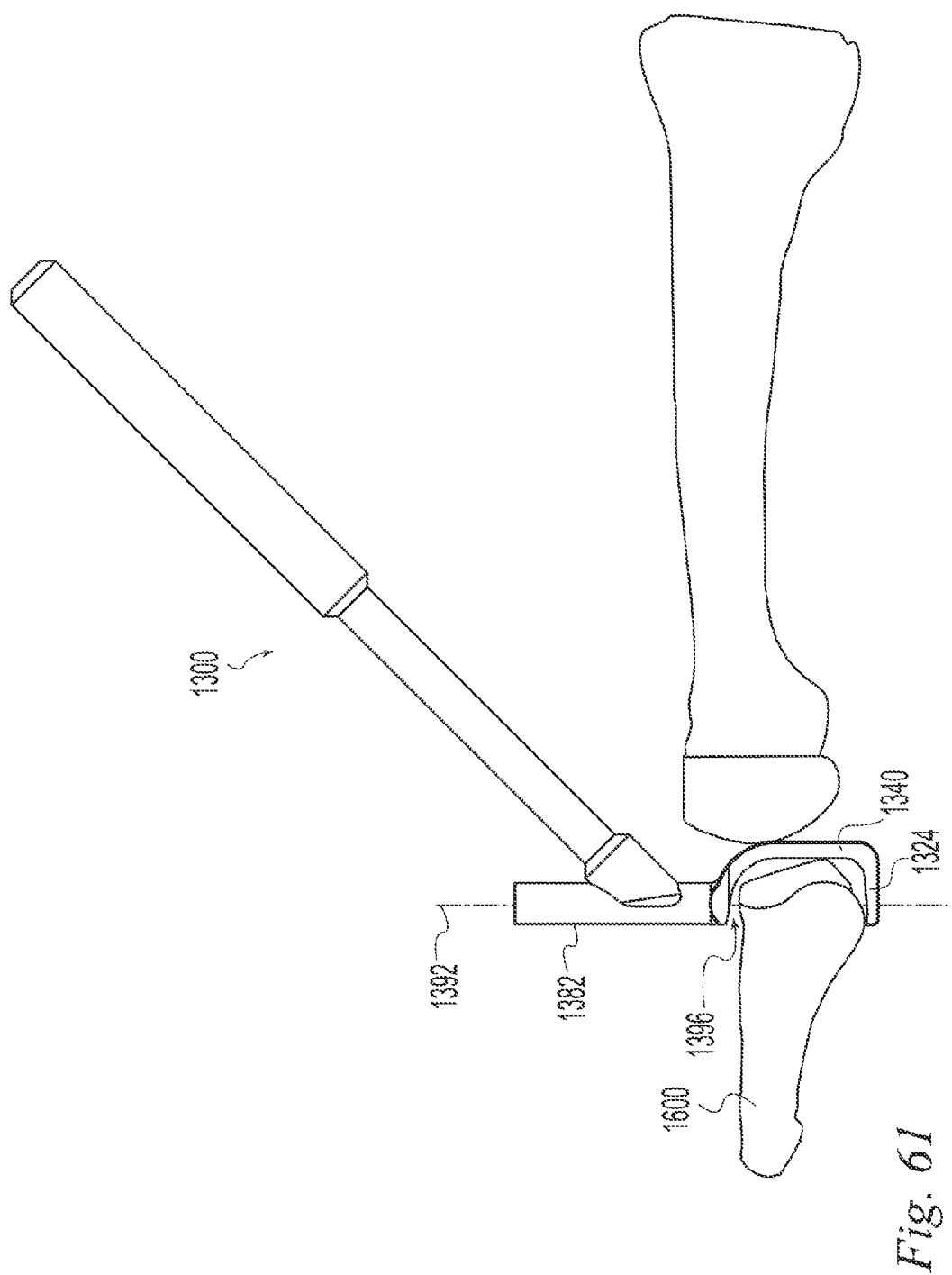
FIGS. 61-70 are side elevation views illustrating the suture passer of FIG. 2 in use.

FIGS. 61-70 illustrate the illustrative suture passer 200 of FIGS. 52-59 and the illustrative drill assembly of FIG. 60 in use to form a bone tunnel and load a graft into the tunnel. In FIG. 61, the suture retriever 1300 has been positioned adjacent a bone 1600 with the foot 1324 on one side of the bone with the opening 1332 aligned with a desired exit location for a bone tunnel and the guide axis 1392 aligned with the desired tunnel axis. By viewing through the tube 1382 along the axis 1392, the location of the tunnel entrance can be visualized. The retriever 1300 is shown positioned adjacent a phalanx bone with the extension 1340 in the joint space and the guide positioned to form a tunnel from dorsal to plantar through the proximal phalanx. The guide may be positioned at any location around the joint to create bone tunnels at any desired location in the phalanx or the metatarsus. For example, the guide may be positioned to create tunnels for repairing or replacing a proper collateral ligament, accessory plantar ligament, plantar plate, or other structure in or around the joint.

Figure 62:
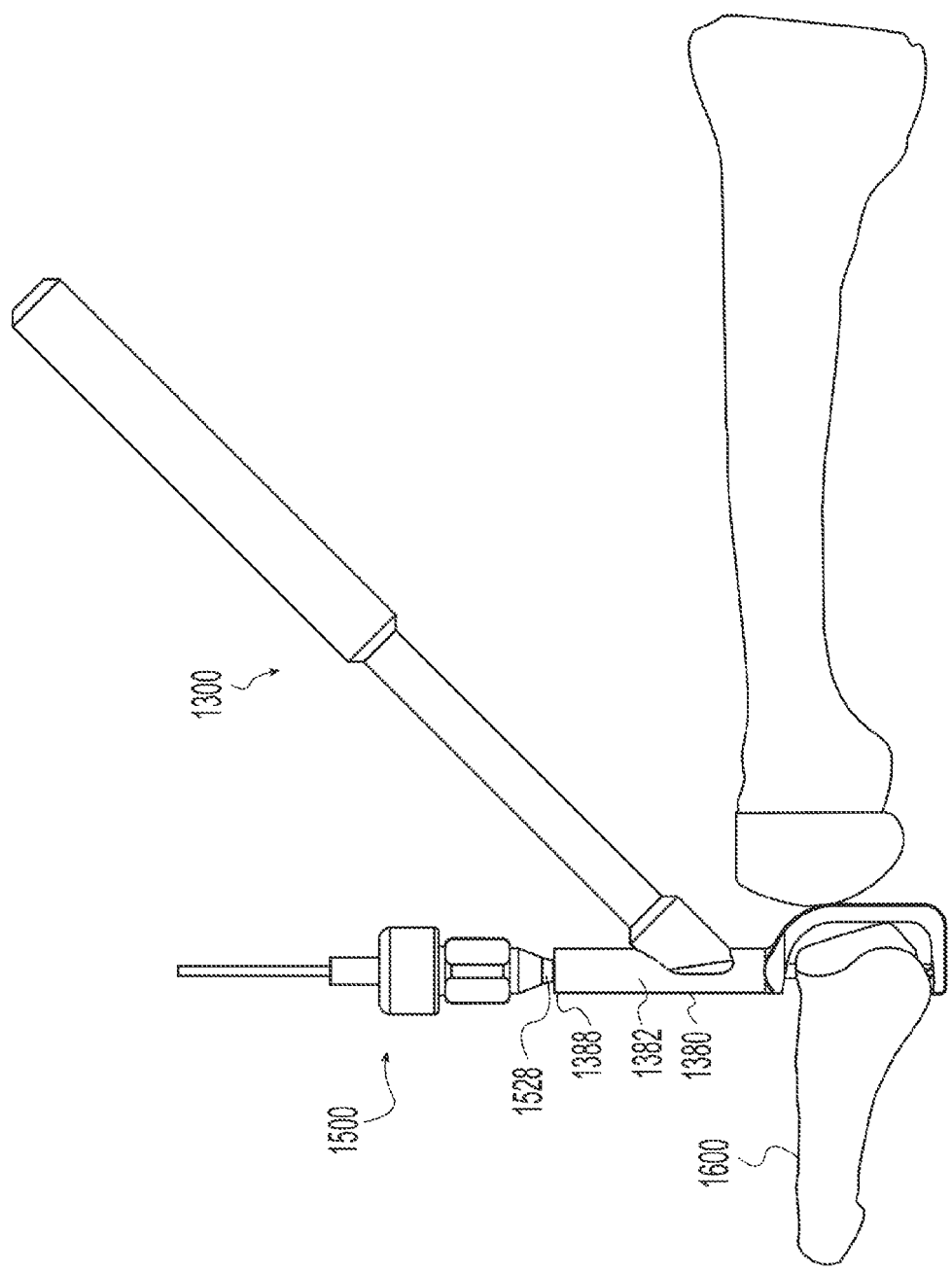

In FIG. 62, the drill assembly 1500 has been guided via the inner surface 1384 of the guide tube 1382 to form a tunnel through the bone 1600. Stop 1528 abuts the proximal end 1388 of the guide 1380 to limit the drilling depth. In the illustrative examples of FIGS. 52-60, the stop 1528 abuts the proximal end 1388 when the drill tube 1510 is received in the counterbore 1333. Alternatively, the opening in the foot may be sized to engage the tip of the drill to limit the depth or a depth stop may be omitted.

Figure 63:
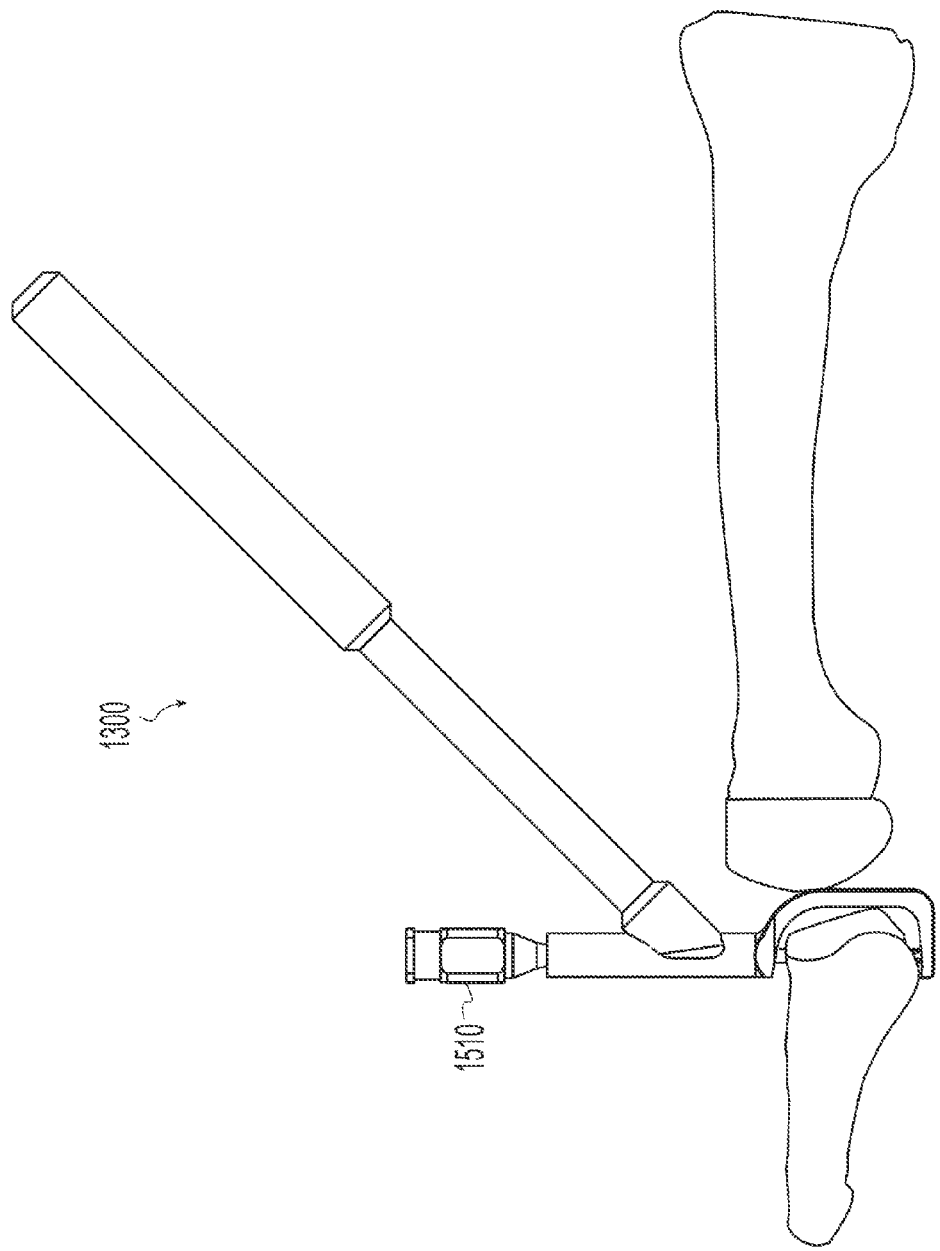

In FIG. 63, the obturator 1560 has been removed leaving the drill tube 1510 in place. Optionally, the drill tube 1510 could be removed or a one-piece drill could be substituted for the drill assembly 1500. However, by leaving the drill tube 1510 in place, the drill tube 1510 locks the retriever 1300 in place on the bone, provides guidance for the suture, and provides a smooth passage for the suture.

Figure 64:
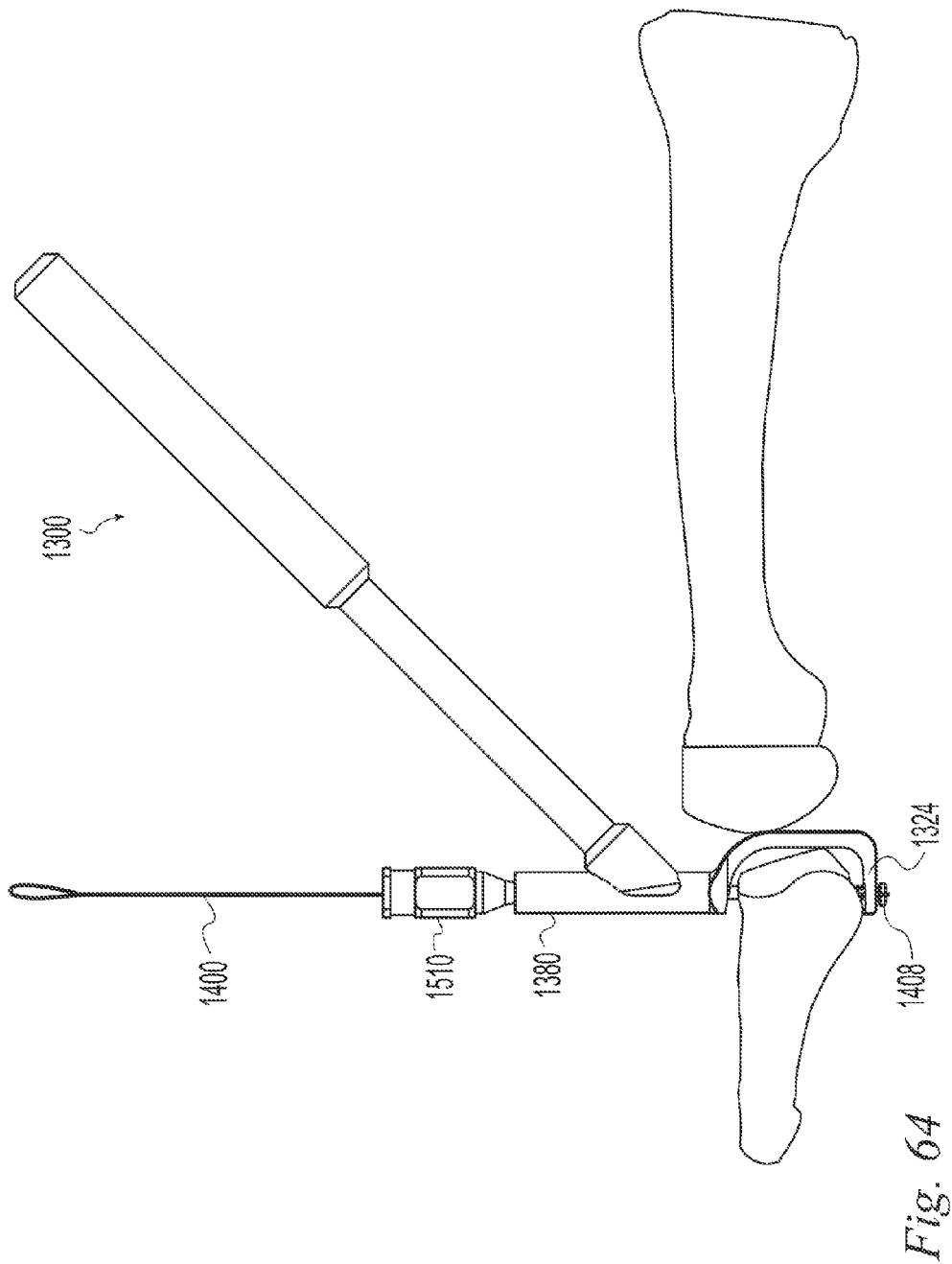

In FIG. 64, the suture 1400 has been inserted until the stopper 1406 engages the receiver 1320. In the example of FIG. 64, the pledget 1408 has been forced through the opening 1332 in the foot 1324.

Figure 65:
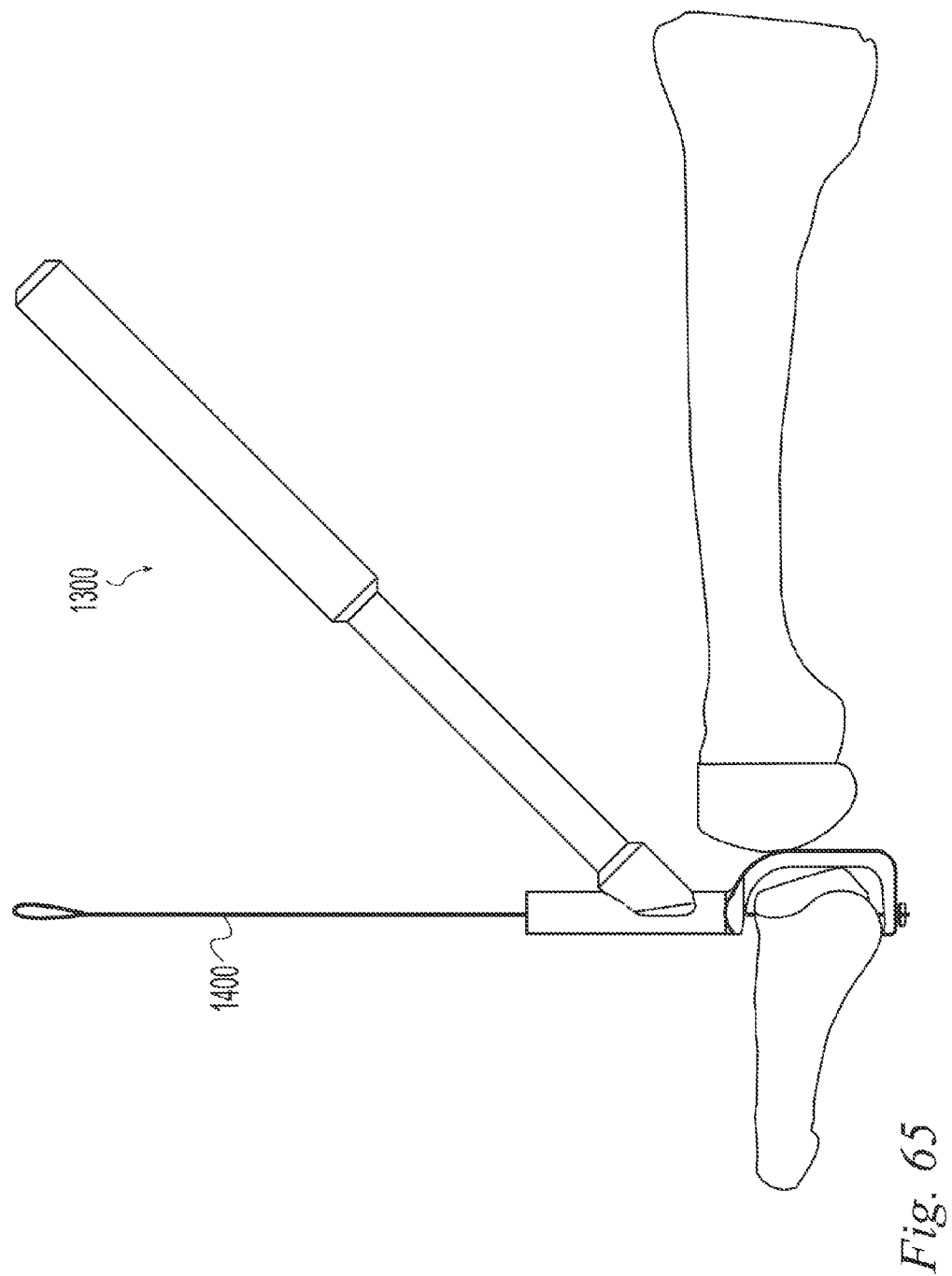

In FIG. 65, the drill tube 1510 has been removed leaving the suture 1400 in place.

Figure 66:
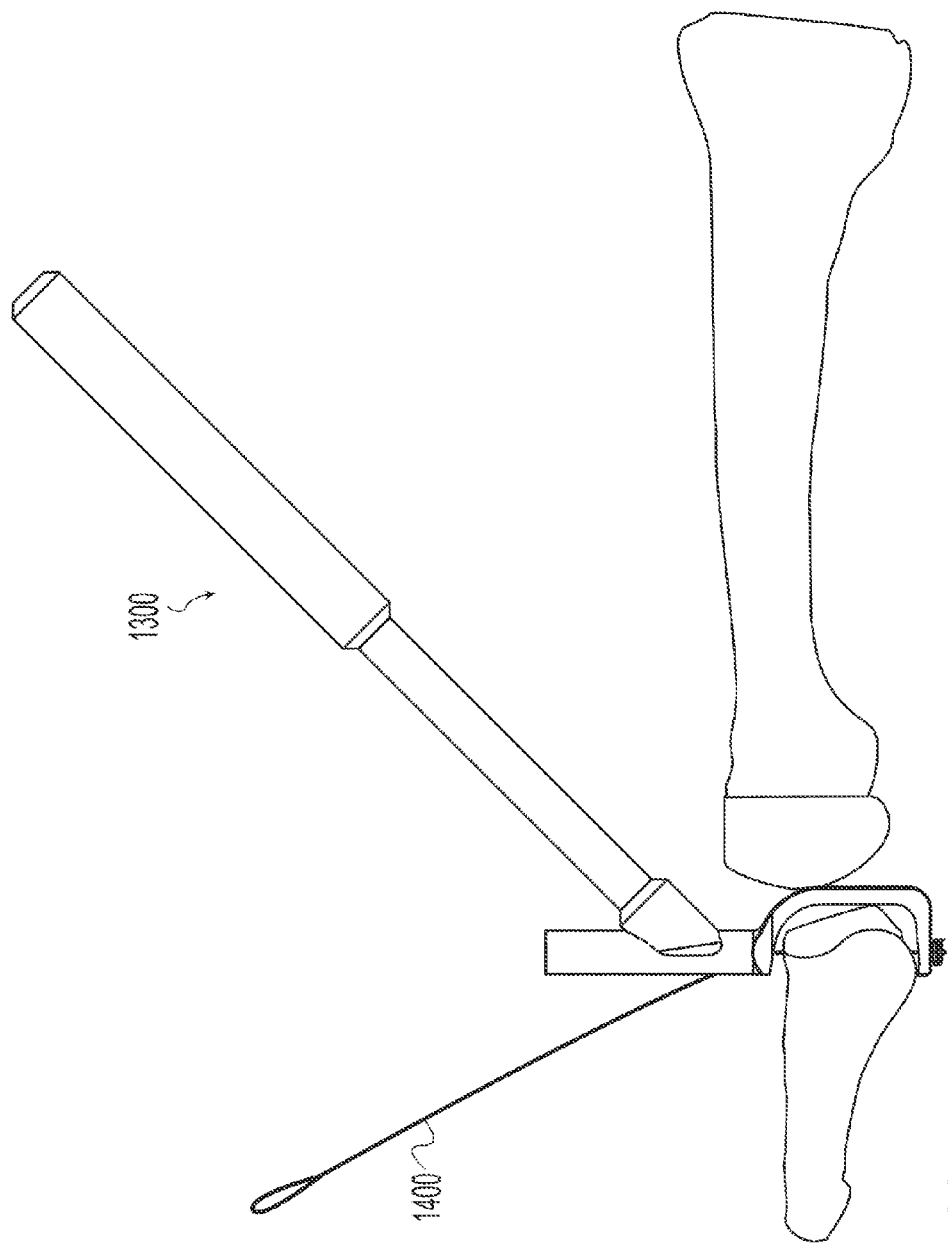

In FIG. 66, the suture 1400 has been pulled through the slot 1394 to free the proximal end 1402 from the guide tube 1382. The slot 1394 simplifies withdrawing the retriever 1300 from the surgical site. However, the slot 1394 may be omitted and the proximal end 1402 of the suture threaded through the guide tube 1382 as the retriever 1300 is withdrawn.

Figure 67:
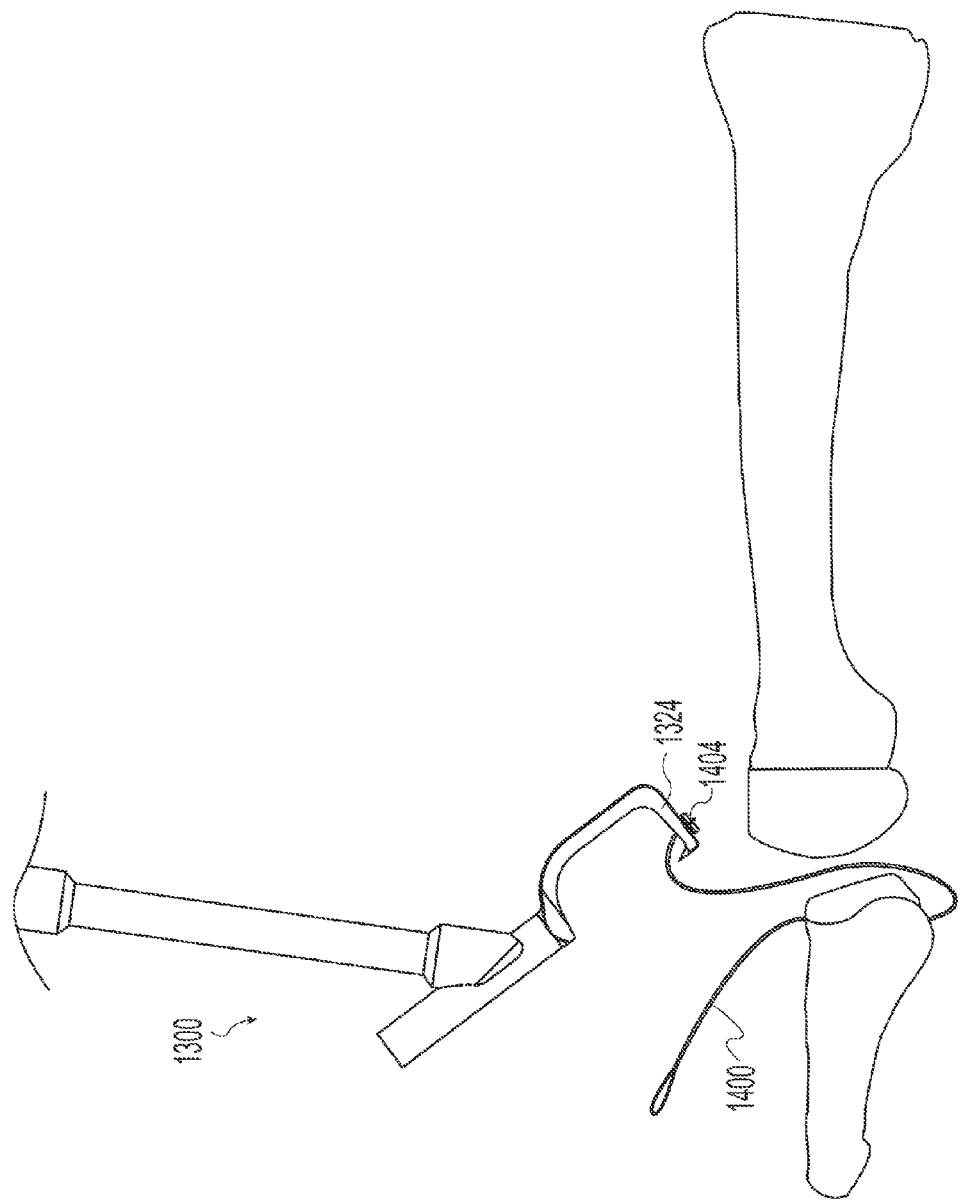

In FIG. 67, the retriever 1300 has been withdrawn from the surgical site taking the distal end 1404 of the suture 1400 with it and thereby further advancing the suture 1400 into the bone tunnel. The suture 1400 may be left attached to the retriever 1300 or it may be separated from the retriever by pulling the distal end 1404 back through the foot or cutting off the distal end 1404 of the suture.

Figure 68:
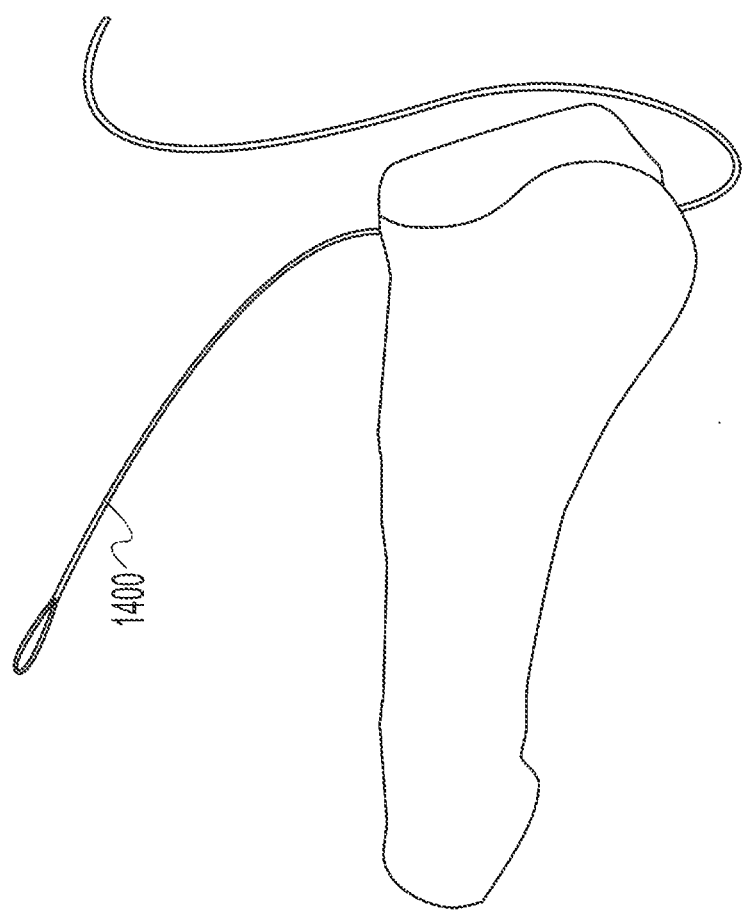

In FIG. 68, the distal end 1404 of the suture 1400 has been cut off to free it from the retriever 1300 and the retriever 1300 removed.

Figure 69:
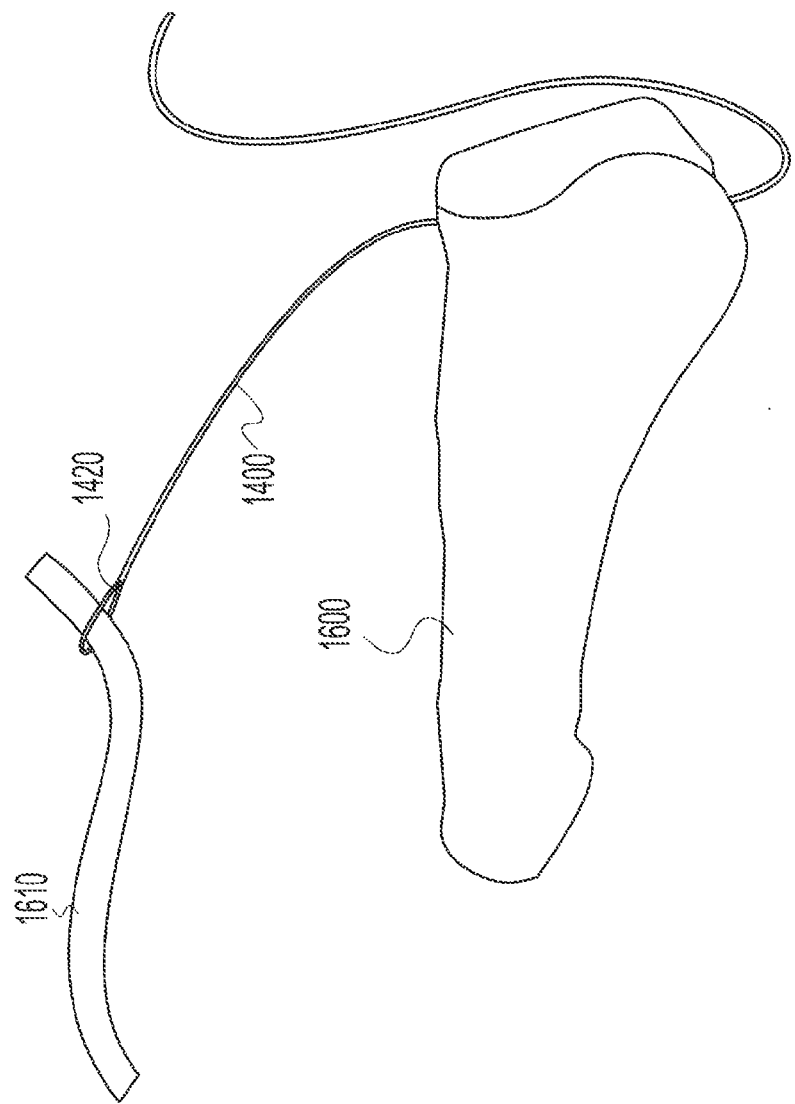

In FIG. 69, a graft 1610 has been engaged with the proximal end 1402 of the suture 1400 by threading it through the loop 1420. Alternatively, a graft or any other material may be attached to the distal end for pulling in the opposite direction. For example, such material may be attached to the distal end by tying the suture to the material. A loop may also be formed in the distal end by the user at the time of surgery or a loop may be preformed at or near the distal end. In addition to being used to retrieve a graft, the suture 1400 may be used as a definitive repair suture in a repair or reconstruction. Also, the suture 1400 may be used to pull a repair suture or another graft retrieval strand such as, for example, a larger or more flexible strand or one with one or more loops at different locations than suture 1400.

Figure 70:
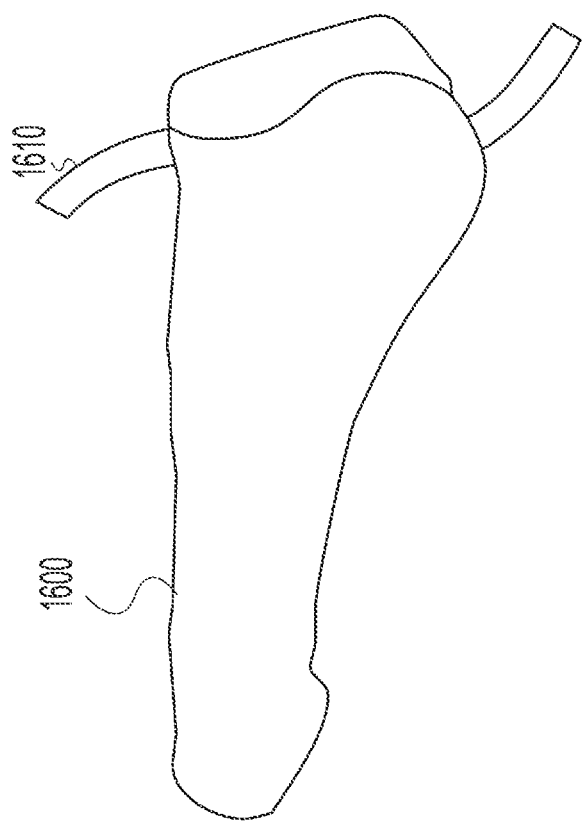

In FIG. 70, the suture 1400 has been pulled to advance it through the bone tunnel and pull the graft 1610 along with it to position the graft 1610 in the bone tunnel and the suture 1400 has been removed.

Figure 71:
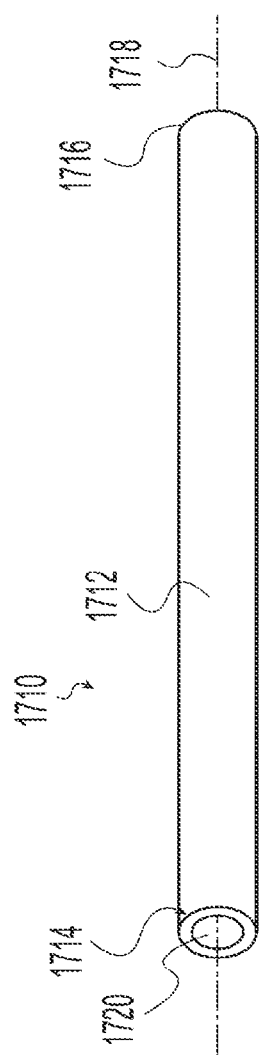
FIG. 71 is a perspective view of an optional component useable with the suture passers of FIG. 51 and FIG. 52.

FIG. 71 illustrates a suture inserter 1710 having an elongated body 1712 with a proximal end 1714, a distal end 1716, and a longitudinal axis 1718. The suture inserter 1710 may be used to advance the suture 1400 into engagement with the receiver 1320 by pushing the stopper 1406. The suture inserter 1710 or the suture inserter 1710 in combination with the suture may have a higher columnar strength than the suture alone and facilitate advancing the suture 1400. In the illustrative example, the suture inserter includes a longitudinal passage 1720 for receiving the suture 1400 with the stopper 1406 adjacent the distal end 1716.

Figure 72:
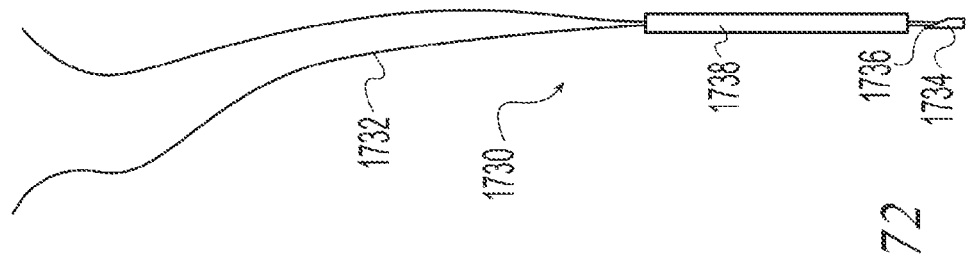
FIG. 72 is a side elevation view of an alternative suture useable with the suture passers of FIG. 51 and FIG. 52.

FIG. 72 illustrates a suture 1730 having two strands 1732 joined to a stopper 1734 having a proximal end 1736 formed at an angle to the suture strands 1732 so that the proximal end 1736 will hook onto the retriever 1320. The suture 1730 is also shown with the suture inserter 1710 of FIG. 51 useable to push the stopper 1734. For use in passing a graft, the suture strands 1732 may be tied to form a loop, stitched to the graft, wrapped around the graft, or otherwise connected to the graft. The suture ends may also be used directly to attach hard or soft tissue, implants, or other materials at a surgical site. The suture strands may also be used directly as a ligament or tendon replacement.

Figure 73:
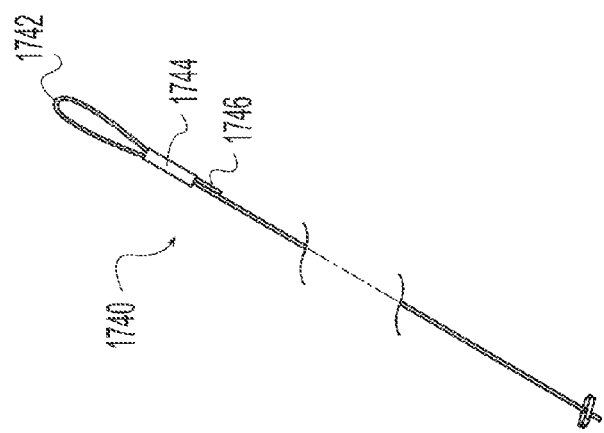
FIG. 73 is a side elevation view of an alternative suture useable with the suture passers of FIG. 51 and FIG. 52.

FIG. 73 illustrates a suture 1740 having a loop 1742 retained by swaging a ferrule 1744 to retain the proximal end 1746 of the suture 1740.

Figure 74:
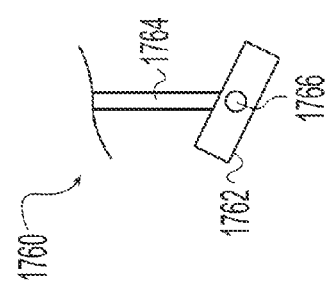
FIG. 74 is a side elevation view of an alternative stopper useable with the sutures of FIG. 51 and FIG. 52.

FIG. 74 illustrates a suture 1750 having a stopper 1752 formed of a block of resilient material such as, for example, a closed cell foam.

Figure 75:
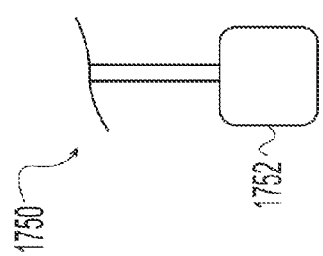
FIG. 75 is a side elevation view of an alternative stopper useable with the sutures of FIG. 51 and FIG. 52.

FIG. 75 illustrates a suture 1760 having a stopper 1762 joined to a strand 1764 at a pivot 1766 so that the stopper 1762 can toggle between a receiving position generally more parallel to the strand 1764 and a retaining position generally more perpendicular to the strand 1764.

Figure 76:
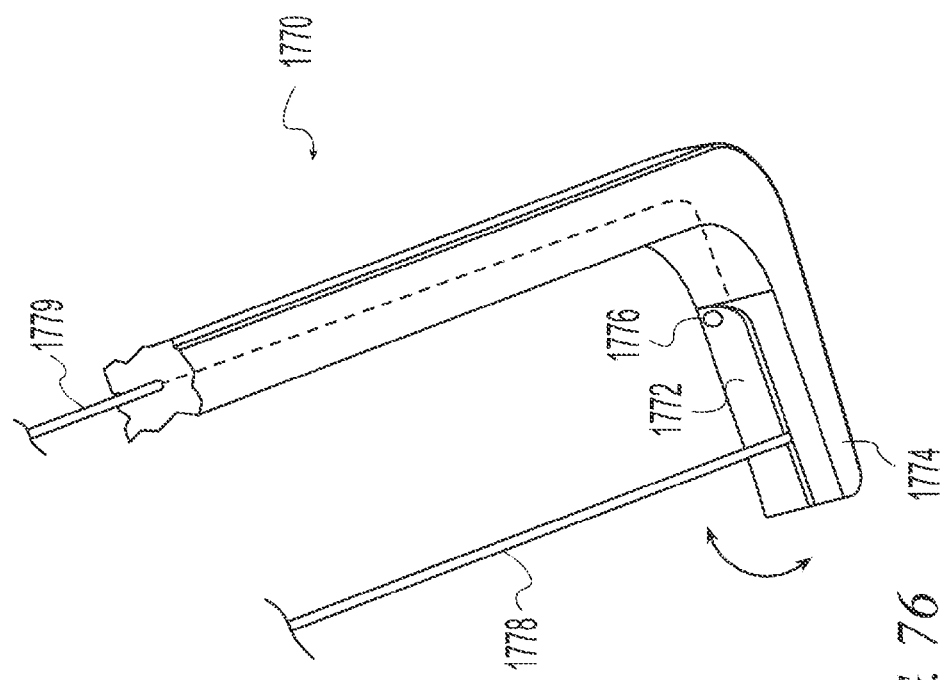
FIG. 76 is a perspective view of an alternative receiver useable with the suture passers of FIG. 51 and FIG. 52.

FIG. 76 illustrates an alternative foot 1770 to the foot 1324 of FIG. 52. The foot 1770 has first and second opposable jaws 1772, 1774. The first jaw 1772 is mounted for rotation relative to the second jaw about a pivot 1776. The jaws 1772, 1774 are moveable between a first closed, position (shown) in which the jaw faces are adjacent one another and a second, open position (not shown) in which the first jaw 1772 is pivoted away from the second jaw 1774 to create a space between the jaws 1772, 1774 for receiving a suture 1778. The jaws may be closed on the suture 1778 to retain the suture and allow it to be retrieved. Any suitable mechanism may be used to move the first jaw relative to the second jaw. For example, a control cable 1779 may be mounted in the foot and moveable by a remote actuator to move the first jaw 1772 between the first and second positions.

Figure 77:
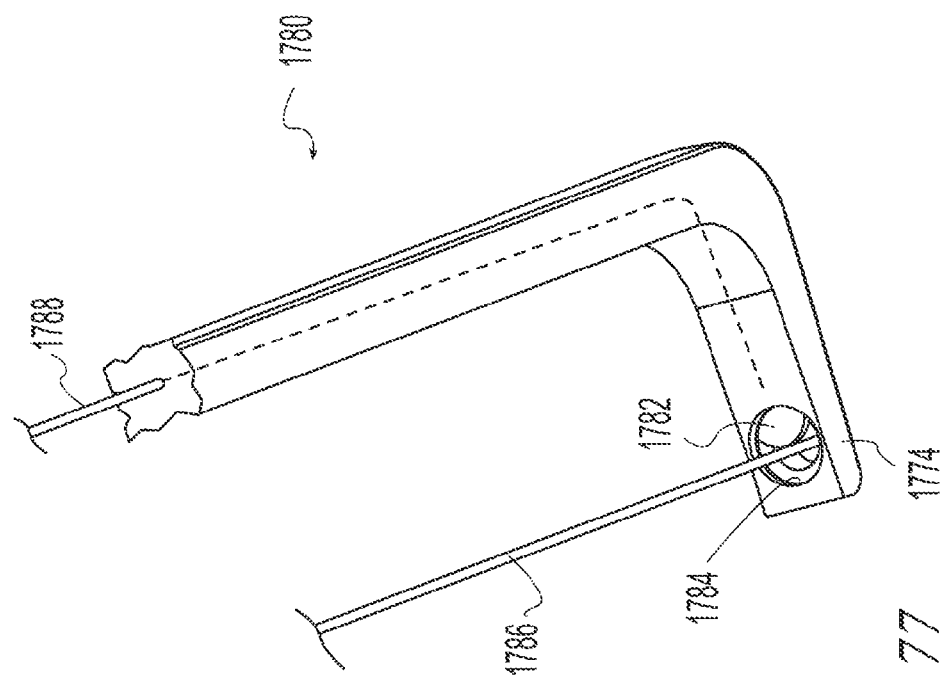
FIG. 77 is a perspective view of an alternative receiver useable with the suture passers of FIG. 51 and FIG. 52.

FIG. 77 illustrates an alternative foot 1780 to the foot 1324 of FIG. 52. The foot 1780 has moveable member 1782 mounted for movement relative to an opening 1784 between a first position in which the opening is not blocked and a suture 1786 may be received in the opening and a second position in which the member 1782 and edge of the opening 1784 grasp the suture. Any suitable mechanism may be used to move the member 1782. For example, a control cable 1788 may be mounted in the foot and moveable by a remote actuator to move the member 1782 between the first and second positions.

Figure 78:
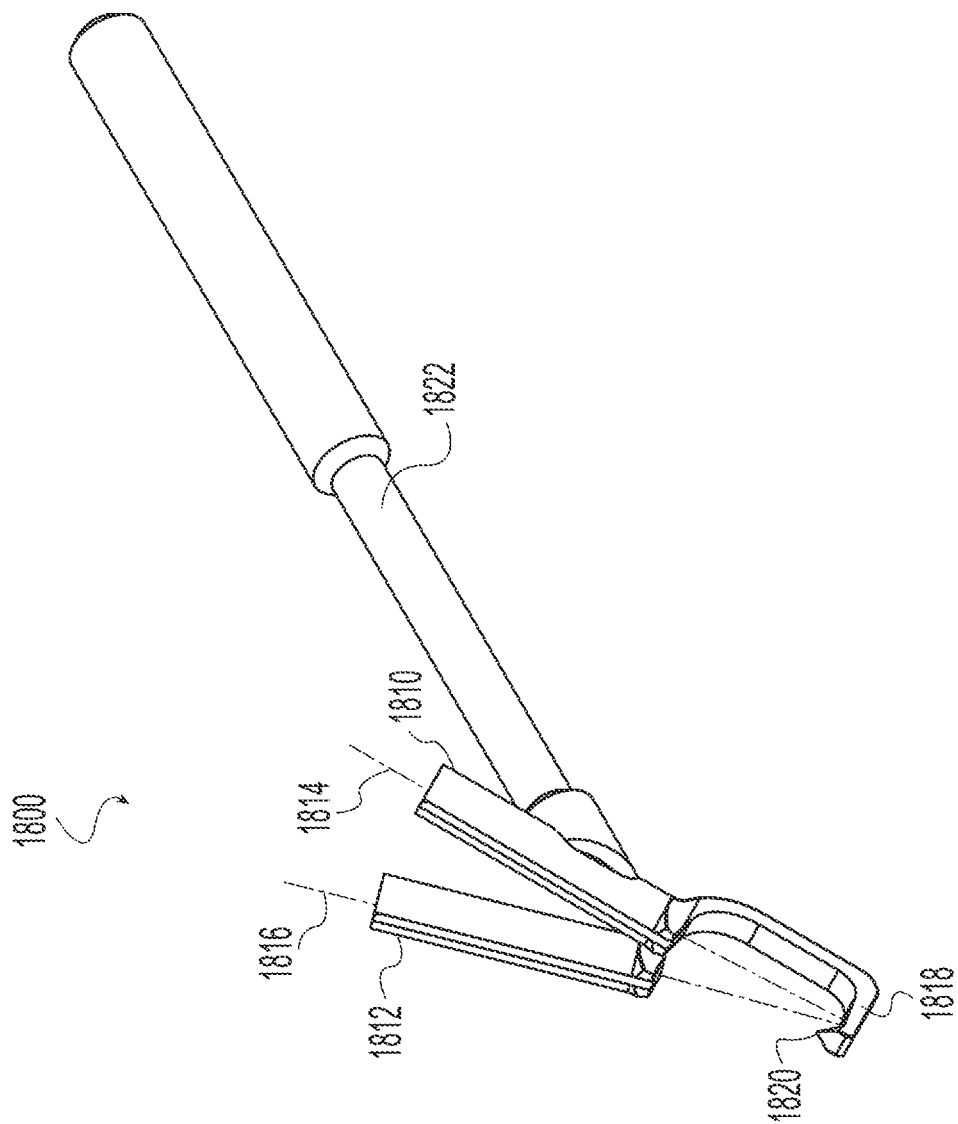
FIG. 78 is a perspective view of an illustrative example of a suture passer according to the present invention similar to that of FIG. 52.

FIG. 78 illustrates an illustrative example of an alternative configuration of the suture retriever 1300 of FIG. 52. In the illustrative example of FIG. 78, a suture retriever 1800 includes first and second guides 1810, 1812 each having a longitudinal guide axis 1814, 1816 and each mounted to the distal end of a handle 1822. The guide axes 1814, 1816 may be co-planar or they may lie in different planes. The guide axes 1814, 1816 may be parallel, they may bypass one another, or they may converge at a point. If they converge, they may converge distal to the foot 1818, at the foot 1818, or proximal to the foot 1818. For example, the guides 1810, 1812 may be oriented such that their axes do not converge and they can be used to guide a cutter to form non-converging holes in a bone. In another example, the guides 1810, 1812 may be oriented such that their axes converge proximal to the foot between the distal ends of the guides 1810, 1812 and the foot 1818 and they can be used to guide a cutter to form holes that intersect within, for example, a bone. In an exemplary method, the foot may be located at a desired location relative to a bone with a sharp tip 1820 embedded in the bone to help maintain the position of the retriever 1800. The first guide 1810 may be used to guide a cutter such as a drill to form a first tunnel in the bone. The second guide 1820 may be used to guide a cutter to form a second tunnel in the bone without the need to relocate the retriever 1800 to a second position.

The illustrative examples of FIGS. 51-78 have shown examples of a suture passer and its use to pass a suture used to pull a graft into a tunnel. However, a suture passed by the suture passer may be used in any way that sutures are known to be used. For example a suture may be used as a shuttle for pulling another suture, graft, or anything else from bottom to top rather than from top to bottom as depicted in the illustrative examples. Single strands, double strands, or any number of strands may be passed. Likewise one or more loops may be passed. Any of these may be used as a definitive suture in a repair or reconstruction, as a shuttle for pulling another material into a desired position, or for any other purpose.

FIGS. 79-101 illustrate the suture passers of FIGS. 5 and 52 in use to repair soft tissues. For example, the plantar plate, PCL, or ACL may be partially or fully torn due to acute trauma or chronic progressive failure. Likewise, these soft tissues may be intentionally released from their bony origins or attachments to facilitate a surgical procedure. The instruments and techniques of the present invention provide a way to repair these soft tissues.

Figure 82:
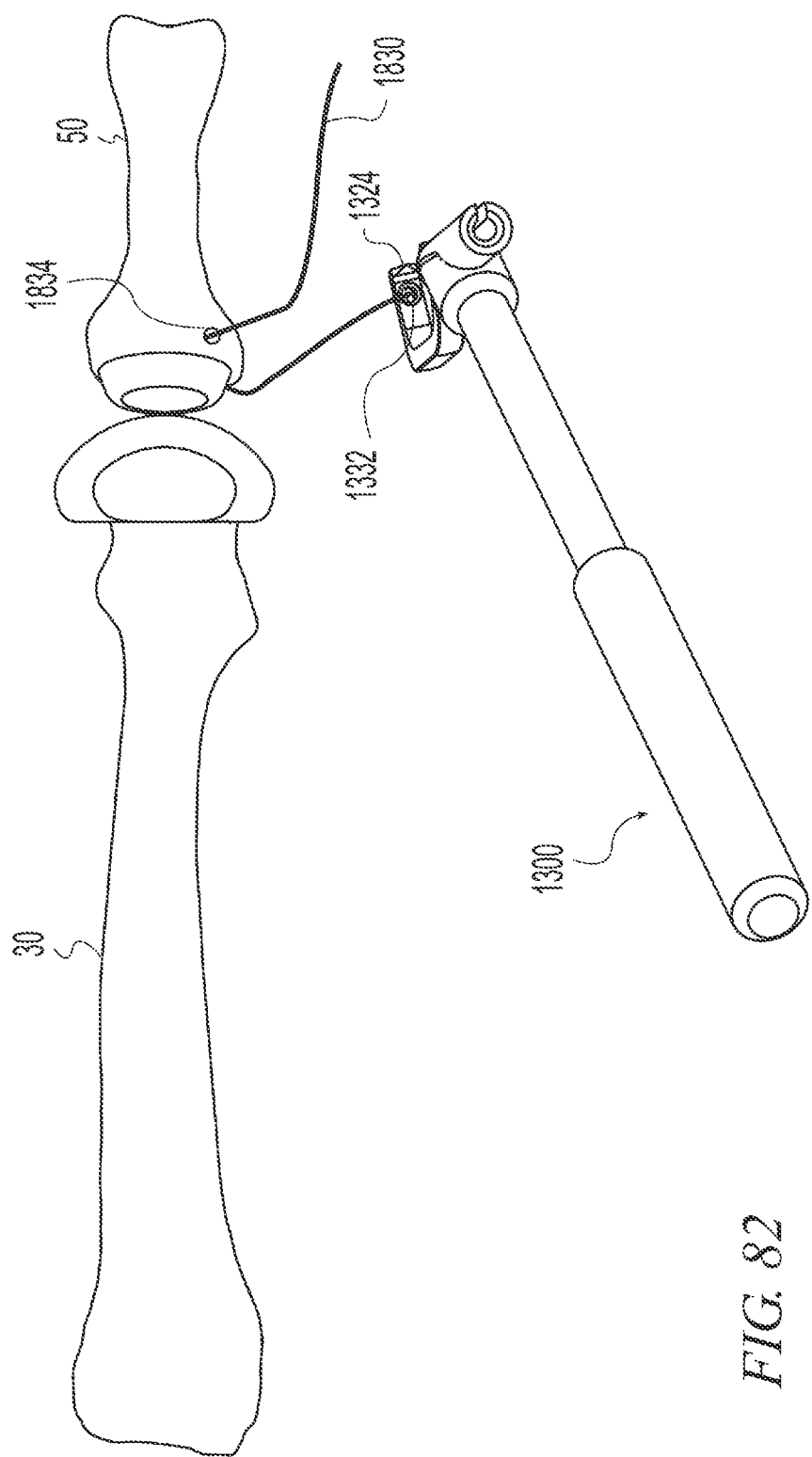
Figure 83:
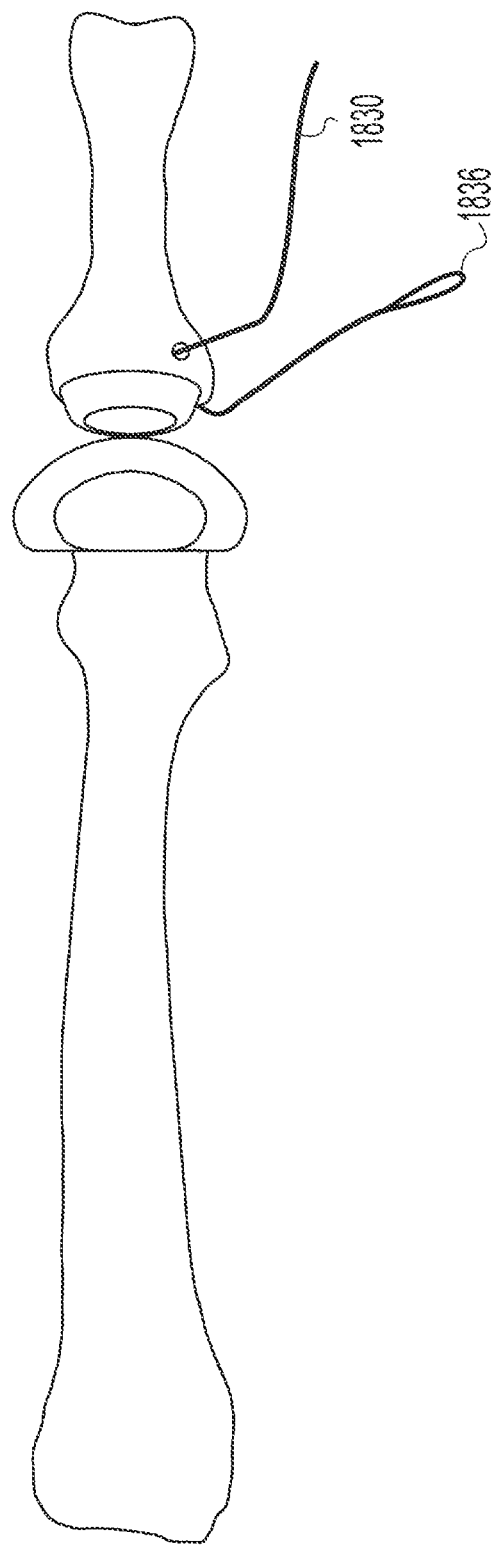
Figure 84:
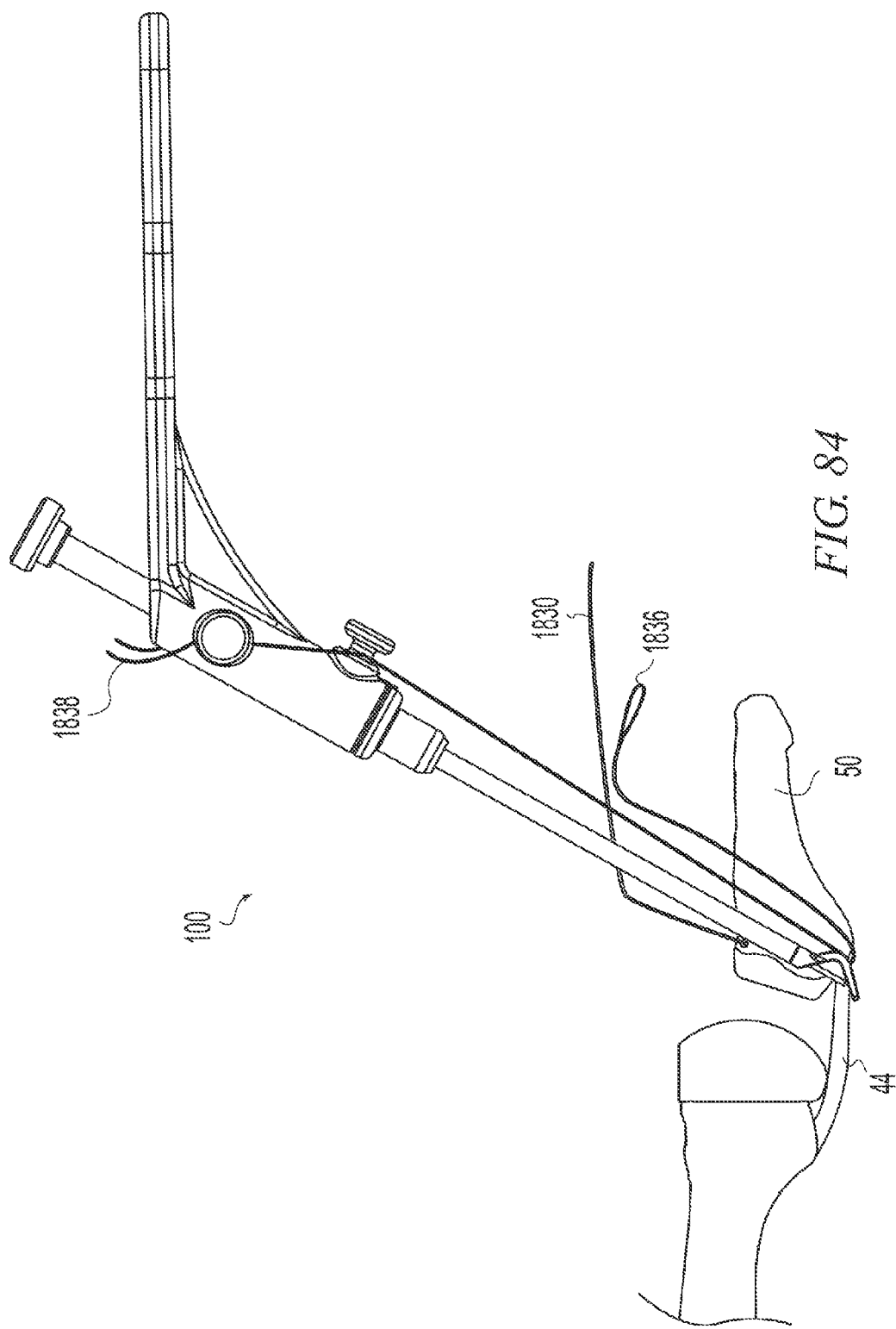

FIGS. 79-86 depict an illustrative method to repair a partial tear of the plantar plate 44 (FIG. 84). For example, the plantar plate may be torn on one side for less than 50% of its width where it attaches to the proximal phalanx 50. Such a tear may be referred to as a Coughlin Grade 1 tear or simply as a corner tear.

Figure 79:
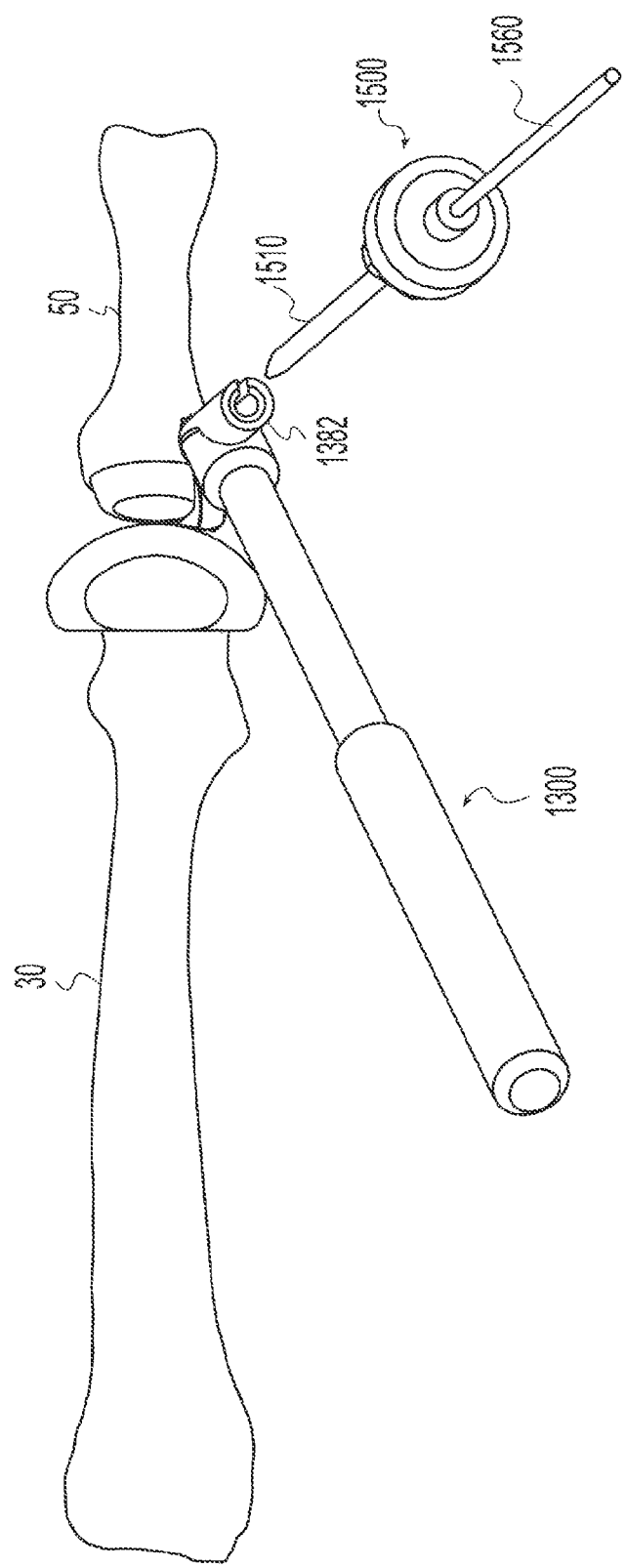

In FIG. 79, the suture retriever 1300 of FIG. 52 has been positioned with its foot 1324 toward the plantar aspect of the proximal end of the proximal phalanx with the opening 1332 at a desired tunnel exit and the guide tube 1382 aligned with a desired tunnel entrance. In the illustrative method of FIGS. 79-86, the plantar plate tear is on the lateral side and the suture retriever 1300 has been positioned to create a bone tunnel on the lateral side of the proximal phalanx 50. The drill assembly 1500 is guided by the guide tube 1382 to form a bone tunnel 1834 (FIG. 82).

Figure 80:
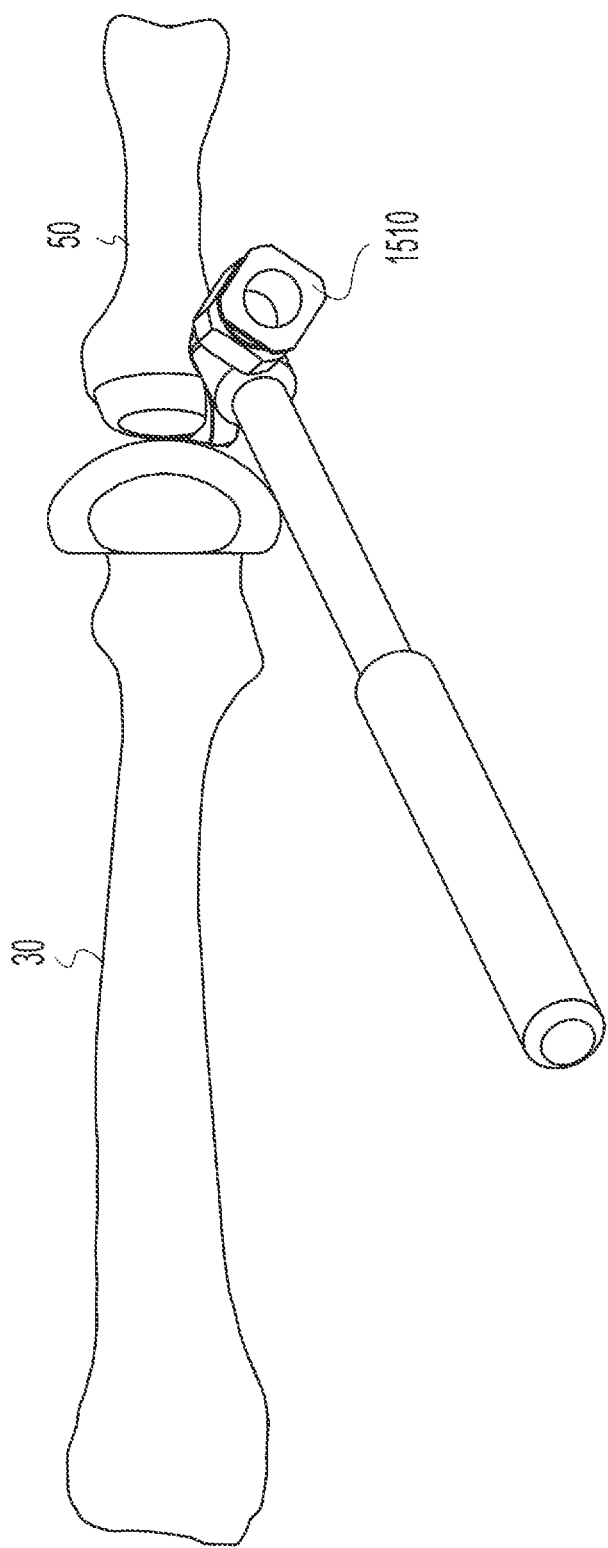

In FIG. 80, the obturator 1560 has been removed leaving the drill tube 1510 in place to guide a first, or passing, suture 1830 to the opening 1332 in the foot 1324.

Figure 81:
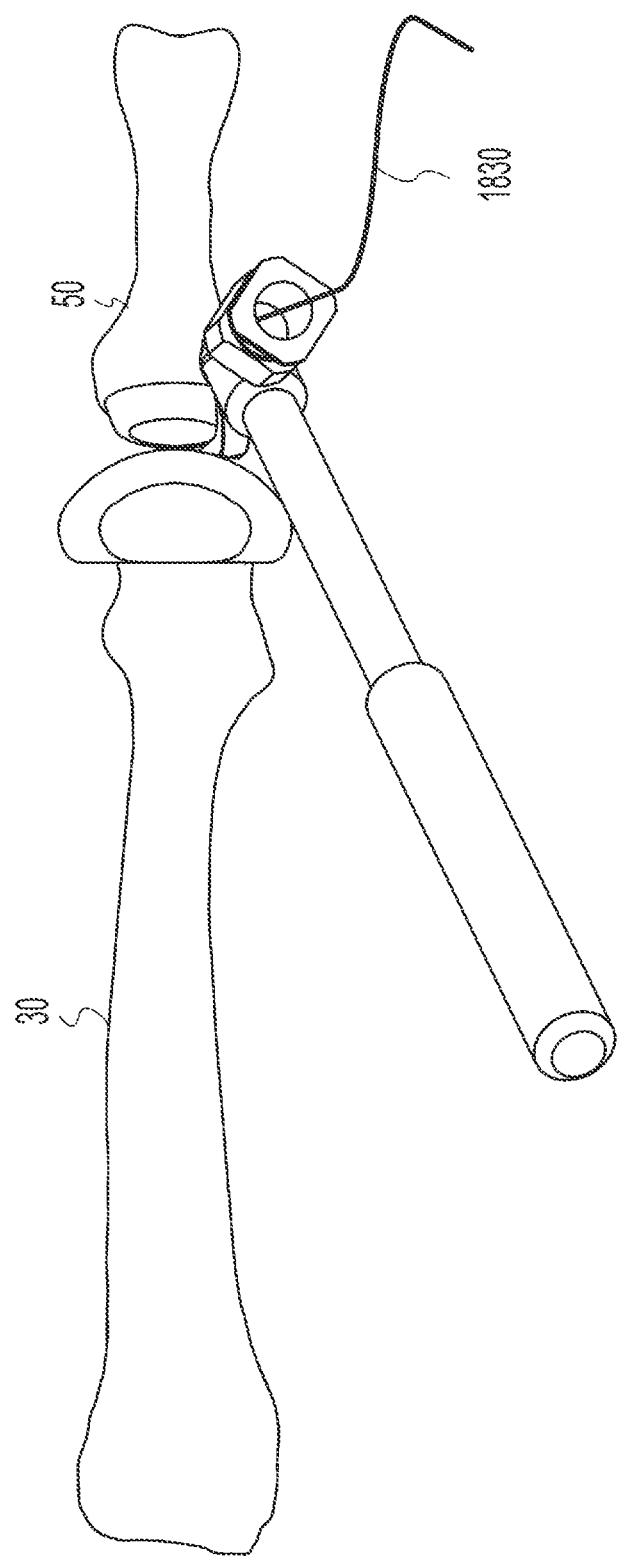

In FIG. 81, the first suture 1830 has been inserted until a stopper 1832 at its distal end is passed through the opening 1332 to engage the foot 1324 (FIG. 82).

In FIG. 82, the suture retriever 1300 has been withdrawn from the proximal phalanx 50 pulling the distal end of the first suture 1830 with it to advance the first suture 1830 in the bone tunnel 1834.

In FIG. 83, the stopper has been cut off of the distal end of the first suture 1830 to free the first suture from the retriever 1300 and the distal end of the first suture 1830 has been tied to form a loop 1836. Alternatively, the loop 1836 may be provided preformed on the first suture 1830.

In FIG. 84, the suture passer 100 of FIG. 5 is shown in use to form a stitch with a second, or repair, suture 1838 through the lateral portion of the plantar plate 44 adjacent the tear near the insertion of the plantar plate 44 onto the proximal phalanx 50. Multiple stitches may be created. Also, the second suture 1838 may be tensioned to apply traction to the plantar plate 44 to better expose the plantar plate 44 to facilitate placing additional stitches or additional sutures.

Figure 85:
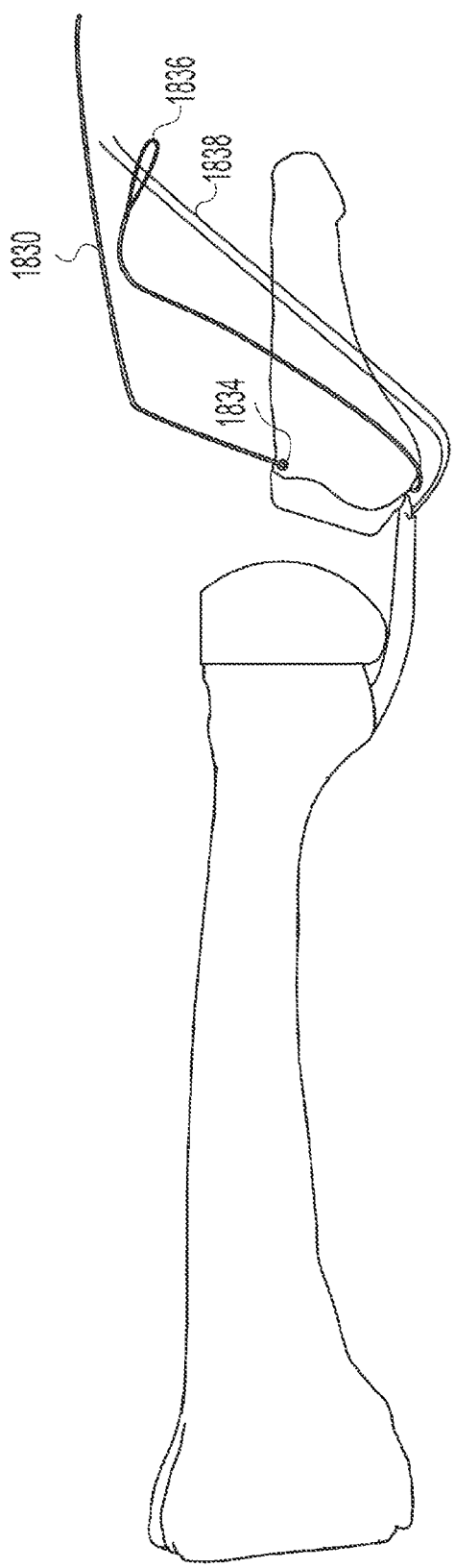

In FIG. 85, the ends of the second suture 1838 are placed through the loop 1836 of the first suture 1830 in preparation for pulling the second suture 1838 through the bone tunnel 1834.

Figure 86:
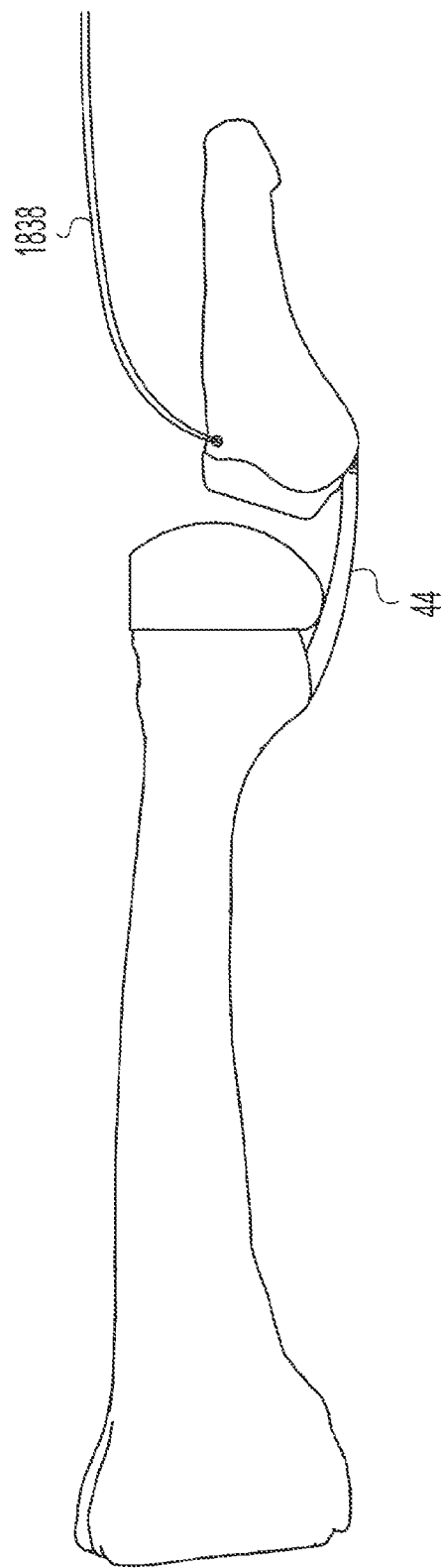

In FIG. 86, the first suture 1830 has been pulled back through the bone tunnel pulling the second suture 1838 with it and the second suture 1838 has been tensioned to reattach the torn portion of the plantar plate 44. The suture may be secured by any suitable method such as tying, securing over a button, securing with an interference fastener, or other suitable method.

Figure 87:
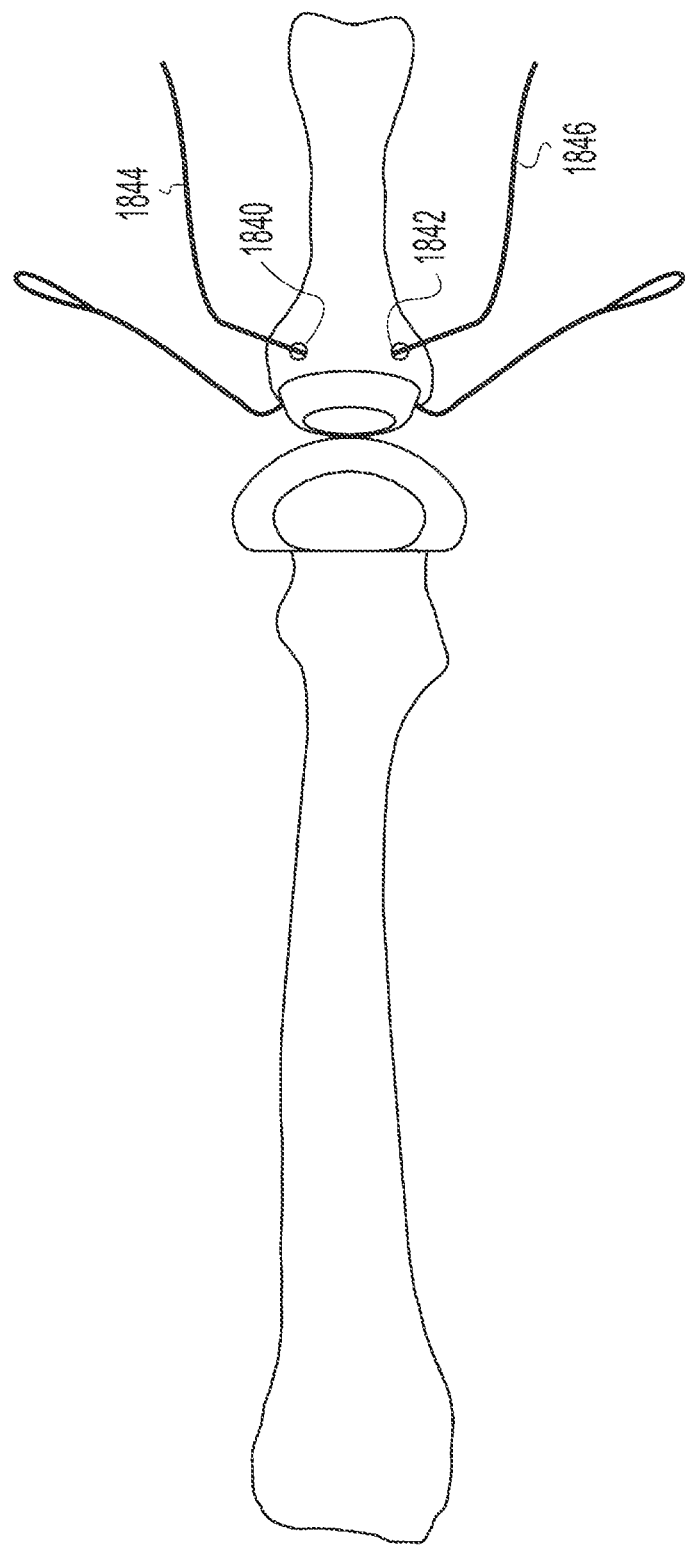

FIGS. 87-91 depict an illustrative method to repair a more extensive tear of the plantar plate 44 than that of FIGS. 79-86. For example, the plantar plate may be torn for more than 50% of its width where it attaches to the proximal phalanx 50 such as in a Coughlin Grade II tear, it may be torn from both sides, or it may be completely separated from the proximal phalanx. In the illustrative example of FIGS. 87-91, the plantar plate has been completely separated from the proximal phalanx. In FIG. 87 the suture retriever 1300 has been used as in FIGS. 79-83 to create a medial bone tunnel 1840 and a lateral bone tunnel 1842 to position two passing sutures 1844, 1846 in the tunnels.

Figure 88:
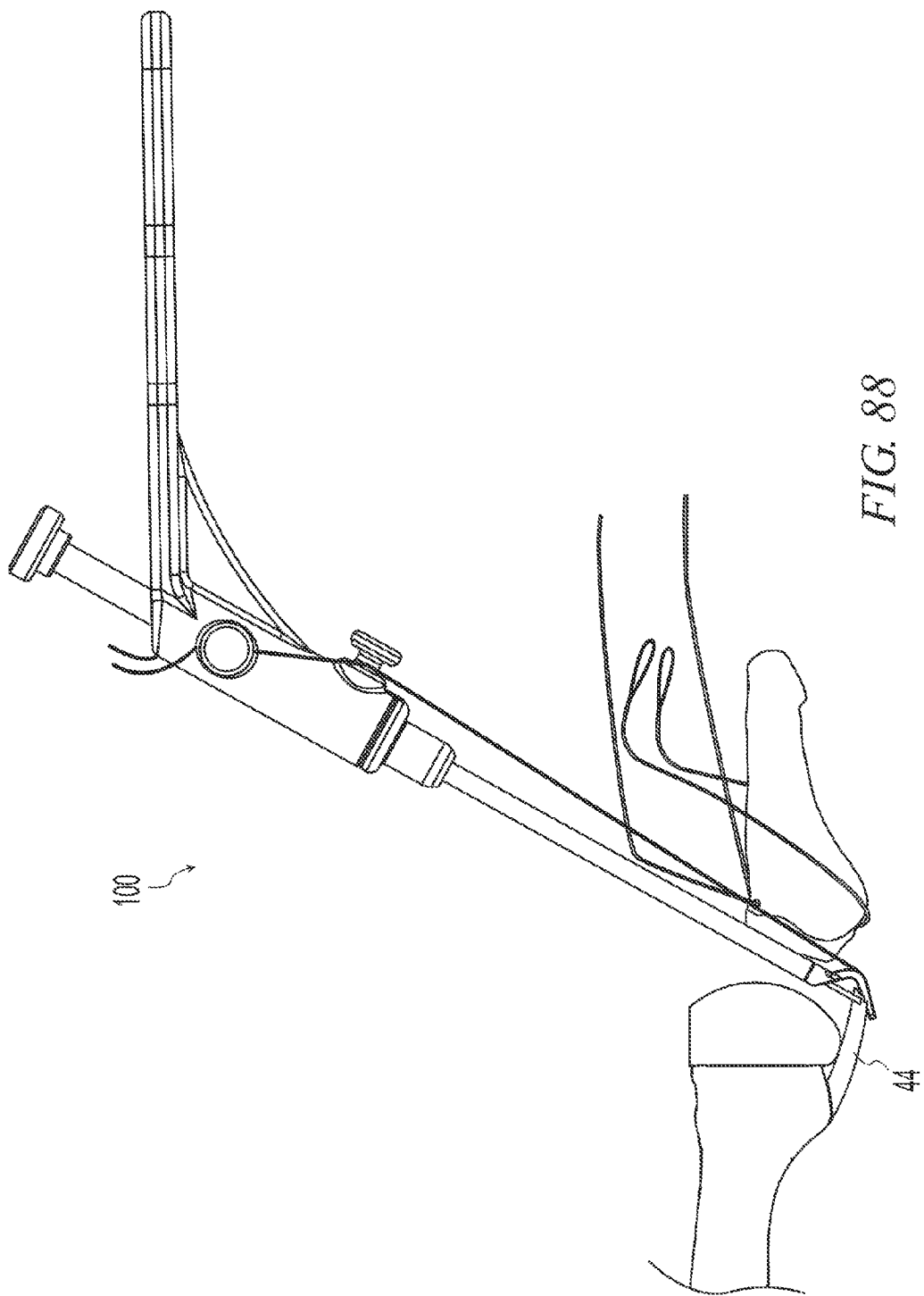
Figure 89:
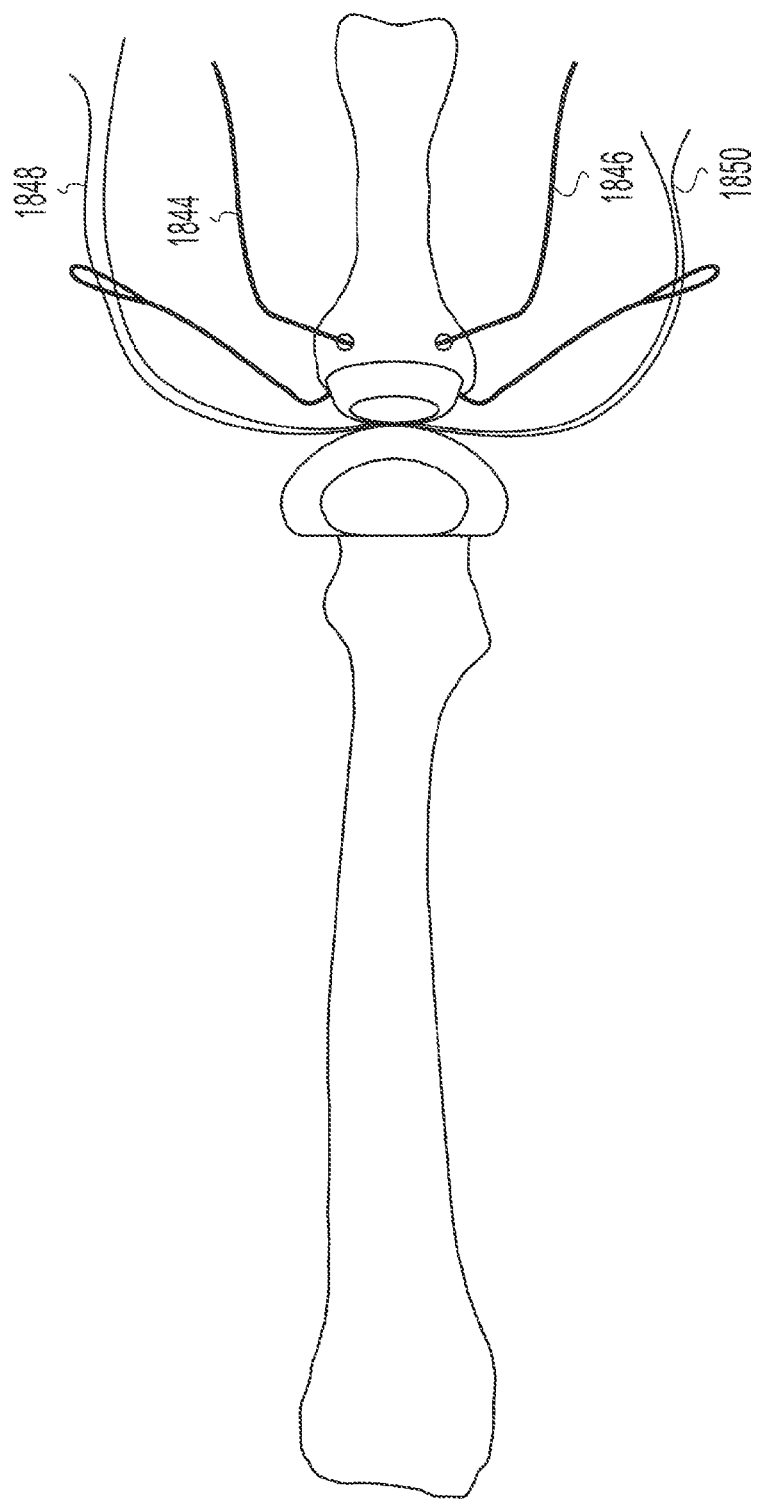
Figure 90:
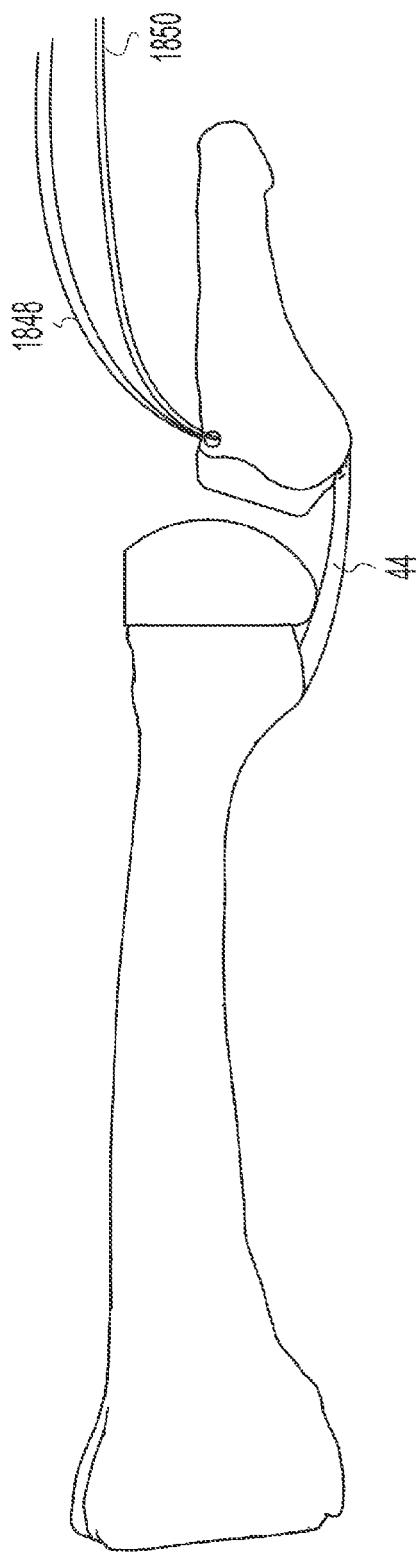

In FIG. 88, the suture passer 100 is used to place one or more repair sutures into the torn end of the plantar plate 44. In the illustrative example of FIGS. 87-91 two repair sutures 1848, 1850 are used and their ends are passed through the tunnels 1840, 1842 with the passing sutures 1844, 1846 as shown in FIGS. 89 and 90. An initial traction suture may be passed through the plantar plate and tensioned to apply traction to the plantar plate 44 to better expose the plantar plate 44 to facilitate placing additional stitches or additional sutures.

In FIG. 90, the repair sutures 1848, 1850 have been tensioned to reattach the plantar plate 44.

Figure 91:
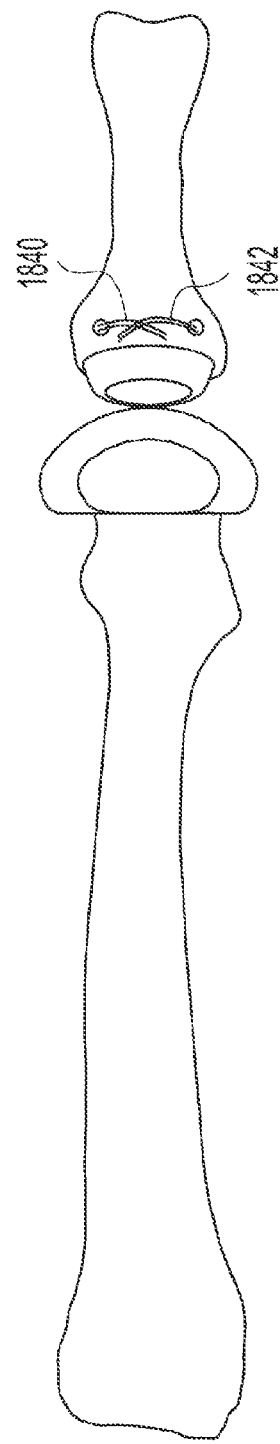

In FIG. 91, the repair sutures 1848, 1850 have been tied together over the bone bridge between the two tunnels 1840, 1842 to secure the plantar plate 44.

FIGS. 92-97 depict an illustrative method to repair a PCL. In the illustrative example of FIGS. 92-97, the medial PCL 36 is detached from its bony insertion on the proximal phalanx.

Figure 92:
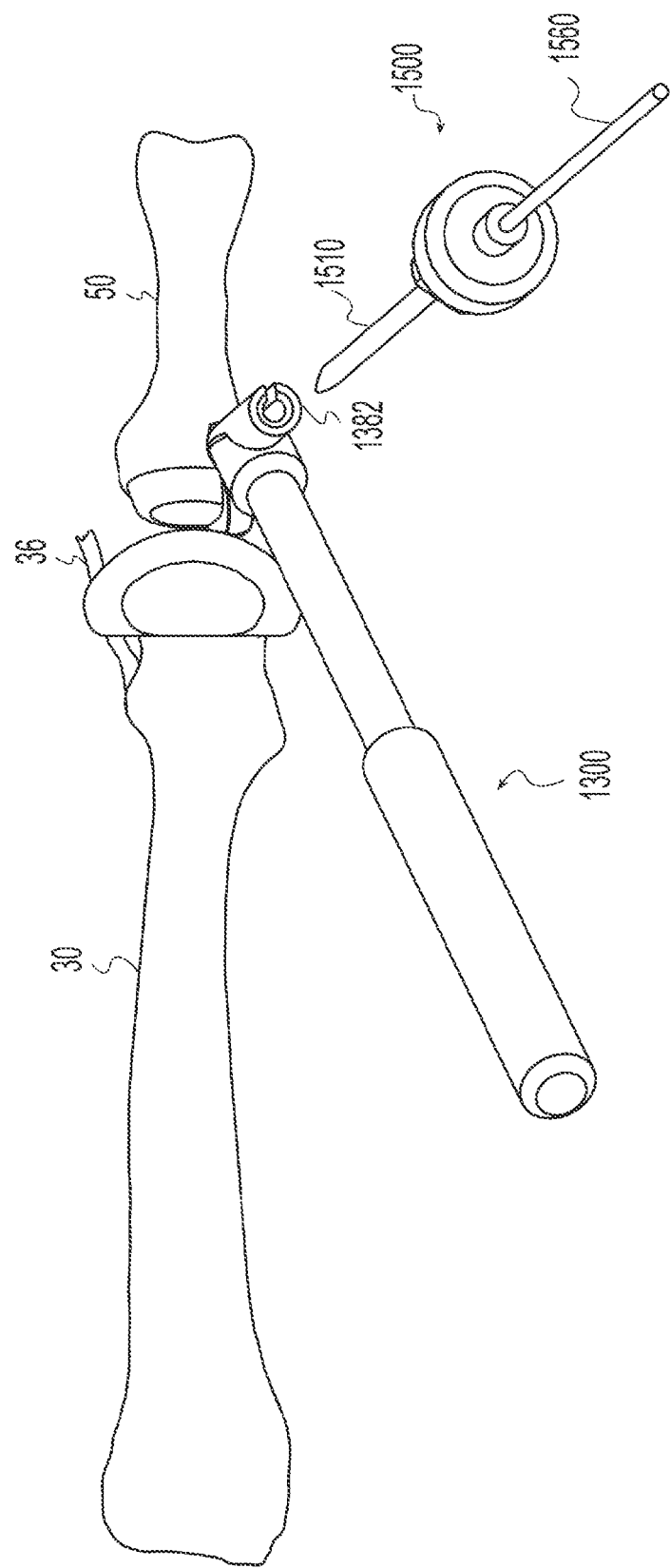

In FIG. 92, the suture retriever 1300 of FIG. 52 has been positioned with its foot 1324 toward the medial-plantar aspect of the proximal end of the proximal phalanx with the opening 1332 at the medial PCL insertion. The guide tube 1382 is aligned with the lateral-dorsal aspect of the proximal phalanx so that the tunnel crosses through the proximal phalanx and exits at the PCL insertion. The suture retriever 1300 allows the surgeon to place bone tunnels at any desired location and orientation to compliment a desired repair technique. The drill assembly 1500 is guided by the guide tube 1382 to form a bone tunnel 1852.

Figure 93:
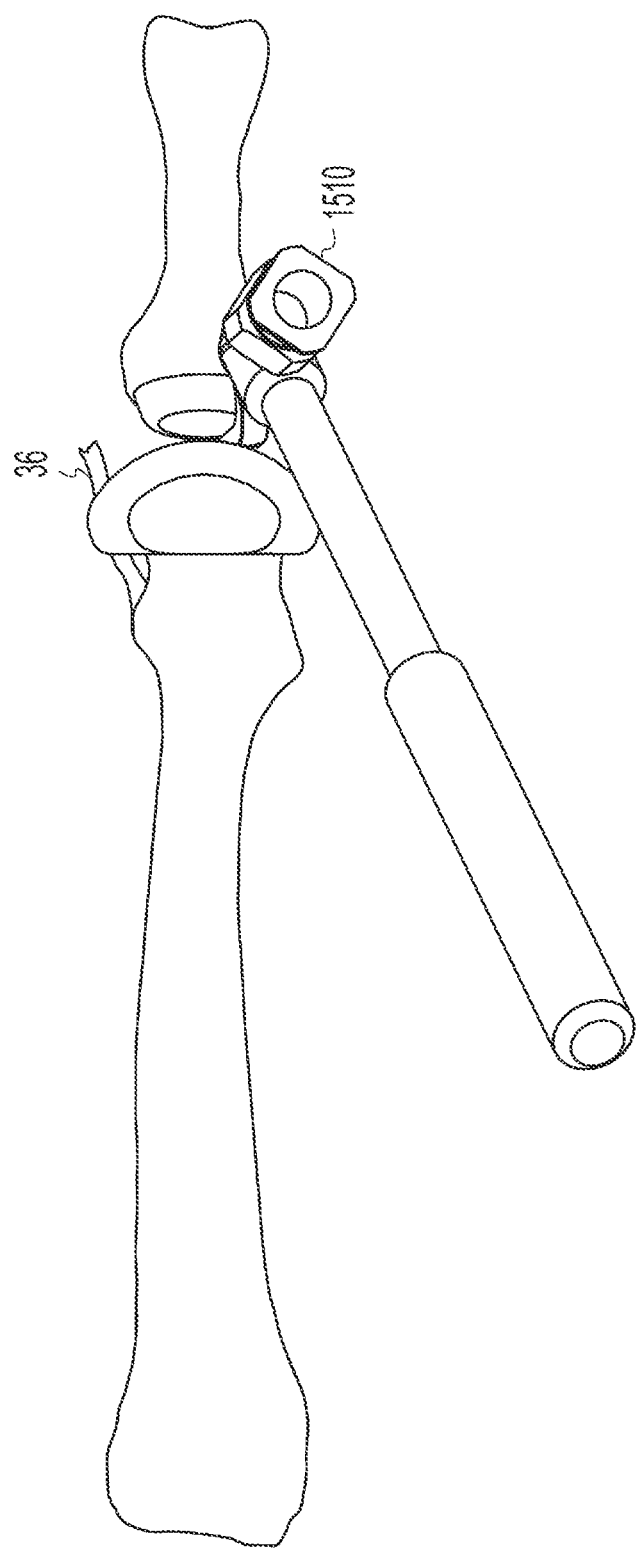

In FIG. 93, the obturator 1560 has been removed leaving the drill tube 1510 in place to guide a first, or passing, suture 1854 to the opening 1332 in the foot 1324.

Figure 94:
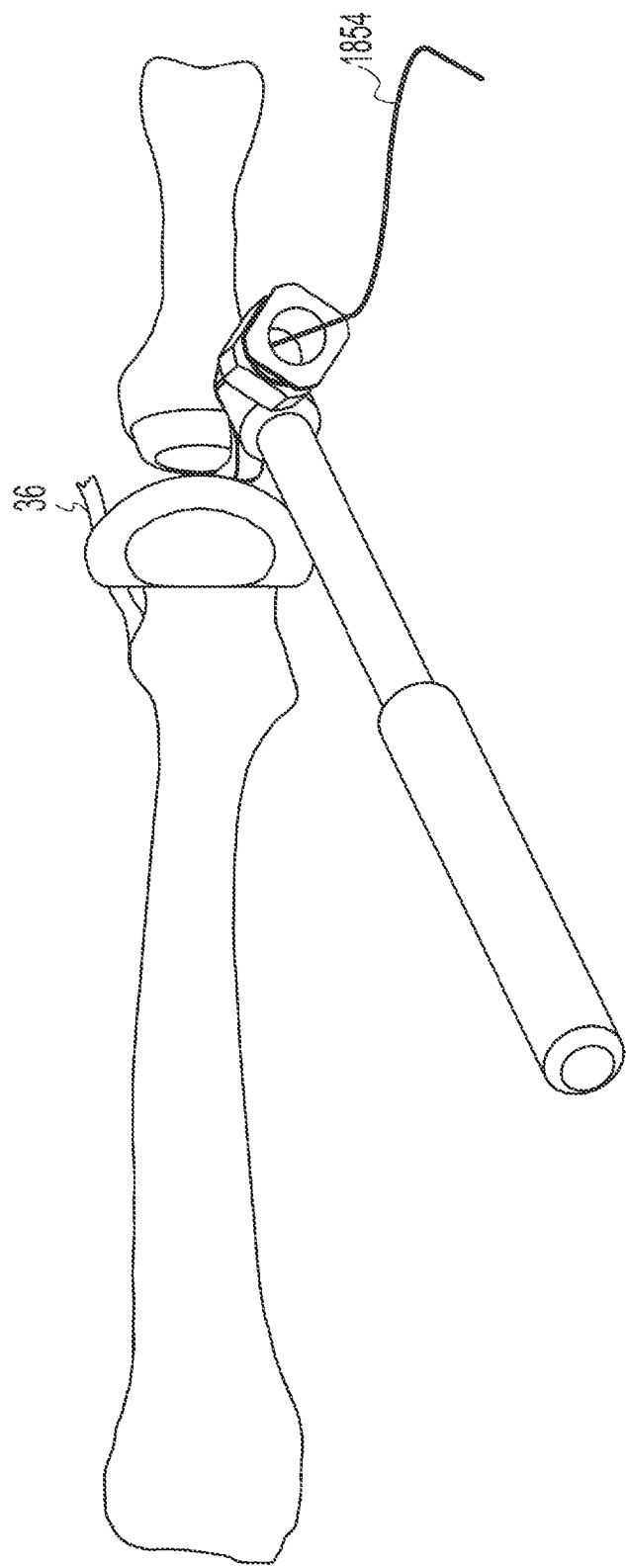

In FIG. 94, the first suture 1854 has been inserted until a stopper at its distal end is passed through the opening 1332 to engage the foot 1324

Figure 95:
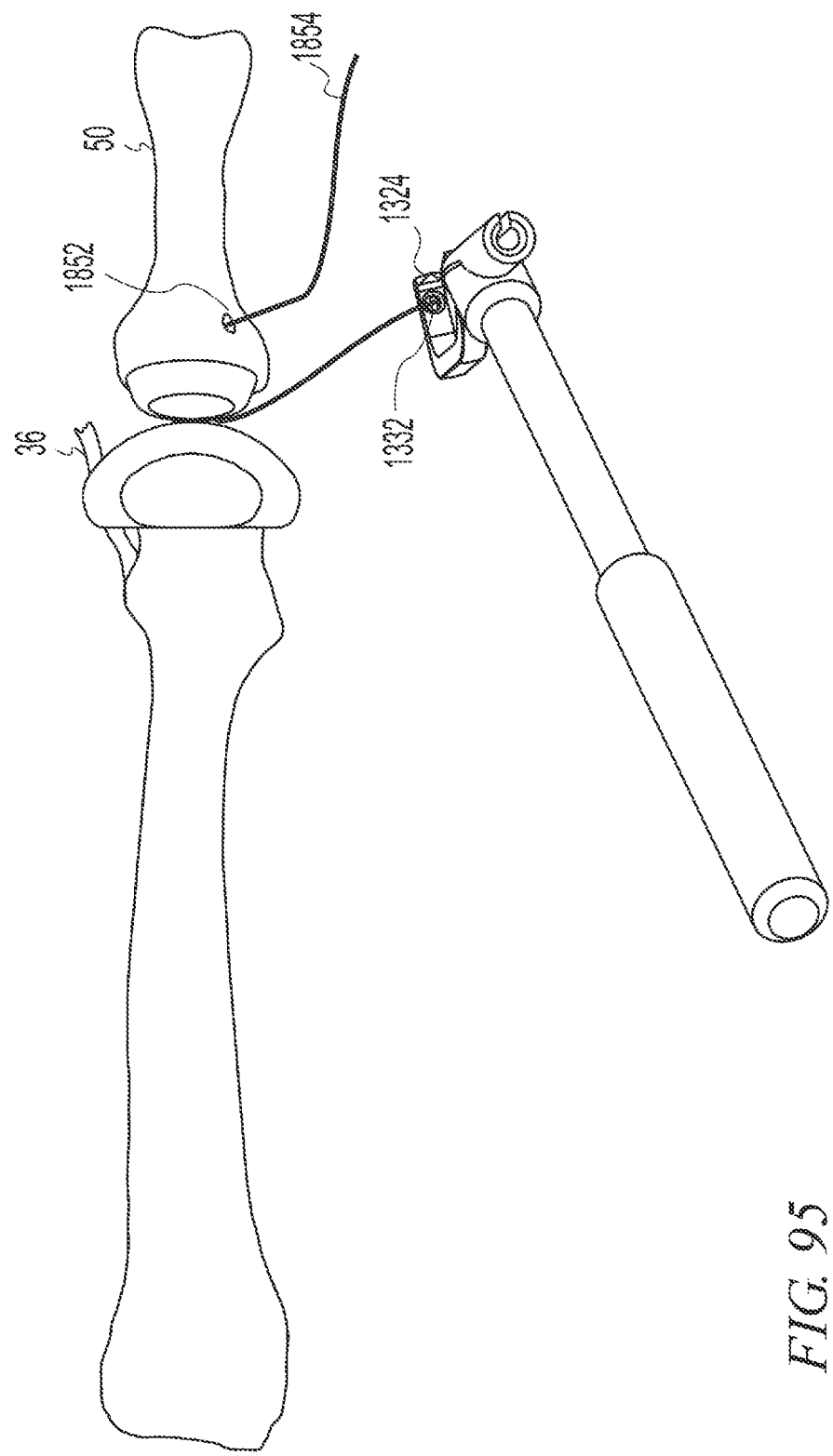

In FIG. 95, the suture retriever 1300 has been withdrawn from the proximal phalanx 50 pulling the distal end of the first suture 1854 with it to advance the first suture 1854 in the bone tunnel 1852.

Figure 96:
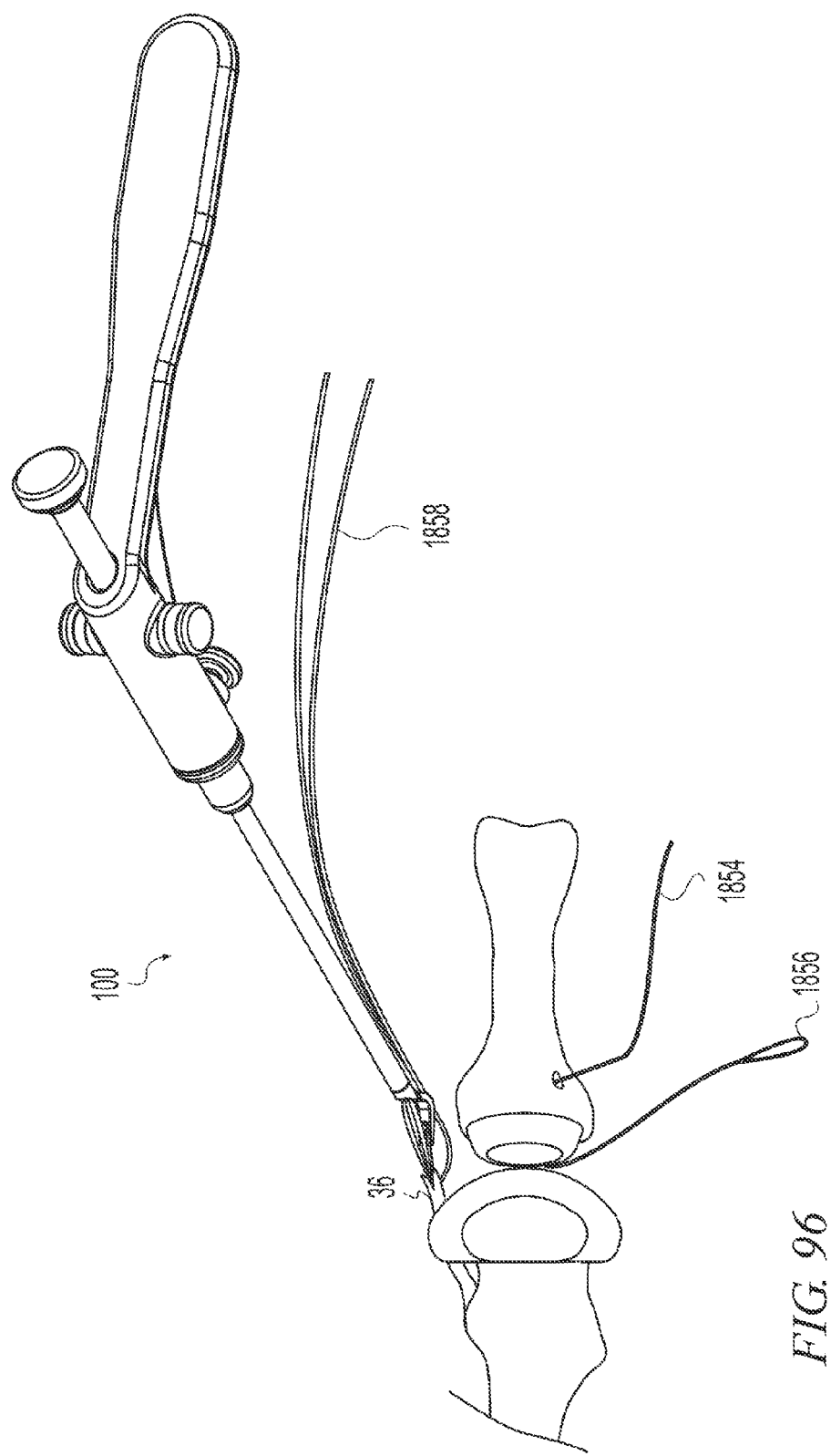

In FIG. 96, the stopper has been cut off of the distal end of the first suture 1854 to free the first suture from the retriever 1300 and the distal end of the first suture 1854 has been tied to form a loop 1856. Alternatively, the loop 1856 may be provided preformed on the first suture 1854. The suture passer 100 of FIG. 5 is shown in use to form a stitch with a second, or repair, suture 1858 through the distal end of the medial PCL 36. Multiple stitches may be created.

Figure 97:
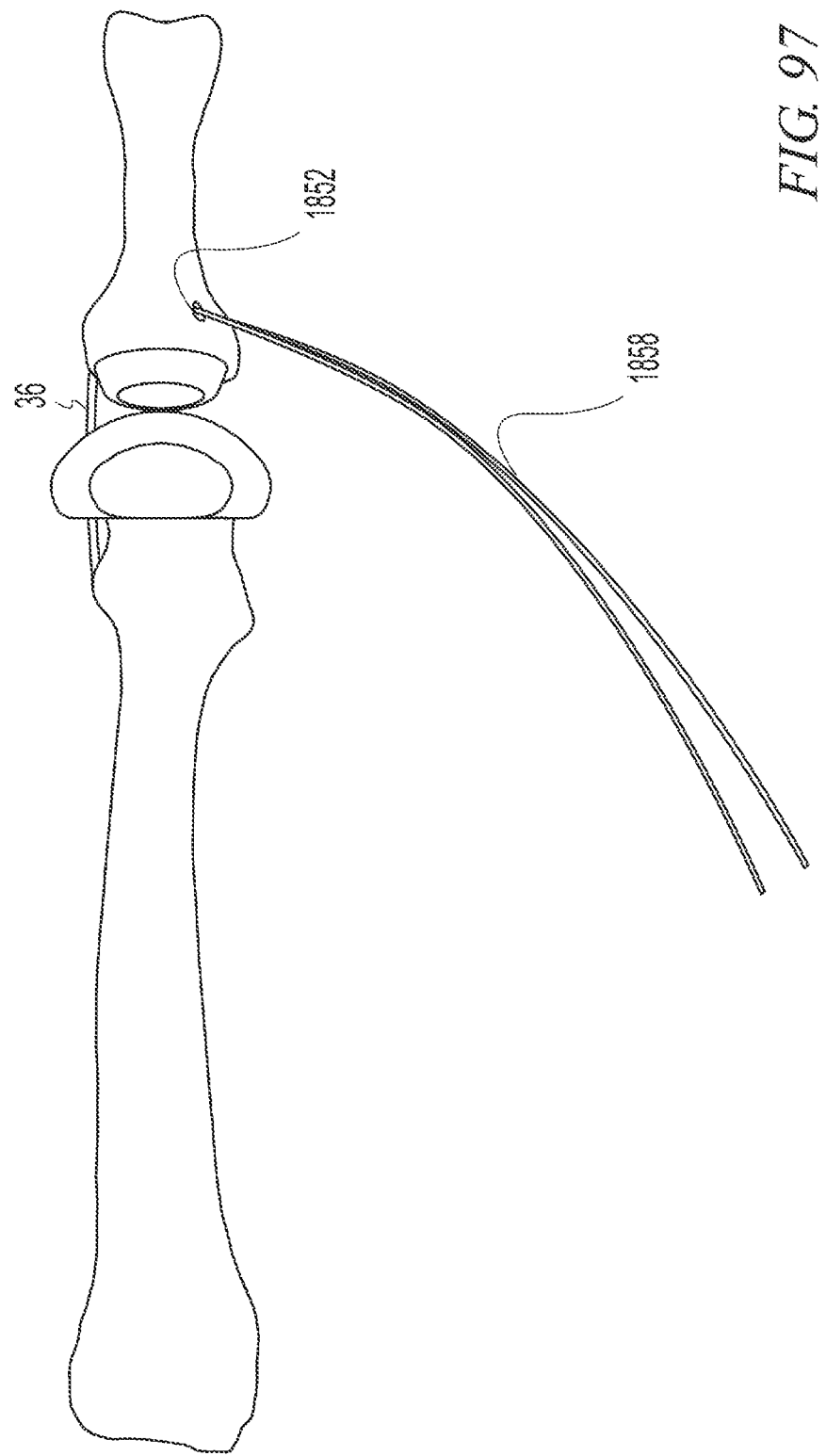

In FIG. 97, the ends of the second suture 1858 have been placed through the loop 1856 of the first suture 1854 and pulled through the bone tunnel 1852. The second suture 1858 has been tensioned to reattach the medial PCL. The suture may be secured by any suitable method such as tying, securing over a button, securing with an interference fastener, or other suitable method.

Figure 98:
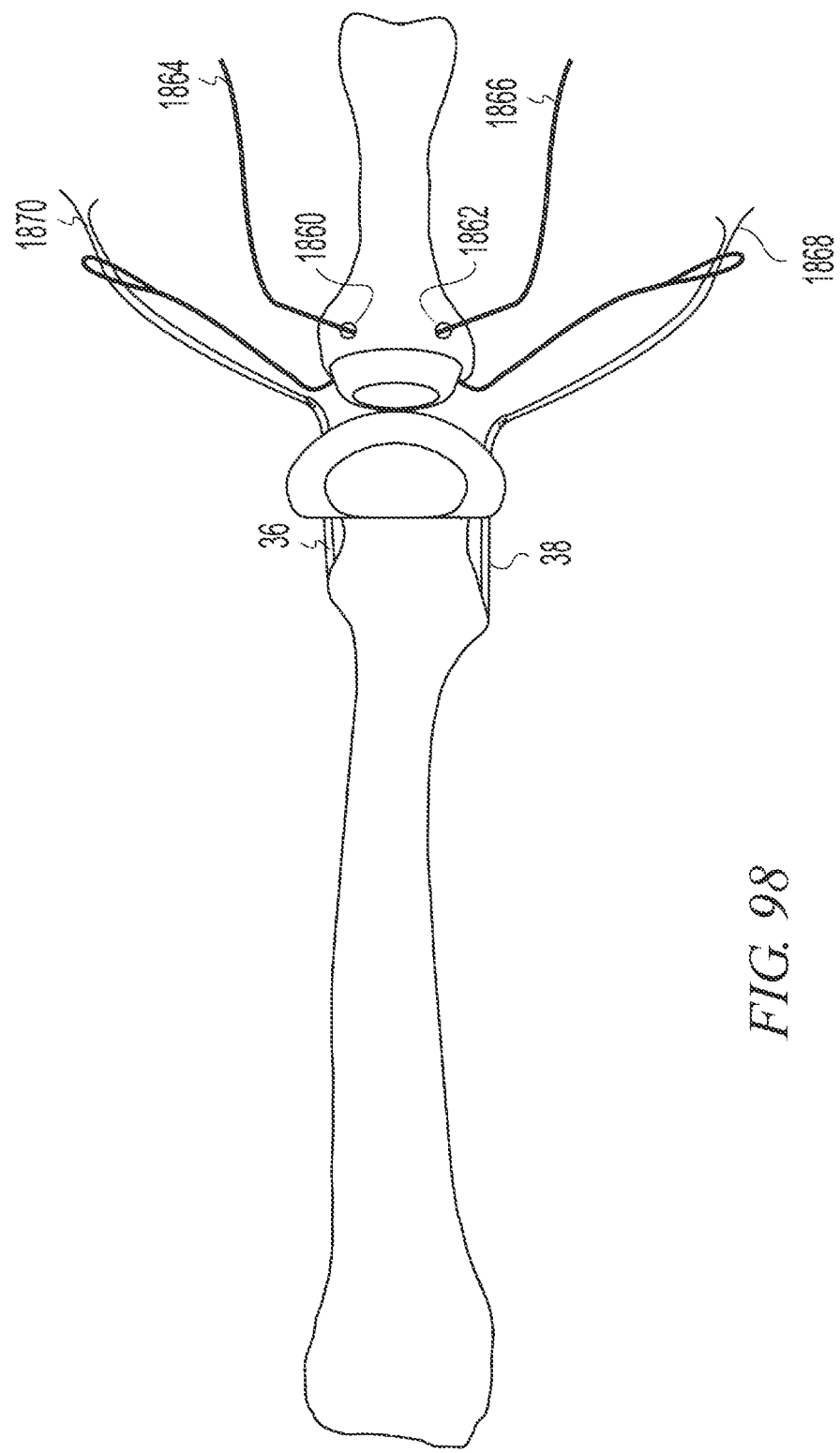
Figure 99:
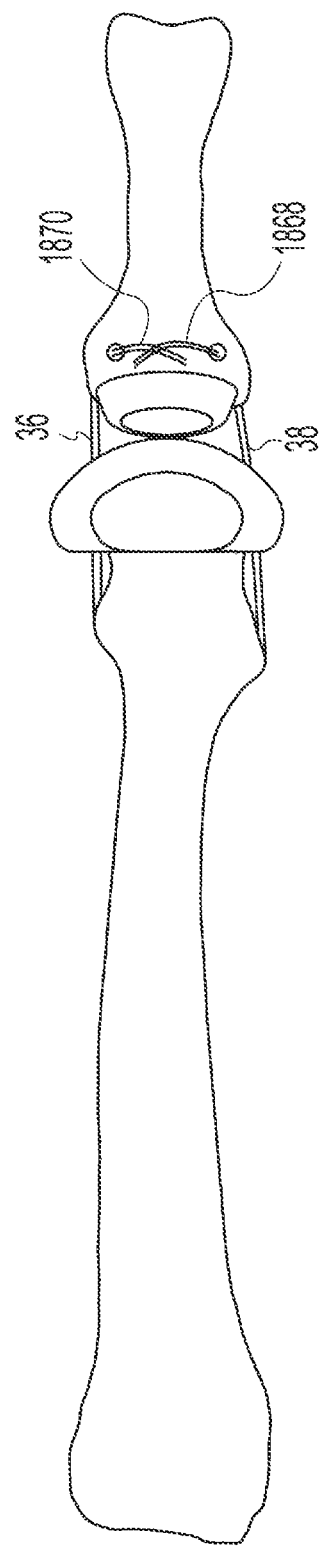

FIGS. 98 and 99 depict an illustrative method for a bilateral PCL repair in which both the lateral and medial PCLs are repaired using tunnels 1860, 1862 that pass one another as they cross the proximal phalanx 30 without intersecting to exit at the lateral and medial PCL insertions respectively. Passing sutures 1864, 1866 are used to pull repair sutures 1868, 1870 through the bone tunnels 1860, 1862. The repair sutures 1868, 1879 are used to secure the lateral and medial PCLs 38, 36.

FIGS. 100 and 101 depict an illustrative method to repair an ACL. This repair may be performed unilaterally or bilaterally similar to the illustrative examples depicted for the plantar plate and PCL. The ACLs originate coincident with the PCLs and insert into the junction between the edges of the plantar plate 44 and the transverse intermetatarsal ligament (IML) 1890. The IML is a narrow band of connective tissue that extends between and connects together the heads of the metatarsal bones. In the illustrative method of FIGS. 100 and 101, a bilateral ACL repair according to the present invention is depicted in which both the medial and lateral ACLs 40, 42 have been repaired. The method begins as in the bilateral PCL repair with the formation of bone tunnels 1871, 1872 in the proximal phalanx. Passing sutures (not shown) are placed through the tunnels 1871, 1872 using a suture retriever such as suture retriever 1300 of FIG. 52. The severed ends of the ACL's 40, 42 are located and the ends of the ACLs are stitched such as with the suture passer 100 of FIG. 5 with one or more stitches. Each repair suture 1874, 1876 is passed through the IML 1890 at the anatomic insertion of the ACL. The repair sutures 1874, 1876 are passed through the bone tunnels using the passing sutures. The repair sutures 1874, 1876 are secured. For example, in a bilateral repair the sutures may be tied together as shown in FIG. 101.

The illustrative examples have depicted repairs of soft tissues adjacent the MTP joint of the human foot and have shown the repairs in use to attach the insertion end of the soft tissue to the proximal phalanx. It is also within the scope of the present invention to repair soft tissues detached at their origins by forming tunnels in the metatarsal bone, stitching the detached ends, and pulling the repair sutures through the metatarsal tunnels. It is also within the scope of the invention to repair soft tissues adjacent other joints. Furthermore, the illustrative examples have depicted discrete repairs of the PP, PCL, and ACL. However, it is to be understood that one or more unilateral or bilateral repairs may be combined to repair multiple soft tissues. For example, the PP repair may be combined with the PCL repair and utilize the same tunnels or additional tunnels may be created. Likewise, the PP and ACL repairs may be combined. Likewise, the PCL and ACL repairs may be combined. Likewise, the PP, PCL, and ACL repairs may be combined. Finally, similar repairs of the joints of the hand are within the scope of the invention.

What is claimed is:

1. A method of repairing soft tissue of a joint of a human extremity, the joint including a metapodial bone and a proximal phalanx, the extremity having volar and dorsal aspects, the method comprising:
   maintaining the metapodial bone intact;
   forming a bone tunnel through the proximal phalanx between volar and dorsal aspects of the proximal phalanx;
   passing a repair suture through the soft tissue to be repaired;
   passing the repair suture through the bone tunnel; and
   securing the suture;
   wherein the soft tissue to be repaired comprises a collateral ligament, the method further comprising after passing a repair suture through the soft tissue to be repaired and before passing the repair suture through the bone tunnel:
      passing the repair suture into a transverse ligament connecting adjacent metapodial bones of the extremity.

2. The method of claim 1, wherein forming the bone tunnel comprises forming the bone tunnel proximally adjacent to the anatomic collateral ligament insertion on the proximal phalanx.

3. The method of claim 1, wherein the collateral ligament comprises medial and lateral collateral ligaments,
   wherein forming a bone tunnel comprises forming first and second bone tunnels between volar and dorsal aspects of the proximal phalanx,
   wherein passing a repair suture through the soft tissue to be repaired comprises passing a first repair suture through the medial collateral ligament and passing a second repair suture through the lateral collateral ligament,
   wherein passing a repair suture through the bone tunnel further comprises passing the first repair suture through the first tunnel and passing the second repair suture through the second tunnel, and
   wherein passing the repair suture into the transverse ligament connecting adjacent metapodial bones of the extremity comprises:
      passing the first repair suture through the transverse ligament connecting adjacent metapodial bones of the extremity medial of the joint; and
      passing the second repair suture through the transverse ligament connecting adjacent metapodial bones of the extremity lateral of the joint.

* * * * *